United States Patent
Bizzarro et al.

(10) Patent No.: US 6,528,543 B1
(45) Date of Patent: Mar. 4, 2003

(54) UREA DERIVATIVES

(75) Inventors: Fred Thomas Bizzarro, Colonia, NJ (US); Wendy Lea Corbett, Randolph, NJ (US); Antonio Focella, Wayne, NJ (US); Joseph Francis Grippo, Stirling, NJ (US); Nancy-Ellen Haynes, Cranford, NJ (US); George William Holland, North Caldwell, NJ (US); Robert Francis Kester, Hackensack, NJ (US); Paige Erin Mahaney, Montclair, NJ (US); Ramakanth Sarabu, Cedar Grove, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/532,506

(22) Filed: Mar. 21, 2000

Related U.S. Application Data
(60) Provisional application No. 60/165,948, filed on Nov. 17, 1999, and provisional application No. 60/126,707, filed on Mar. 29, 1999.

(51) Int. Cl.$^7$ .................. A61K 31/17; A61K 31/215; A61K 31/275; A61K 31/325
(52) U.S. Cl. .................. 514/594; 514/522; 514/530; 514/542; 514/595; 558/413; 558/417; 560/9; 560/13; 564/47; 564/56
(58) Field of Search ................... 514/594, 522, 514/530, 542, 595; 564/47, 56; 558/413, 417; 560/9, 13

(56) References Cited

U.S. PATENT DOCUMENTS
| | | | |
|---|---|---|---|
| 3,431,301 A | 3/1969 | Focella et al. | 260/558 |
| 3,776,917 A | 12/1973 | Mann et al. | 260/296 R |

FOREIGN PATENT DOCUMENTS
| | | |
|---|---|---|
| DE | 249 241 | 7/1912 |
| ES | 472 295 | 8/1978 |
| JP | 56059755 | 5/1981 |

OTHER PUBLICATIONS
Speilman et al., Journal of American Chemical Society, vol. 70, pps. 4189–4191 (1948).
Ribalta et al., Arzneim.–Forsch, 31(10A), p. 1782–1786 (1981).
Spickett et al., Eur. J. Med. Chem.—Chim. Ther., 11(1), p. 7–12 (1976).
Ruettinger et al., Biochimica et Biophysica Acta, 801, p. 372–380 (1984).
M. Rautio, Farm. Aikak, 84(4), p. 143–153 (1975).
Jimenez et al., J. Indian Chem. Soc., 65, p. 725–728 (1988).
Selvi et al., Tetrahedron Lett., 38, p. 6263–6266 (1997).
Kitagawa et al., Kuromatogurafi, 15, p. 17–20 (1994).
Chemical Abstract for B2 (1981) 95:1329162.
Abstract for B1 (1978) WPI (Derwent) Acc. No. 1980–09606C/198006.

*Primary Examiner*—Peter O'Sullivan
(74) *Attorney, Agent, or Firm*—George W. Johnston; Dennis P. Tramaloni

(57) ABSTRACT

Glucokinase activating compounds of the formula

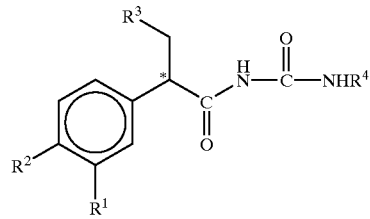

wherein $R^1$ and $R^2$ are independently hydrogen, halo, amino, nitro, cyano, sulfonamido, lower alkyl, perfluoro-lower alkyl, lower alkyl thio, perfluoro-lower alkyl thio, lower alkyl sulfonyl, or perfluoro-lower alkyl sulfonyl; $R^3$ is cycloalkyl having from 3 to 7 carbon atoms or lower alkyl having from 2 to 4 carbon atoms; $R^4$ is hydrogen, lower alkyl, lower alkenyl, hydroxy lower alkyl, halo lower alkyl,

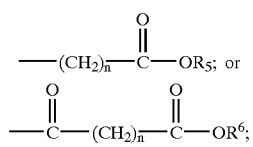

$R^5$ and $R^6$ are hydrogen or lower alkyl; and n is 0, 1, 2, 3 or 4; or a pharmaceutically acceptable salt thereof

87 Claims, No Drawings

UREA DERIVATIVES

CROSS-REFERENCE TO RELATED APPLICATIONS

This application claims priority of Provisional Applications Ser. No. 60/165,948, filed on Nov. 17, 1999, and Ser. No. 60/126,707, filed on Mar. 29, 1999, claimed under 35 U.S.C. §119(e).

BACKGROUND OF THE INVENTION

Glucokinase (GK) is one of four hexokinases that are found in mammals [Colowick, S. P., in *The Enzymes*, Vol. 9 (P. Boyer, ed.) Academic Press, New York, N.Y., pages 1–48, 1973]. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis [Chipkin, S. R., Kelly, K. L., and Ruderman, N. B. in *Joslin's Diabetes* (C. R. Khan and G. C. Wier, eds.), Lea and Febiger, Philadelphia, Pa., pages 97–115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10–15 mM) levels following a carbohydrate-containing meal [Printz, R. G., Magnuson, M. A., and Granner, D. K. in *Ann. Rev. Nutrition* Vol. 13 (R. E. Olson, D. M. Bier, and D. B. McCormick, eds.), Annual Review, Inc., Palo Alto, Calif., pages 463–496, 1993]. These findings contributed over a decade ago to the hypothesis that GK functions as a glucose sensor in β-cells and hepatocytes (Meglasson, M. D. and Matschinsky, F. M. *Amer. J. Physiol.* 246, E1–E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., *Cell* 83, 69–78, 1995; Ferrie, T., Riu, E., Bosch, F. et al., *FASEB J.*, 10, 1213–1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., *Biochem. J.* 309, 167–173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., *New England J. Med.* 338, 226–230, 1998). While mutations of the GK gene are not found in the majority of patients with type II diabetes, compounds that activate GK and, thereby, increase the sensitivity of the GK sensor system will still be useful in the treatment of the hyperglycemia characteristic of all type II diabetes. Glucokinase activators will increase the flux of glucose metabolism in β-cells and hepatocytes, which will be coupled to increased insulin secretion. Such agents would be useful for treating type II diabetes.

SUMMARY OF THE INVENTION

This invention provides a compound, comprising an amide of the formula

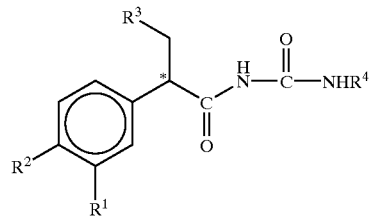

I wherein $R^1$ and $R^2$ are independently hydrogen, halo, amino, nitro, cyano, sulfonamido, lower alkyl, perfluoro-lower alkyl, lower alkyl thio, perfluoro-lower alkyl thio, lower alkyl sulfonyl, or perfluoro-lower alkyl sulfonyl; $R^3$ is cycloalkyl having from 3 to 7 carbon atoms or lower alkyl having from 2 to 4 carbon atoms; $R^4$ is hydrogen, lower alkyl, lower alkenyl, hydroxy lower alkyl, halo lower alkyl;

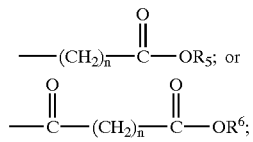

$R^5$ and $R^6$ are hydrogen or lower alkyl; and n is 0, 1, 2, 3 or 4; or a pharmaceutically acceptable salt thereof.

The compounds of formula I have been found to activate glucokinase in vitro. Glucokinase activators are useful in the treatment of type II diabetes.

DETAILED DESCRIPTION OF THE INVENTION

This invention provides a compound, comprising an amide of the formula

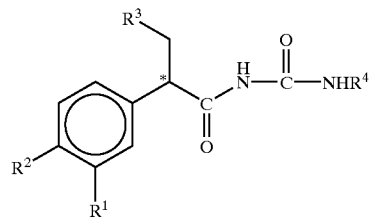

I wherein $R^1$ and $R^2$ are independently hydrogen, halo, amino, nitro, cyano, sulfonamido, lower alkyl, perfluoro-lower alkyl, lower alkyl thio, perfluoro-lower alkyl thio, lower alkyl sulfonyl, or perfluoro-lower alkyl sulfonyl; $R^3$ is cycloalkyl having from 3 to 7 carbon atoms or lower alkyl having from 2 to 4 carbon atoms; $R^4$ is hydrogen, lower alkyl, lower alkenyl, hydroxy lower alkyl, halo lower alkyl,

-continued

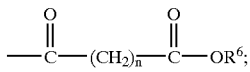

$R^5$ and $R^6$ are hydrogen or lower alkyl; and n is 0, 1, 2, 3 or 4; or a pharmaceutically acceptable salt thereof. In preferred compounds, the amide is in the "R" configuration at the asymmetric carbon shown.

In certain compounds of this invention, $R^4$ of the amide is hydrogen, lower alkyl, or lower alkenyl. Such amides are preferred when $R^3$ is cyclopentyl, especially when the amide is in the "R" configuration at the asymmetric carbon shown.

In certain amides of the above compound, $R^1$ and $R^2$ of the amide are hydrogen. Such an amide is 1-(3-cyclopentyl-2-phenyl-propionyl)-3-methyl-urea. In other of the above compounds, one of $R^1$ and $R^2$ is hydrogen and the other is cyano or halo.

Examples of Such Amides Are

1-[2-(3-chloro-phenyl)-3cyclopentyl-propionyl]-3-methyl-urea;

1-[2-(4-chloro-phenyl)-3-cyclopentyl-propionyl]-3-methyl-urea;

1-[2-(4-cyano-phenyl)-3-cyclopentyl-propionyl]-3-methyl-urea;

1-[2-(4-bromo-phenyl)-3-cyclopentyl-propionyl]-3-methyl urea.

In other amides of the above compound, $R^1$ and $R^2$ of the amide are each independently halo (preferably chloro). Examples of such amides are [3-cyclopentyl-2-(3,4-dichloro-phenyl)-propionyl]-urea;

1-[3-cyclopentyl-2-(3,4-dichloro-phenyl)-propionyl]-3-methyl-urea;

1-[3-cyclopentyl-2R)-(3,4-dichloro-phenyl)-propionyl]-3-ethyl-urea;

1-allyl-3-[3-cyclopentyl-2-(3,4-dichloro-phenyl)-proprionyl]-urea;

1-allyl-3-[3-cyclopentyl-2R)-(3,4-dichloro-phenyl)-proprionyl]-urea;

1-[3-cyclopentyl-2-(3,4-dichloro-phenyl)-propionyl]-3-ethyl-urea;

1-[3-cyclopentyl-2(R)-(3,4-dichloro-phenyl)-propionyl]-3-methyl-urea;

1-[3-cyclopentyl-2-(3,4-dichloro-phenyl)-propionyl]-3-isopropyl-urea;

1-[3-cyclopentyl-2-(3,4-dichloro-phenyl)-propionyl]-3-propyl-urea;

1-[3-cyclopentyl-2-(3,4-difluoro-phenyl)-propionyl]-3-methyl-urea.

In yet other amides of the above compound, one of $R^1$ and $R^2$ of the amide is hydrogen or halo and the other is nitro. Examples of such amides are 1-[2-(4-chloro-3-nitro-phenyl)-3-cyclopentyl-proprionyl]-3-methyl-urea.

1-[3-cyclopentyl-2-(4-nitro-phenyl)-propionyl]-3-methyl-urea.

In further amides of the above compound, one of $R^1$ and $R^2$ is hydrogen, lower alkyl thio or perfluoro-lower alkyl thio and the other is lower alkyl thio or perfluoro-lower alkyl thio. Examples of such amides are 1-[3-cyclopentyl-2-(4-trifluoromethylsulfanyl-phenyl)-propionyl]-3-methyl urea;

1-[3-cyclopentyl-2-(4-methylsulfanyl-phenyl)-propionyl]-3-methyl urea.

In yet further amides of the above compound, one of $R^1$ and $R^2$ is hydrogen or perfluoro-lower alkyl sulfonyl and the other is perfluoro-lower alkyl sulfonyl. Examples of such amides are 1-[3-cyclopentyl-2-(4-trifluoromethanesulfonyl-phenyl)-propionyl]-3-methyl urea;

1-[3-cyclopentyl-2-(3-trifluoromethanesulfonyl-phenyl)-propionyl]-3-methyl urea.

In certain amides of the above compound, at least one of $R^1$ and $R^2$ is lower alkyl sulfonyl. Preferably one of $R^1$ and $R^2$ is hydrogen or lower alkyl sulfonyl and the other is lower alkyl sulfonyl, and more preferably $R^2$ is lower alkyl sulfonyl. Examples of such amides are 1-[3-cyclopentyl-2-(4-methanesulfonyl-phenyl)-propionyl]-3-methyl urea;

1-{2-[4-(butane-1-sulfonyl)-phenyl]-3-cyclopentyl-proprionyl}-3-methyl-urea;

1-[3-cyclopentyl-2-(4-ethanesulfonyl-phenyl)-proprionyl]-3-methyl-urea;

1-[2-(3,4-bis-methanesulfonyl-phenyl)-3-cyclopentyl-proprionyl]-3-methyl-urea.

In other amides of the above compound, at least one of $R^1$ and $R^2$ is lower alkyl sulfonyl, one of $R^1$ and $R^2$ is cyano or halo and the other, preferably $R^2$, is lower alkyl sulfonyl. Examples of such amides are 1-[2-(3-bromo-4-methanesulfonyl-phenyl)-3-cyclopentyl-propionyl]-3-methyl-urea;

1-[3-cyclopentyl-2-(3-fluoro-4-methanesulfonyl-phenyl)-proprionyl]-3-methyl-urea;

1-[2-(3-chloro-4-methanesulfonyl-phenyl)-3-cyclopentyl-propionyl]-3-methyl-urea;

1-[2(R)-(3-chloro-4-methanesulfonyl-phenyl)-3-cyclopentyl-propionyl]-3-methyl-urea;

1-[2-(3-chloro-4-methanesulfonyl-phenyl)-3-cyclopentyl-propionyl]-3-ethyl-urea;

1-[2-(3-cyano-4-methanesulfonyl-phenyl)-3-cyclopentyl-propionyl]-3-methyl-urea.

In other amides of the above compound, at least one of $R^1$ and $R^2$ is lower alkyl sulfonyl, one of $R^1$ and $R^2$ is perfluoro-lower alkyl and the other, preferably $R^2$, is lower alkyl sulfonyl. Examples of such amides are 1-[3-cyclopentyl-2-(4-methanesulfonyl-3-trifluoromethyl-phenyl)-proprionyl]-3-methyl-urea.

In further amides of the above compound, at least one of $R^1$ and $R^2$ is perfluoro-lower alkyl and the other is halo. Examples of such amides are 1-[3-cyclopentyl-2-(4-fluoro-3-trifluoromethyl-phenyl)-propionyl]-3-methyl urea;

1-[3-cyclopentyl-2-(3-fluoro-4-trifluoromethyl-phenyl)-propionyl]-3-methyl urea.

In yet further amides of the above compound, at least one of $R^1$ and $R^2$ is lower alkyl sulfonyl, one of $R^1$ and $R^2$ is nitro and the other is lower alkyl sulfonyl. An example of such an amide is 1-[3-cyclopentyl-2-(4-methanesulfonyl-3-nitrophenyl)-propionyl]-3-methyl-urea.

In the compounds of this invention described above, $R^4$ of the amide is hydrogen, lower alkyl, or lower alkenyl and $R^3$ is cyclopentyl. In the compounds described below, $R^4$ is the same but $R^3$ is not cyclopentyl.

In certain such compounds, one of $R^1$ and $R^2$ is halo or hydrogen and the other is hydrogen,. An example of such an amide is [2-(4-chloro-phenyl)-4-methyl-pentanoyl]-urea. In particular $R^1$ and $R^2$ may each be chlorine. Examples of such amides are

[3-cyclopropyl-2-(3,4-dichloro-phenyl)-propionyl]-urea;

[3-cyclobutyl-2-(3,4-dichloro-phenyl)-propionyl]-urea;
R-[2-(3,4-dichloro-phenyl)-4-methyl-pentanoyl]-urea;
1-[2-(3,4-dichloro-phenyl)-4-methyl-pentanoyl]-3-methyl-urea;
1-[2-(3,4-dichloro-phenyl)-hexanoyl]-3-methyl-urea.

In other such compounds, $R^4$ is as described above and $R^3$ is cyclohexyl. In some such amides, one of $R^1$ and $R^2$ is halo or hydrogen and the other is halo. Examples of such amides are 3-[cyclohexyl-2-(3,4-dichloro-phenyl)-propionyl]-urea;
[3-cyclohexyl-2-(3,4-dichloro-phenyl)-propionyl]-3-methyl-urea.

In other such compounds, $R^4$ is as described above and $R^3$ is cycloheptyl. In some such amides, one of $R^1$ and $R^2$ is halo or hydrogen and the other is halo. An example of such an amide is [3-cycloheptyl-2-(3,4-dichloro-phenyl)-propionyl]-urea.

In certain compounds of this invention, $R^4$ is

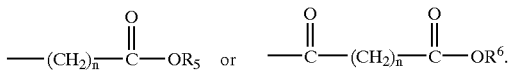

In some such compounds, $R^3$ of the amide is cyclopentyl. Preferably $R^1$ and $R^2$ are independently halo.

Examples of the Above Amides Are

3-{3-[3-cyclopentyl-2-(3,4-dichloro-phenyl)-propionyl]-ureido}-propionic acid ethyl ester;
{3-[3-cyclopentyl-2-(3,4-dichloro-phenyl)-propionyl]-ureido}-acetic acid ethyl ester;
{3-[3-cyclopentyl-2-(3,4-dichloro-phenyl)-propionyl]-ureido}-acetic acid methyl ester;
3-{3-[3-cyclopentyl-2-(3,4-dichloro-phenyl)-propionyl]-ureido}-propionic acid methyl ester;
{3-[3-cyclopentyl-2(R)-(3,4-dichloro-phenyl)-propionyl]-ureido}-acetic acid ethyl ester;
3-{3-[3-cyclopentyl-2-(3,4-dichloro-phenyl)-propionyl]-ureido}-3-oxo-propionic acid ethyl ester.

In certain compounds of this invention, $R^4$ is hydroxy lower alkyl, or halo lower alkyl. In some such compounds, $R^3$ of the amide is cyclopentyl. Preferably $R^1$ and $R^2$ are independently halo, and in addition the amide is in the "R" configuration at the asymmetric carbon shown.

Examples of the Above Amides Are

1-[3-cyclopentyl-2-(3,4-dichloro-phenyl)-proprionyl]-3-(2-hydroxy-ethyl)-urea;
1-[3-cyclopentyl-2-(3,4-dichloro-phenyl)-proprionyl]-3-(2-hydroxy-propyl)-urea;
1-[3-cyclopentyl-2-(3,4-dichloro-phenyl)-proprionyl]-3-(3-hydroxy-propyl)-urea;
1-[3-cyclopentyl-2(R)-(3,4-dichloro-phenyl)-propionyl]-3-(2-hydroxy-propyl)-urea;
1-(2-chloro-ethyl)-3-[3-cyclopentyl-2-(3,4-dichloro-phenyl)-proprionyl]-urea;
1-[3-cyclopentyl-2(R)-(3,4-dichloro-phenyl)-proprionyl]-3-(3-hydroxy-propyl)-urea.

In the compound of formula I, the * indicates the asymmetric carbon. The compound of formula I may be present either as a racemate or in the "R" configuration at the asymmetric carbon shown. The "R" enantiomers are preferred.

As used herein, the term "halogen" and the term "halo", unless otherwise stated, designate all four halogens, i.e. fluorine, chlorine, bromine and iodine. A preferred halogen is chlorine As used throughout this application, the term "lower alkyl" includes both straight chain and branched chain alkyl groups having from 1 to 7 carbon atoms, such as methyl, ethyl, propyl, isopropyl, preferably methyl and ethyl. With regard to $R^3$, isopropyl and n-propyl are preferred. "Halo lower alkyl" as used herein designates a lower alkyl group wherein one of the hydrogens is replaced by a halogen as defined above, which replacement can be at any site on the lower alkyl, including the end. A preferred halo lower alkyl group is chloroethyl. Similarly, "hydroxy lower alkyl" designates a lower alkyl group where one of the hydrogens is replaced by a hydroxy, at any site including the end. Preferred hydroxy lower alkyl groups include ethanol, isopropanol, and n-propanol. As used herein, "perfluoro-lower alkyl" means any lower alkyl group wherein all of the hydrogens of the lower alkyl group are substituted or replaced by fluoro. Among the preferred perfluoro-lower alkyl groups are trifluoromethyl, pentafluoroethyl, heptafluoropropyl, etc.

As used herein, "lower alkyl thio" means a lower alkyl group as defined above where a thio group is bound to the rest of the molecule. Similarly "perfluoro-lower alkyl" thio means a perfluoro-lower alkyl group as defined above where a thio group is bound to the rest of the molecule.

As used herein, "lower alkyl sulfonyl" means a lower alkyl group as defined above where a sulfonyl group is bound to the rest of the molecule. Similarly "perfluoro-lower alkyl sulfonyl" means a perfluoro-lower alkyl group as defined above where a sulfonyl group is bound to the rest of the molecule.

As used herein, "cycloalkyl" means a saturated hydrocarbon ring having from 3 to 10 carbon atoms, preferably from 3 to 7 carbon atoms. A preferred cycloalkyl is cyclopentyl.

As used herein, the term "lower alkenyl" denotes an alkylene group having from 2 to 6 carbon atoms with a double bond located between any two adjacent carbons of the group. Preferred lower alkenyl groups are allyl and crotyl.

As used herein, the term "lower alkoxy" includes both straight chain and branched chain alkoxy groups having from 1 to 7 carbon atoms, such as methoxy, ethoxy, propoxy, isopropoxy, preferably methoxy and ethoxy.

During the course of the reaction the various functional groups such as the free carboxylic acid or hydroxy groups will be protected via conventional hydrolyzable ester or ether protecting groups. As used herein the term "hydrolyzable ester or ether protecting groups" designates any ester or ether conventionally used for protecting carboxylic acids or alcohols which can be hydrolyzed to yield the respective hydroxyl or carboxyl group. Exemplary ester groups useful for those purposes are those in which the acyl moieties are derived from a lower alkanoic, aryl lower alkanoic, or lower alkane dicarboxcyclic acid. Among the activated acids which can be utilized to form such groups are acid anhydrides, acid halides, preferably acid chlorides or acid bromides derived from aryl or lower alkanoic acids. Example of anhydrides are anhydrides derived from monocarboxylic acid such as acetic anhydride, benzoic acid anhydride, and lower alkane dicarboxcyclic acid anhydrides, e.g. succinic anhydride as well as chloro formates e.g. trichloro, ethylchloro formate being preferred. A suitable ether protecting group for alcohols are, for example, the tetrahydropyranyl ethers such as 4-methoxy-5,6-dihydroxy-2H-pyranyl ethers. Others are aroylmethylethers such as benzyl, benzhydryl or trityl ethers or α-lower alkoxy lower alkyl ethers, for example, methoxymethyl or allylic ethers or alkyl silylethers such as trimethylsilylether.

The term "amino protecting group" designates any conventional amino protecting group which can be cleaved to yield the free amino group. The preferred protecting groups are the conventional amino protecting groups utilized in peptide synthesis. Especially preferred are those amino protecting groups which are cleavable under mildly acidic conditions from about pH 2.0 to 3. Particularly preferred amino protecting groups are t-butoxycarbonyl (BOC), carbobenzyloxy (CBZ), and 9-fluorenylmethoxycarbonyl (FMOC).

The term "pharmaceutically acceptable salts" as used herein include any salt with both inorganic or organic pharmaceutically acceptable acids such as hydrochloric acid, hydrobromic acid, nitric acid, sulfuric acid, phosphoric acid, citric acid, formic acid, maleic acid, acetic acid, succinic acid, tartaric acid, methanesulfonic acid, para-toluene sulfonic acid and the like. The term "pharmaceutically acceptable salts" also includes any pharmaceutically acceptable base salt such as amine salts, trialkyl amine salts and the like. Such salts can be formed quite readily by those skilled in the art using standard techniques.

The compound of formula I can be prepared starting from the compound of formula V by the following Reaction Scheme:

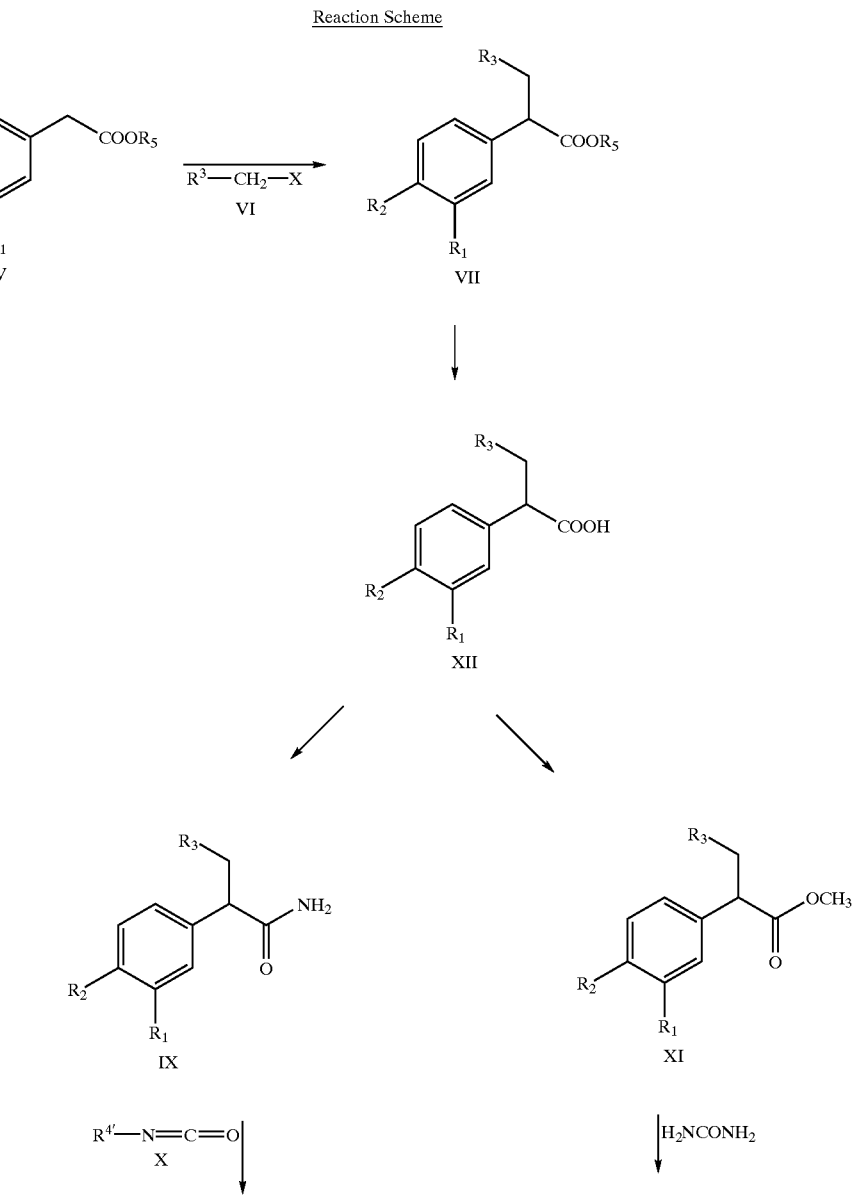

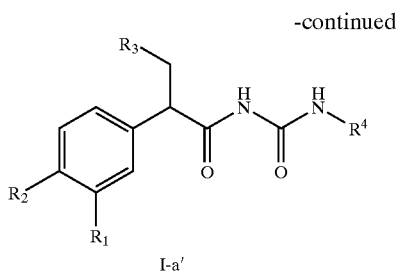

I-a'

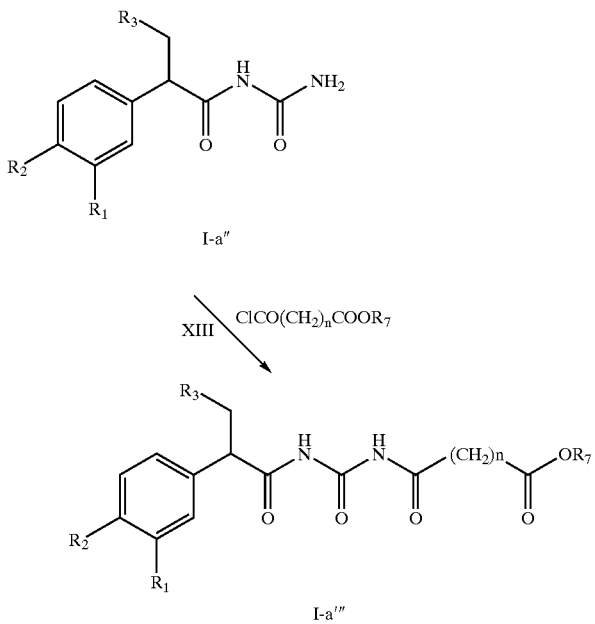

wherein $R^1$, $R^2$ and $R^3$ are as above and $R^4$ is lower alkyl, lower alkenyl, halo lower alkyl, hydroxy lower alkyl, or —$CH_2)_n$—$COOR^5$ and $R^5$ is hydrogen or lower alkyl, In the compounds of formula V wherein one of $R^1$ and $R^2$ is nitro, amino, chloro, bromo, or iodo and the other is hydrogen, the corresponding carboxylic acids or their lower alkyl esters are commercially available. In cases where only the carboxylic acids are available, they can be converted to the corresponding esters of lower alkyl alcohols using any conventional esterification methods. All the reactions hereto forward are to be carried out on lower alkyl esters of the compounds of formula V. The amino substituted compounds of formula V can be diazotized to yield the corresponding diazonium compound, which in situ can be reacted with the desired lower alkyl thiol, perfluoro-lower alkyl thiol (see for example, Baleja, J. D. Synth. Comm. 1984, 14, 215; Giam, C. S.; Kikukawa, K., J. Chem. Soc, Chem. Comm. 1980, 756; Kau, D.; Krushniski, J. H.; Robertson, D. W, J. Labelled Compd Rad. 1985, 22, 1045; Oade, S.; Shinhama, K.; Kim, Y. H., Bull Chem Soc. Jpn. 1980, 53, 2023; Baker, B. R.; et al, J. Org. Chem. 1952, 17, 164), or alkaline earth metal cyanide, to yield corresponding compounds of formula V, where one of the substituents is lower alkyl thio, perfluoro-lower alkyl thio, or cyano, and the other is hydrogen. If desired, the lower alkyl thio or perfluoro-lower alkyl thio compounds can then be converted to the corresponding lower alkyl sulfonyl or perfluoro-lower alkyl sulfonyl substituted compounds of formula V. Any conventional method of oxidizing alkyl thio substituents to sulfones can be utilized to effect this conversion.

If it is desired to produce compounds of lower alkyl or perfluoro-lower alkyl groups of compounds of formula V, the corresponding halo substituted compounds of formula V can be used as starting materials. Any conventional method of converting an aromatic halo group to the corresponding alkyl group (see for example, Katayama, T.; Umeno, M., Chem. Lett. 1991, 2073; Reddy, G. S.; Tam., Organometallics, 1984, 3, 630; Novak, J.; Salemink, C. A., Synthesis, 1983, 7, 597; Eapen, K. C.; Dua, S. S.; Tamboroski, C., J. Org Chem. 1984, 49, 478; Chen, Q, -Y.; Duan, J. -X. J. Chem. Soc. Chem. Comm. 1993, 1389; Clark, J. H.; McClinton, M. A.; Jone, C. W.; Landon, P.; Bisohp, D.; Blade, R. J., Tetrahedron Lett. 1989, 2133; Powell, R. L.; Heaton, C. A, U.S. Pat. No. 5,113,013) can be utilized to effect this conversion.

In the compounds of formula V wherein both of $R^1$ and $R^2$ are chloro or fluoro, the corresponding carboxylic acids or their lower alkyl esters are commercially available. In cases where only the carboxylic acids are available, they can converted to the corresponding esters of lower alkyl alcohols using any conventional esterification method. To produce the compound of formula V where both $R^1$ and $R^2$ are nitro, 3,4-dinitrotoluene can be used as starting material. This can be converted to the corresponding 3,4-dinitrophenyl acetic acid. Any conventional method of converting an aryl methyl group to the corresponding aryl acetic acid can be utilized to effect this conversion (see for example, Clark, R. D.; Muchowski, J. M.; Fisher, L. E.; Flippin, L. A.; Repke, D. B.; Souchet, M, Synthesis, 1991, 871).

The compounds of formula V where both $R^1$ and $R^2$ substituents are amino can be obtained from the corresponding dinitro compound of formula V, described above. Any conventional method of reducing a nitro group to an amine can be utilized to effect this conversion. The compound of formula V where both $R^1$ and $R^2$ are amine groups can be used to prepare the corresponding compound of formula V where both $R^1$ and $R^2$ are iodine or bromo via the diazotization reaction described before. Any conventional method of converting amino group to an iodo or bromo group (see for example , Lucas, H. J.; Kennedy, E. R. Org. Synth. Coll. Vol, II 1943, 351) can be utilized to effect this conversion.

If it is desired to produce compounds of formula V, where both $R^1$ and $R^2$ are lower alkyl thio or perfluoro-lower alkyl thio groups, the compound of formula V where $R^1$ and $R^2$ are amino can be used as starting material. Any conventional method of converting aryl amino group to aryl thioalkyl group can be utilized to effect this conversion. If it is desired to produce compounds of formula V where $R^1$ and $R^2$ are lower alkyl sulfonyl or perfluoro-lower alkyl sulfonyl, the corresponding compounds of formula V where $R^1$ and $R^2$ are lower alkyl thio or perfluoro-lower alkyl thio can be used as starting material. Any conventional method of oxidizing alkyl thio substituents to sulfones can be utilized to effect this conversion.

If it is desired to produce compounds of formula V, where both $R^1$ and $R^2$ are substituted with lower alkyl or perfluoro-lower alkyl groups, the corresponding halo substituted compounds of formula V can be used as starting materials. Any conventional method of converting an aromatic halo group to the corresponding alkyl group can be utilized to effect this conversion.

If it is desired to produce compounds of formula V, where one or both of $R^1$ and $R^2$ are substituted with sulfonamido, the corresponding compounds where one or both of $R^1$ and $R^2$ are substituted with nitro can be used as starting materials. Any standard method of converting a nitrophenyl compound to the corresponding sulfonamidophenyl compound can be used to effect this conversion.

The carboxylic acids corresponding to the compounds of formula V where one of $R^1$ and $R^2$ is nitro and the other is halo (for example chloro) are known from the literature (see for 4-chloro-3-nitrophenyl acetic acid, Tadayuki, S.; Hiroki, M.; Shinji, U.; Mitsuhiro, S. Japanese patent, JP 71-99504, *Chemical Abstracts* 80:59716; see for 4-nitro-3-chlorophenyl acetic acid, Zhu, J.; Beugelmans, R.; Bourdet, S.; Chastanet, J.; Rousssi, G. *J. Org. Chem.* 1995, 60, 6389; Beugelmans, R.; Bourdet, S.; Zhu, J. *Tetrahedron Lett.* 1995, 36, 1279). These carboxylic acids can be converted to the corresponding lower alkyl esters using any conventional esterification methods. Thus, if it is desired to produce the compound of formula V where one of $R^1$ and $R^2$ is nitro and the other is lower alkyl thio or perfluoro-lower alkyl thio, the corresponding compound where one of $R^1$ and $R^2$ is nitro and the other is chloro can be used as starting material. In this reaction, any conventional method of nucleophilic displacement of aromatic chlorine group with a lower alkyl thiol can be used (see for example, Singh, P.; Batra, M. S.; Singh, H, *J. Chem. Res. -S* 1985 (6), S204; Ono, M.; Nakamura, Y.; Sata, S.; Itoh, I, *Chem. Lett*, 1988, 1393; Wohrle, D.; Eskes, M.; Shigehara, K.; Yamada, A, *Synthesis*, 1993, 194; Sutter, M.; Kunz, W. U.S. Pat. No. ; U.S. Pat. No. 5,169,951). Once the compounds of formula V where one of $R^1$ and $R^2$ is nitro and the other is lower alkyl thio or perfluoro-lower alkyl thio are available, they can be converted to the corresponding compounds of formula V where one of $R^1$ and $R^2$ is nitro and the other is lower alkyl sulfonyl or perfluoro-lower alkyl sulfonyl using conventional oxidation procedures.

If it is desired to produce compounds of formula V where one of $R^1$ and $R^2$ is amino and the other is lower alkyl thio or perfluoro-lower alkyl thio, the corresponding compound where one of $R^1$ and $R^2$ is nitro and the other is lower alkyl thio or perfluoro-lower alkyl thio can be used as starting materials. Any conventional method of reducing an aromatic nitro group to an amine can be utilized to effect this conversion.

If it is desired to produce compounds of formula V where one of $R^1$ and $R^2$ is lower alkyl thio and the other is perfluoro-lower alkyl thio, the corresponding compound where one of $R^1$ and $R^2$ is amino and the other is lower alkyl thio or perfluoro-lower alkyl thio can be used as starting materials. Any conventional method of diazotizing aromatic amino group and reacting it in situ with the desired lower alkyl thiol can be utilized to effect this conversion.

If it is desired to produce compounds of formula V where one of $R^1$ and $R^2$ is lower alkyl sulfonyl and the other is perfluoro-lower alkyl sulfonyl, the corresponding compounds where one of $R^1$ and $R^2$ is lower alkyl thio and the other is perfluoro-lower alkyl thio, can be used as starting materials. Any conventional method of oxidizing an aromatic thio ether group to the corresponding sulfone group can be utilized to effect this conversion.

If it is desired to produce compounds of formula V where one of $R^1$ and $R^2$ is halo and the other is lower alkyl thio or perfluoro-lower alkyl thio, the corresponding compounds where one of $R^1$ and $R^2$ is amino and the other is lower alkyl thio or perfluoro-lower alkyl thio can be used as starting materials. Any conventional method of diazotizing an aromatic amino group and conversion of it in situ to an aromatic halide can be utilized to effect this conversion.

If it is desired to produce compounds of formula V where one of $R^1$ and $R^2$ is halo and the other is lower alkyl sulfonyl or perfluoro-lower alkyl sulfonyl, the corresponding compounds where one of $R^1$ and $R^2$ is halo and the other is lower alkyl thio or perfluoro-lower alkyl thio can be used as starting materials. Any conventional method of oxidizing an aromatic thio ether to the corresponding sulfone can be utilized to effect this conversion. If it is desired to produce compounds of various combinations of lower alkyl and perfluoro-lower alkyl groups of compounds of formula V, the corresponding halo substituted compounds of formula V can be used as starting materials. Any conventional method of converting an aromatic halo group to the corresponding alkyl group can be utilized to effect this conversion.

If one wishes to prepare the compound formula V where one of $R^1$ and $R^2$ is nitro and the other is amino, the compound of formula V where one of $R^1$ and $R^2$ is nitro and other is chloro can be used as a starting material. The chloro substituent on the phenyl ring can be converted to an iodo substituent (see for example, Bunnett, J. F.; Conner, R. M.; *Org Synth. Coll Vol* V, 1973, 478; Clark, J. H.; Jones, C. W. *J. Chem. Soc. Chem. Commun.* 1987, 1409), which in turn can be reacted with an azide transferring agent to form the corresponding azide (see for example, Suzuki, H.; Miyoshi, K.; Shinoda, M. *Bull. Chem. Soc. Jpn*, 1980, 53, 1765). This azide can then be reduced in a conventional manner to form the amine substituent by reducing it with commonly used reducing agent for converting azides to amines (see for example, Soai, K.; Yokoyama, S.; Ookawa, A. *Synthesis*, 1987, 48).

In order to prepare the compound of formula V where one of $R^1$ and $R^2$ is cyano and the other is amino, the compound of formula V where one of $R^1$ and $R^2$ is nitro and other is amino can be used as a starting material. The amino group is converted to cyano by conventional means of converting aryl-amino to aryl-cyano, for example by diazotization with a cyanide-transferring agent such as cuprous cyanide. The nitro group is converted to an amino group as described above.

If it is desired to convert commercially available compounds to compounds of formula V where one of $R^1$ and $R^2$ is cyano and the other is any other desired substituent, the compound of formula V where one of $R^1$ and $R^2$ is nitro and the other is halo is used as starting material. With this starting material, the nitro is converted to the cyano and the halo is converted to the desired $R^1$ and $R^2$ substituent. If it is desired to produce the compound of formula V where both $R^1$ and $R^2$ are cyano, this can be prepared as described hereinbefore from compounds where $R^1$ and $R^2$ are amino via diazotization and reaction with a cyanide-transferring agent such as cuprous cyanide.

In the first step of this Reaction Scheme, the alkyl halide of formula VI is reacted with the compound of formula V, to produce the compound of formula VII. In this reaction, if in the compounds of formula V, $R^1$ or $R^2$ is an amino group, such amino group(s) have to be protected before carrying out the alkylation reaction with the alkyl halide of formula VI. The amino group can be protected with any conventional acid removable group (see for example, for t-butyloxycarbonyl group see, Bodanszky, M. *Principles of Peptide Chemistry, Springer—Verlag*, New York, 1984, p 99). The protecting group has to be removed from the amino groups after preparing the corresponding amine protected compounds of formula I-a', I-a", and I-a'" to obtain the corresponding amines. The compound of formula V is an organic acid having an alpha carbon atom and the compound of formula VI is an alkyl halide so that alkylation occurs at the alpha carbon atom of this carboxylic acid. This reaction is carried out by any conventional means of alkylation of the alpha carbon atom of a lower alkyl ester of a carboxylic acid. Generally, in these alkylation reactions any alkyl halide is reacted with the anion generated from any acetic acid ester. The anion can be generated by using a strong organic base such as lithium diisopropylamide, n-butyl lithium as well as other organic lithium bases. In carrying out this reaction low boiling ether solvents are utilized such as tetrahydrofuran at low temperatures from –80° C. to about –10° C. being preferred. However any temperature from –80° C. to room temperature can be used.

The compound of formula VII can be converted to the compound of formula XII by any conventional procedure to convert a carboxylic acid ester to an acid. The carboxylic acid of the formula XII can be converted to the amide of the formula IX. This reaction is carried out by using conventional means for converting the acid of formula XII to an acid chloride and thereafter treating this acid chloride with ammonia or an ammonia-producing compound such as hexamethyl disilazane. Conditions which are conventional for converting an acid to an acid chloride can be utilized in this procedure. This acid chloride when reacted under conventional conditions with ammonia as described will produce the amide of formula IX. The compound of formula IX when reacted with an alkyl, alkenyl, or —$CH_2)_nC(O)_2R_5$ isocyanate of formula X forms the urea adduct of formula I-a'. Any conventional method of reacting alkyl, alkenyl, or —$(CH_2)_nC(O)_2R_5$ isocyanate with an amide to form a urea linkage can be utilized to form the compound of formula I-a'.

When $R^4$, is a lower alkenyl group in the compound of formula Ia', this compound can be converted to the corresponding hydroxy lower alkyl group by conventional hydroboration at the olefinic group to produce a corresponding hydroxy group. The hydroxy group, if desired, can be converted to a halo group. Any method of halogenating a hydroxy group can be used in accordance with this invention.

On the other hand, if it is desired to produce the compound of formula Ia" the compound of formula XII is first converted to the methyl ester of formula XI, thereafter reacting it with urea to produce the compound of formula I-a'. This reaction is carried out by utilizing any conventional means of reacting a methyl ester with urea to form the corresponding condensation product.

The compound of formula I where $R^4$ is $CO(CH_2)_n$ $COOR^6$ is produced from the monoacid chloride XIII of the monoester of the corresponding dicarboxylic acid. The monoacid chloride XIII is coupled with the compounds of formula Ia" using standard coupling methods.

The compound of formula VII has an asymmetric carbon atom through which the group $CH_2R^3$ and the acid amide substituents are connected. In accordance with this invention, the preferred stereoconfiguration of this group is R.

If it is desired to produce the R or the S isomer of the compound of formula I, this compound can be separated into these isomers by any conventional chemical means. Among the preferred chemical means is to react the compound of formula XII with an optically active base. Any conventional optically active base can be utilized to carry out this resolution. Among the preferred optically active bases are the optically active amine bases such as alpha-methylbenzylamine, quinine, dehydroabietylamine and alpha-methylnaphthylamine. Any of the conventional techniques utilized in resolving organic acids with optically active organic amine bases can be utilized in carrying out this reaction.

In the resolution step, the compound of formula XII is reacted with the optically active base in an inert organic solvent medium to produce salts of the optically active amine with both the R and S isomers of the compound of formula XII. In the formation of these salts, temperatures and pressure are not critical and the salt formation can take place at room temperature and atmospheric pressure. The R and S salts can be separated by any conventional method such as fractional crystallization. After crystallization, each of the salts can be converted to the respective compounds of formula XII in the R and S configuration by hydrolysis with an acid. Among the preferred acids are dilute aqueous acids, i.e., from about 0.001N to 2N aqueous acids, such as aqueous sulfuric or aqueous hydrochloric acid. The configuration of formula XII which is produced by this method of resolution is carried out throughout the entire reaction scheme to produce the desired R or S isomer of formula I. The separation of R and S isomers can also be achieved using an enzymatic ester hydrolysis of any lower alkyl esters corresponding to the compound of the formula XII (see for example, Ahmar, M.; Girard, C.; Bloch, R, *Tetrahedron Lett*, 1989, 7053), which results in the formation of corresponding chiral acid and chiral ester. The ester and the acid can be separated by any conventional method of separating an acid from an ester. The preferred method of resolution of racemates of the compounds of the formula XII is via the formation of corresponding diastereomeric esters or amnides. These diastereomerie esters or amnides can be prepared by coupling the carboxylic acids of the formula XII with a chiral alcohol, or a chiral amine. This reaction can be carried out using any conventional method of coupling a carboxylic acid with an alcohol or an amine. The corresponding diastereomers of compounds of the formula XII can then be separated using any conventional separation methods. The resulting pure diastereomeric esters or amides can then be hydrolyzed to yield the corresponding pure R or S isomers. The hydrolysis reaction can be carried out using any conventional method to hydrolyze an ester or an amide without racemization.

The following compounds were found to have in vivo activity when administered orally in accordance with the assay described in Example B:

1-[3-cyclopentyl-2(R)-(3,4-dichloro-phenyl)-propionyl-3-ethyl-urea;

1-[3-cyclopentyl-2(R)-(3,4-dichloro-phenyl)-propionyl]-3-methyl-urea;

1-[3-cyclopentyl-2-(3,4-dichloro-phenyl)-propionyl]-3-methyl urea;

1-[3-cyclopentyl-2-(4-methanesulfonyl-phenyl)-propionyl]-3-methyl urea;

1-Allyl-3-[3-cyclopentyl-2(R)-(3,4-dichloro-phenyl)-propionyl]-urea;

1-[2-(3-Chloro-4-methanesulfonyl-phenyl)-3-cyclopentyl-propionyl]-3-methyl-urea;

1-[2(R)-(3-Chloro-4-methanesulfonyl-phenyl)-3-cyclopentyl-propionyl]-3-methyl-urea;

1-[2-(3-Bromo-4-methanesulfonyl-phenyl)-3-cyclopentyl-propionyl]3-methyl-urea

All of the compounds described in the following syntheses activated glucokinase in vitro in accordance with the assay described in Example A.

This invention will be better understood from the following examples, which are for purposes of illustration and are not intended to limit the invention defined in the claims that follow thereafter.

SYNTHESIS EXAMPLES

Example 1

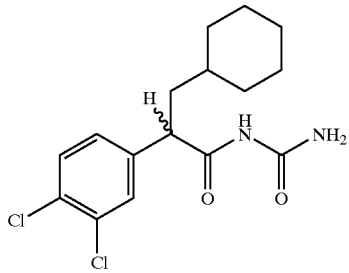

(A) 3-Cyclohexyl-2-(3,4-dichloro-phenyl)-propionyl]-urea

A solution of (3,4-dichloro-phenyl)-acetic acid (14.0 g, 0.068 mol) in methanol (71 mL) was treated with a catalytic amount of sulfuric acid. The reaction mixture was refluxed for 12 h. The reaction was concentrated in vacuo. Flash chromatography (Merck Silica gel 60, 230–400 mesh, 50/50 hexanes/ethyl acetate) afforded (3,4-dichloro-phenyl)-acetic acid methyl ester (15.0 g, quant.) as a white solid: mp 30–32° C.; EI-HRMS m/e calcd for $C_9H_8Cl_2O_2$ ($M^+$) 217.9901, found 217.9907.

A solution of freshly prepared lithium diisopropylamide (16.3 mL of a 0.31 M stock solution, 5.04 mmol) cooled to −78° C. was treated with (3,4-dichloro-phenyl)-acetic acid methyl ester (1.0 g, 4.58 mmol) in tetrahydrofuran/hexamethylphosphoramide (8.6 mL, 3:1). The resulting solution was stirred at −78° C. for 45 min. At this time, the reaction was treated with a solution of bromomethylcyclohexane (1.92 mL, 13.76 mmol) in hexamethylphosphoramide (1 mL). The reaction mixture was stirred at −78° C. for 3 h. The reaction was warmed to 25° C. and stirred at 25° C. for 16 h. The reaction mixture was then quenched by the dropwise addition of a saturated aqueous ammonium chloride solution (20 mL). This mixture was poured into water (100 mL) and extracted with ethyl acetate (3×50 mL). The organics were dried over sodium sulfate, filtered, and concentrated in vacuo. Flash chromatography (Merck Silica gel 60, 230–400 mesh, 75/25 hexanes/ethyl acetate) afforded 3-cyclohexyl-2-(3,4-dichloro-phenyl)-propionic acid methyl ester (1.5 g, quant.) as a clear oil: EI-HRMS m/e calcd for $C_{16}H_{20}Cl_2O_2$ ($M^+$) 314.0840, found 314.0836.

A mixture of 3-cyclohexyl-2-(3,4-dichloro-phenyl)-propionic acid methyl ester (582 mg, 1.84 mmol) and urea (222 mg, 3.69 mmol) in a solution of magnesium methoxide in methanol (7.4 wt %, 3.96 mL, 2.76 mmol) was refluxed at 120° C. for 12 h. The reaction mixture was then concentrated in vacuo. Flash chromatography (Merck Silica gel 60, 230–400 mesh, 50/50 hexanes/ethyl acetate) afforded 3-cyclohexyl-2-(3,4-dichloro-phenyl)-propionyl]-urea (52.9 mg, 8.3%) as a white solid: mp 76–79° C.; EI-HRMS m/e calcd for $C_{16}H_{20}Cl_2N_2O_2$ ($M^+$) 342.0902, found 342.0904.

(B) In an Analogous Manner, There Were Obtained:

(a) From 3-cyclopropyl-2-(3,4-dichloro-phenyl)-propionic acid methyl ester and urea: [3-Cyclopropyl-2-(3,4-dichloro-phenyl)-propionyl]-urea as a white solid: mp 117–119° C.; EI-HRMS m/e calcd for $C_{13}H_{14}Cl_2N_2O_2$ ($M^+$) 300.0432, found 300.0431.

(b) From 3-cyclopentyl-2-(3,4-dichloro-phenyl)-propionic acid methyl ester and urea: [3-Cyclopentyl-2-(3,4-dichloro-phenyl)-propionyl]-urea as a white solid: mp 103–105° C.; EI-HRMS m/e calcd for $C_{15}H_{18}Cl_2N_2O_2$ ($M^+$) 328.0745, found 328.0750.

(c) From 3-cyclobutyl-2-(3,4-dichloro-phenyl)-propionic acid methyl ester and urea: [3-Cyclobutyl-2-(3,4-dichloro-phenyl)-propionyl]-urea as a white solid: mp 65–67° C.; EI-HRMS m/e calcd for $C_{14}H_{16}Cl_2N_2O_2$ ($M^+$) 314.0589, found 314.0597.

(d) From 3-cycloheptyl-2-(3,4-dichloro-phenyl)-propionic acid methyl ester and urea: [3-Cycloheptyl-2-(3,4-dichloro-phenyl)-propionyl]-urea as a white solid: mp 69–71° C.; EI-HRMS m/e calcd for $C_{17}H_{22}Cl_2N_2O_2$ ($M^+$) 356.1058, found 356.1054.

(e) From 1-[3-cyclopentyl-2-(3,4-dichloro-phenyl)-propionyl]-3-methyl ester and methyl urea: 1-[3-Cyclopentyl-2-(3,4-dichloro-phenyl)-propionyl]-3-methyl-urea as a white solid: mp 120–125° C.; EI-HRMS m/e calcd for $C_{16}H_{20}Cl_2N_2O_2$ ($M^+$) 342.0902, found 342.0903.

(f) From 3-cyclohexyl-2-(3,4-dichloro-phenyl)-propionic acid methyl ester and methyl urea: [3-Cyclohexyl-2-(3,4-dichloro-phenyl)-propionyl]-3-methyl-urea as a white solid: mp 69–73° C.; EI-HRMS m/e calcd for $C_{17}H_{22}Cl_2N_2O_2$ ($M^+$) 356.1058, found 356.1046

(g) From 1-[2-(3,4-dichloro-phenyl)-4-methyl-pentanoyl]-3-methyl ester and methyl-urea: 1-[2-(3,4-Dichloro-phenyl)-4-methyl-pentanoyl]-3-methyl-urea as a white solid: mp 123–125° C.; EI-HRMS m/e calcd for $C_{14}H_{18}Cl_2N_2O_2$ ($M^+$) 316.0745, found 316.0740.

(h) From 2-(3,4-dichloro-phenyl)-hexanoic acid methyl ester and methyl-urea: 1-[2-(3,4-Dichloro-phenyl)-hexanoyl]-3-methyl-urea as a clear oil: EI-HRMS m/e calcd for $C_{14}H_{18}Cl_2N_2O_2$ ($M^+$) 316.0743, found 316.0745.

Example 2

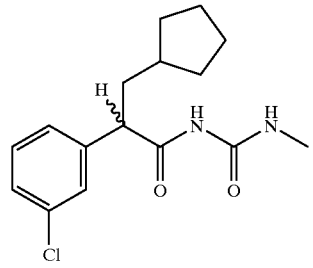

1-[2-(3-Chloro-phenyl)-3-cyclopentyl-propionyl]-3-methyl-urea (3-Chloro-phenyl)-acetic acid (6.03 g, 0.03 mol) was dissolved in ethanol (37.7 mL) and treated with a catalytic amount of sulfuric acid. The reaction mixture was refluxed for 12 h. The reaction was concentrated in vacuo. Flash chromatography (Merck Silica gel 60, 230–400 mesh, 50/50 hexanes/ethyl acetate) afforded (3-chloro-phenyl)-acetic acid ethyl ester (6.10 g, 86.8%) as a clear oil: EI-HRMS m/e calcd for $C_{10}H_{11}ClO_2$ ($M^+$) 198.0448, found 198.0442.

A solution of freshly prepared lithium diisopropylamide (23 mL of 0.31 M stock solution, 7.13 mmol) cooled to −78° C. was treated with (3-chloro-phenyl)-acetic acid ethyl ester (1.28 g, 6.48 mmol) in tetrahydrofuran/ hexamethylphosphoramide (16.1 mL, 3:1). The resulting solution was stirred at −78° C. for 45 min. At this time, the reaction was treated with a solution of iodomethylcyclopentane (1.50 g, 7.13 mmol) in hexamethylphosphoramide (1 mL). The reaction mixture was stirred at −78° C. for 4 h. The reaction was warmed to 25° C. and stirred at 25° C. for 16 h. The reaction mixture was then quenched by the dropwise addition of a saturated aqueous ammonium chloride solution (20 mL). This mixture was poured into water (100 mL) and extracted with ethyl acetate (3×50 mL). The organics were dried over sodium sulfate, filtered, and concentrated in vacuo. Flash chromatography (Merck Silica gel 60, 230–400 mesh, 75/25 hexanes/ethyl acetate) afforded 2-(3-chloro-phenyl)-3-cyclopentyl-propionic acid ethyl ester (1.70 g, 93%) as a yellow oil: EI-HRMS m/e calcd for $C_{16}H_{21}ClO_2$ ($M^+$) 280.1230, found 280.1238.

A mixture of 2-(3-chloro-phenyl)-3-cyclopentyl-propionic acid ethyl ester (1.70 g, 6.05 mmol) and methyl urea (673 mg, 9.08 mmol) in a solution of magnesium methoxide in methanol (7.4 wt %, 17.3 mL, 12.1 mmol) was refluxed at 100° C. for 6 h. The reaction mixture was then concentrated in vacuo. Flash chromatography (Merck Silica gel 60, 230–400 mesh, 75/25 hexanes/ethyl acetate) afforded 1-[2-(3-chloro-phenyl)-3-cyclopentyl-propionyl]-3-methyl-urea (149.1 mg, 8%) as a white solid: mp 52–55° C.; EI-HRMS m/e calcd for $C_{16}H_{21}ClN_2O_2$ ($M^+$) 308.1292, found 308.1287.

Example 3

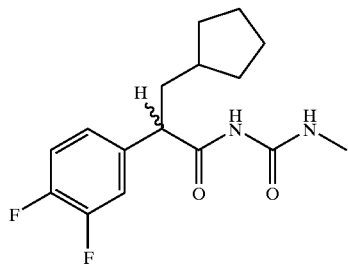

1-[3-Cyclopentyl-2-(3,4-difluoro-phenyl)-propionyl]-3-methyl-urea

A solution of (3,4-difluoro-phenyl)-acetic acid (5.0 g, 0.029 mol) in methanol (30.0 mL) was treated with a catalytic amount of sulfuric acid. The reaction mixture was refluxed for 4 h. The reaction was concentrated in vacuo. Flash chromatography (Merck Silica gel 60, 230–400 mesh, 50/50 hexanes/ethyl acetate) afforded (3,4-difluoro-phenyl)-acetic acid methyl ester (5.15 g, 95.2%) as a clear oil: EI-HRMS m/e calcd for $C_9H_8F_2O_2$ ($M^+$) 186.0493, found 186.0492.

A solution of freshly prepared lithium diisopropylamide (23.0 mL of a 0.31M stock solution, 7.13 mmol) cooled to −78° C. was treated with (3,4-difluoro-phenyl)-acetic acid methyl ester (1.20 g, 6.48 mmol) in tetrahydrofuran/hexamethylphosphoramide (16.1 mL, 3:1). The resulting solution was stirred at −78° C. for 45 min. At this time, the reaction was treated with a solution of iodomethylcyclopentane (1.50 g, 7.13 mmol) in hexamethylphosphoramide (1 mL). The reaction mixture was stirred at −78° C. for 4 h. The reaction was then warmed to 25° C. and was stirred at 25° C. for 16 h. The reaction mixture was then quenched by the dropwise addition of a saturated aqueous ammonium chloride solution (20 mL). This mixture was poured into water (100 mL) and extracted with ethyl acetate (3×50 mL). The organics were dried over sodium sulfate, filtered, and concentrated in vacuo. Flash chromatography (Merck Silica gel 60, 230–400 mesh, 75/25 hexanes/ethyl acetate) afforded 3-cyclopentyl-2-(3,4-difluoro-phenyl)-propionic acid methyl ester (1.79 g, quant.) as a clear oil: EI-HRMS m/e calcd for $C_{15}H_{18}F_2O_2$ ($M^+$) 268.1275, found 268.1278.

A mixture of 3-cyclopentyl-2-(3,4-difluoro-phenyl)-propionic acid methyl ester (1.65 g, 6.14 mmol) and methyl urea (683 mg, 9.22 mmol) in a solution of magnesium methoxide in methanol (7.4 wt %, 16.6 mL, 12.3 mmol) was refluxed at 100° C. for 8 h. The reaction mixture was then concentrated in vacuo. Flash chromatography (Merck Silica gel 60, 230–400 mesh, 75/25 hexanes/ethyl acetate) afforded 1-[3-cyclopentyl-2-(3,4-difluoro-phenyl)-propionyl]-3-methyl-urea (180 mg, 9.4%) as a white solid: mp 111–113° C.; EI-HRMS m/e calcd for $C_{16}H_{20}F_2N_2O_2$ ($M^+$) 310.1493, found 310.1499.

Example 4

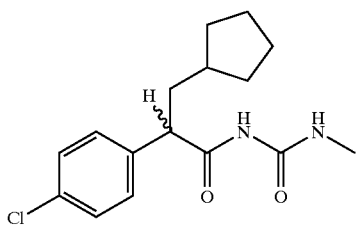

1-[2-(4-Chloro-phenyl)-3-cyclopentyl-propionyl]-3-methyl-urea

A solution of (4-chloro-phenyl)-acetic acid (6.29 g, 0.03 mol) in ethanol (38.4 mL) was treated with a catalytic amount of sulfuric acid. The reaction mixture was refluxed for 12 h. The reaction was then concentrated in vacuo. Flash chromatography (Merck Silica gel 60, 230–400 mesh, 50/50 hexanes/ethyl acetate) afforded (4-chloro-phenyl)-acetic acid ethyl ester (6.45 g, 88%) as a pale yellow solid: mp 39–41° C.; EI-HRMS m/e calcd for $C_{10}H_{11}ClO_2$ ($M^+$) 198.0448, found 198.0452.

A solution of freshly prepared lithium diisopropylamide (23.0 mL of 0.31M stock solution, 7.13 mmol) cooled to −78° C. was treated with (4-chloro-phenyl)-acetic acid ethyl ester (1.28 g, 6.48 mmol) in tetrahydrofuran/hexamethylphosphoramide (16.1 mL, 3:1). The resulting solution was stirred at −78° C. for 45 min. At this time, the reaction was treated with a solution of iodomethylcyclopentane (1.50 mg, 7.13 mmol) in hexamethylphosphoramide (1 mL). The reaction mixture was stirred at −78° C. for 4 h. The reaction was warmed to 25° C. and stirred at 25° C. for 16 h. The reaction mixture was then quenched by the dropwise addition of a saturated aqueous ammonium chloride solution (20 mL). This mixture was poured into water (100 mL) and extracted with ethyl acetate (3×50 mL). The organics were dried over sodium sulfate, filtered, and concentrated in vacuo. Flash chromatography (Merck Silica gel 60, 230–400 mesh, 75/25 hexanes/ethyl acetate) afforded 2-(4-chloro-phenyl)-3-cyclopentyl-propionic acid ethyl ester (1.65 g, 90.9%) as a yellow oil: EI-HRMS m/e calcd for $C_{16}H_{21}Cl_2O_2$ ($M^+$) 280.1230, found 280.1227.

A mixture of 2-(4-chloro-phenyl)-3-cyclopentyl-propionic acid ethyl ester (1.65 g, 5.89 mmol) and methyl urea (654 mg, 8.83 mmol) in a solution of magnesium methoxide in methanol (7.4 wt %, 16.9 mL, 11.78 mmol) was refluxed at 100° C. for 6 h. The reaction mixture was then concentrated in vacuo. Flash chromatography (Merck Silica gel 60, 230–400 mesh, 75/25 hexanes/ethyl acetate)

afforded 1-[2-(4-chloro-phenyl)-3-cyclopentyl-propionyl]-3-methyl-urea (105.3 mg, 5.8%) as a white solid: mp 145–147° C.; EI-HRMS m/e calcd for $C_{16}H_{21}ClN_2O_2$ (M$^+$) 308.1292, found 308.1291.

Example 5

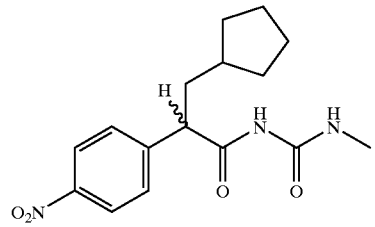

1-[3-Cyclopentyl-2-(4-nitro-phenyl)-propionyl]-3-methyl-urea

A solution of freshly prepared lithium diisopropylamide (430.55 mL of a 0.3M stock solution, 129.16 mmol) cooled to −78° C. was treated with (4-nitro-phenyl)-acetic acid ethyl ester (26.32 g, 125.83 mmol) in tetrahydrofuran/hexamethylphosphoramide (312.5 mL, 3:1). The resulting solution was stirred at −78° C. for 45 min. At this time, the reaction was treated with a solution of iodomethylcyclopentane (27.75 g, 132.1 mmol) in hexamethylphosphoramide (27.8 mL). The mixture was stirred at −78° C. for 4 h. The reaction was then warmed to 25° C. and was stirred at 25° C. for 16 h. The reaction mixture was then quenched by the dropwise addition of a saturated aqueous ammonium chloride solution (250 mL). The reaction mixture was concentrated in vacuo. The residue was diluted with water (250 mL) and extracted with ethyl acetate (3×300 mL). The organics were washed with a saturated aqueous lithium chloride solution (2×250 mL), dried over magnesium sulfate, filtered, and concentrated in vacuo. Flash chromatography (Merck Silica gel 60, 230–400 mesh, 95/5 hexanes/ethyl acetate) afforded 3-cyclopentyl-2-(4-nitro-phenyl)-propionic acid ethyl ester (28.30 g, 77.2%) as a yellow oil: EI-HRMS m/e calcd for $C_{16}H_{21}N_3O_4$(M$^+$) 291.1470, found 291.1470.

A mixture of 3-cyclopentyl-2-(4-nitro-phenyl)-propionic acid ethyl ester (1.27 g, 4.36 mmol) and methyl urea (647 mg, 8.73 mmol) in a solution of magnesium methoxide in methanol (7.4 wt %, 9.36 mL, 6.54 mmol) was refluxed at 100° C. for 8.5 h. The reaction mixture was then concentrated in vacuo. Flash chromatography (Merck Silica gel 60, 230–400 mesh, 50/50 hexanes/ethyl acetate) afforded 1-[3-cyclopentyl-2-(4-nitro-phenyl)-propionyl]-3-methyl-urea (183.6 mg, 13.2%) as a white solid: mp 179–183° C.; EI-HRMS m/e calcd for $C_{16}H_{21}N_3O_4$(M$^+$) 319.1532, found 319.1527.

Example 6

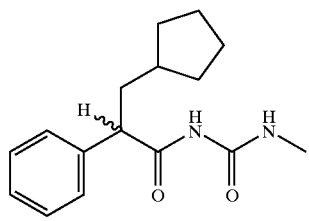

1-(3-Cyclopentyl-2-phenyl-propionyl)-3-methyl-urea

A solution of freshly prepared lithium diisopropylamide (23 mL of a 0.31 M stock solution, 7.13 mmol) cooled to −78° C. was treated with phenyl-acetic acid ethyl ester (1.06 g, 6.48 mmol) in tetrahydrofuran/hexamethylphosphoramide (16.1 mL, 3:1). The resulting solution was stirred at −78° C. for 45 min. At this time, the reaction was treated with a solution of iodomethylcyclopentane (1.50 g, 7.14 mmol) in hexamethylphosphoramide (1.5 mL). The mixture was stirred at −78° C. for 4 h. The reaction was then warmed to 25° C. and was stirred at 25° C. for 48 h. The reaction mixture was then quenched by the dropwise addition of a saturated aqueous ammonium chloride solution (5 mL). The reaction mixture was poured into water (100 mL) and extracted with ethyl acetate (2×100 mL). The organics were washed with a saturated aqueous lithium chloride solution (2×50 mL), dried over magnesium sulfate, filtered, and concentrated in vacuo. Flash chromatography (Merck Silica gel 60, 230–400 mesh, 95/5 hexanes/ethyl acetate) afforded 3-cyclopentyl-2-phenyl-propionic acid ethyl ester (1.70 g, quant.) as a pale yellow oil: EI-HRMS m/e calcd for $C_{16}H_{22}O_2$ (M$^+$) 247.1698, found 247.1704.

A mixture of 3-cyclopentyl-2-phenyl-propionic acid ethyl ester (1.70 g, 7.06 mmol) and methyl urea (1.04 mg, 14.13 mmol) in a solution of magnesium methoxide in methanol (7.4 wt %, 130.3 mL, 21.18 mmol) was refluxed at 100° C. for 24 h. The reaction mixture was then concentrated in vacuo. Flash chromatography (Merck Silica gel 60, 230–400 mesh, 50/50 hexanes/ethyl acetate) afforded 1-(3-cyclopentyl-2-phenyl-propionyl)-3-methyl-urea (1.21 mg, 62.4%) as a white solid: mp 145–147° C.; EI-HRMS m/e calcd for $C_{16}H_{22}N_2O_2$ (M$^+$) 274.1681, found 274.1682.

Example 7

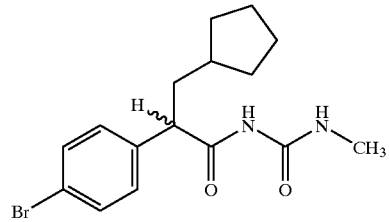

1-[2-(4-Bromo-phenyl)-3-cyclopentyl-propionyl]-3-methyl urea

A solution of diisopropylamine (7.7 mL, 54.88 mmol) in dry tetrahydrofuran (23 mL) and 1,3-dimethyl-3,4,5,6-tetrahydro-2(1H)-pyrimidinone (10 mL) was cooled to −78° C. under nitrogen and then treated with a 2.5M solution of n-butyllithium in hexanes (22.0 mL, 54.88 mmol). The reaction mixture was stirred at −78° C. for 30 min and then treated dropwise with a solution of 4-bromophenylacetic acid (5.62 g, 26.13 mmol) in dry tetrahydrofuran (23 mL) and 1,3-dimethyl-3,4,5,6-tetrahydro-2(1H)-pyrimidinone (10 mL). The reaction mixture turned dark in color and was allowed to stir at −78° C. for 1 h, at which time, a solution of iodomethylcyclopentane (5.76 g, 27.44 mmol) in a small amount of dry tetrahydrofuran was added dropwise. The reaction mixture was allowed to warm to 25° C. where it was stirred for 24 h. The reaction mixture was quenched with water and then concentrated in vacuo to remove tetrahydrofuran. The aqueous residue was acidified using a 10% aqueous hydrochloric acid solution. The resulting aqueous layer was extracted with ethyl acetate (2×100 mL). The combined organic extracts were dried over sodium sulfate, filtered, and concentrated in vacuo. Flash chromatography (Merck Silica gel 60, 230–400 mesh, 3/1 hexanes/ethyl acetate) afforded 2-(4-bromo-phenyl)-3-cyclopentyl-propionic acid (3.88 g, 50%) as a light yellow solid: mp 91–93° C.; EI-HRMS m/e calcd for $C_{14}H_{17}BrO_2$ (M$^+$) 296.0412, found 296.0417.

A solution of 2-(4-bromo-phenyl)-3-cyclopentyl-propionic acid (1.37 g, 4.61 mmol) in methanol (23 mL) was treated slowly with 5 drops of concentrated sulfuric acid. The resulting reaction mixture was heated under reflux for 42 h. The reaction mixture was allowed to cool to 25° C. and then concentrated in vacuo to remove methanol. The residue was diluted with ethyl acetate (200 mL). The organic phase was washed with a saturated aqueous sodium bicarbonate solution (1×100 mL), washed with a saturated aqueous sodium chloride solution (1×100 mL), dried over sodium sulfate, filtered, and concentrated in vacuo. Flash chromatography (Merck Silica gel 60, 70–230 mesh, 19/1 hexanes/ethyl acetate) afforded 2-(4-bromo-phenyl)-3-cyclopentyl-propionic acid methyl ester (1.40 g, 97%) as a light yellow oil: EI-HRMS m/e calcd for $C_{15}H_{19}BrO_2$ (M$^+$) 310.0568, found 310.0569.

2-(4-Bromo-phenyl)-3-cyclopentyl-propionic acid methyl ester (420.0 mg, 1.35 mmol) and methyl urea (299.9 mg, 4.05 mmol) were treated with a solution of magnesium methoxide in methanol (7.4 wt %, 7.7 mL, 5.40 mmol). The resulting reaction mixture was then heated under reflux for 48 h. The reaction mixture was allowed to cool to 25° C. and then filtered through celite. The celite was thoroughly washed with ethyl acetate, and the filtrate was concentrated in vacuo. Flash chromatography (Merck Silica gel 60, 70–230 mesh, 3/1 hexanes/ethyl acetate) afforded 1-[2-(4-bromo-phenyl)-3-cyclopentyl-propionyl]-3-methyl urea (58.7 mg, 12%) as a white solid: mp 184–186° C.; EI-HRMS m/e calcd for $C_{16}H_{21}BrN_2O_2$ (M$^+$) 352.0786, found 352.0791.

Example 8

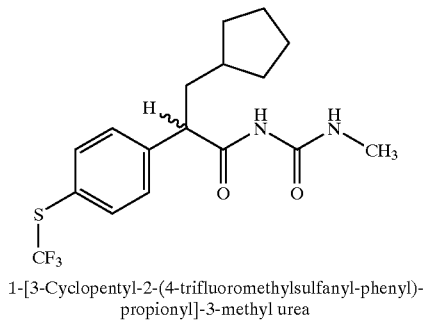

1-[3-Cyclopentyl-2-(4-trifluoromethylsulfanyl-phenyl)-propionyl]-3-methyl urea

A solution of diisopropylamine (2.4 mL, 16.80 mmol) in dry tetrahydrofuran (7.5 mL) and 1,3-dimethyl-3,4,5,6-tetrahydro-2(1H)-pyrimidinone (2.5 mL) was cooled to −78° C. under nitrogen and then treated with a 2.5M solution of n-butyllithium in hexanes (6.7 mL, 16.80 mmol). The resulting reaction mixture was stirred at −78° C. for 30 min and then treated dropwise with a solution of 4-(trifluoromethylthio)phenylacetic acid (1.89 g, 8.00 mmol) in dry tetrahydrofuran (7.5 mL) and 1,3-dimethyl-3,4,5,6-tetrahydro-2(1H)-pyrimidinone (2.5 mL). The reaction mixture was allowed to stir at −78° C. for 55 min, at which time, a solution of iodomethylcyclopentane (1.85 g, 8.80 mmol) in a small amount of dry tetrahydrofuran was added dropwise. The reaction mixture was allowed to warm to 25° C. where it was stirred for 41 h. The reaction mixture was quenched with water and then concentrated in vacuo to remove tetrahydrofuran. The remaining aqueous phase was acidified to pH=2 with a 10% aqueous hydrochloric acid solution and then extracted with ethyl acetate (1×300 mL). The organic layer was washed with a saturated aqueous sodium chloride solution (1×100 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-trifluoromethylsulfanyl-phenyl)propionic acid (1.47 g, 58%) as a cream solid: mp 69–71° C.; EI-HRMS m/e calcd for $C_{15}H_{17}F_3O_2S$ (M$^+$) 318.0901, found 318.0912.

A solution of 3-cyclopentyl-2-(4-trifluoromethylsulfanyl-phenyl)propionic acid (1.33 g, 4.18 mmol) in methanol (10 mL) was treated slowly with 4 drops of concentrated sulfuric acid. The resulting reaction mixture was heated under reflux for 36 h. The reaction mixture was allowed to cool to 25° C. and then concentrated in vacuo to remove methanol. The residue was diluted with ethyl acetate (200 mL). The organic phase was washed with a saturated aqueous sodium bicarbonate solution (1×100 mL), washed with a saturated aqueous sodium chloride solution (1×100 mL), dried over sodium sulfate, filtered, and concentrated in vacuo. Flash chromatography (Merck Silica gel 60, 70–230 mesh, 97/3 hexanes/ethyl acetate) afforded 3-cyclopentyl-2-(4-trifluoromethylsulfanyl-phenyl)propionic acid methyl ester (1.37 g, 99%) as a light yellow oil: EI-HRMS m/e calcd for $C_{16}H_{19}F_3O_2S$ (M$^+$) 332.1058, found 332.1052.

3-Cyclopentyl-2-(4-trifluoromethylsulfanyl-phenyl)propionic acid methyl ester (210.1 mg, 0.63 mmol) and methyl urea (140.5 mg, 1.90 mmol) were treated with a solution of magnesium methoxide in methanol (7.4 wt %, 3.6 mL, 2.53 mmol). The resulting reaction mixture was then heated under reflux for 64 h. The reaction mixture was allowed to cool to 25° C. and then filtered through celite. The celite was thoroughly washed with ethyl acetate until the solvent passing through the celite showed absence of desired product by thin layer chromatography. The filtrate was concentrated in vacuo. Flash chromatography (Merck Silica gel 60, 70–230 mesh, 3/1 hexanes/ethyl acetate) afforded 1-[3-cyclopentyl-2-(4-trifluoromethylsulfanyl-phenyl)-propionyl]-3-methyl urea (42.7 mg, 18%) as a white solid: mp 144–145° C.; EI-HRMS m/e calcd for $C_{17}H_{21}F_3N_2O_2S$ (M$^+$) 374.1276, found 374.1270.

Example 9

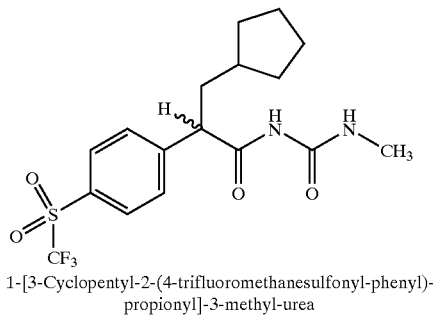

1-[3-Cyclopentyl-2-(4-trifluoromethanesulfonyl-phenyl)-propionyl]-3-methyl-urea

A solution of diisopropylamine (2.4 mL, 16.80 mmol) in dry tetrahydrofuran (7.5 mL) and 1,3-dimethyl-3,4,5,6-tetrahydro-2(1H)-pyrimidinone (2.5 mL) was cooled to −78° C. under nitrogen and then treated with a 2.5 M solution of n-butyllithium in hexanes (6.7 mL, 16.80 mmol). The resulting reaction mixture was stirred at −78° C. for 30 min and then treated dropwise with a solution of 4-(trifluoromethylthio)phenylacetic acid (1.89 g, 8.00 mmol) in dry tetrahydrofuran (7.5 mL) and 1,3-dimethyl-3, 4,5,6-tetrahydro-2(1H)-pyrimidinone (2.5 mL). The reaction mixture was allowed to stir at −78° C. for 55 min, at which time, a solution of iodomethylcyclopentane (1.85 g, 8.80 mmol) in a small amount of dry tetrahydrofuran was added dropwise. The reaction mixture was allowed to warm to 25° C. where it was stirred for 41 h. The reaction mixture was quenched with water and then concentrated in vacuo to remove tetrahydrofuran. The remaining aqueous phase was acidified to pH=2 with a 10% aqueous hydrochloric acid solution and then extracted with ethyl acetate (1×300 mL). The organic layer was washed with a saturated aqueous sodium chloride solution (1×100 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-trifluoromethylsulfanyl-phenyl)propionic acid (1.47 g, 58%) as a cream solid: mp 69–71° C.; EI-HRMS m/e calcd for $C_{15}H_{17}F_3O_2S$ ($M^+$) 318.0901, found 318.0912.

A solution of 3-cyclopentyl-2-(4-trifluoromethylsulfanyl-phenyl)propionic acid (1.33 g, 4.18 mmol) in methanol (10 mL) was treated slowly with 4 drops of concentrated sulfuric acid. The resulting reaction mixture was heated under reflux for 36 h. The reaction mixture was allowed to cool to 25° C. and then concentrated in vacuo to remove methanol. The residue was diluted with ethyl acetate (200 mL). The organic phase was washed with a saturated aqueous sodium bicarbonate solution (1×100 mL), washed with a saturated aqueous sodium chloride solution (1×100 mL), dried over sodium sulfate, filtered, and concentrated in vacuo. Flash chromatography (Merck Silica gel 60, 70–230 mesh, 97/3 hexanes/ethyl acetate) afforded 3-cyclopentyl-2-(4-trifluoromethylsulfanyl-phenyl)propionic acid methyl ester (1.37 g, 99%) as a light yellow oil: EI-HRMS m/e calcd for $C_{16}H_{19}F_3O_2S$ ($M^+$) 332.1058, found 332.1052.

A solution of 3-cyclopentyl-2-(4-trifluoromethylsulfanyl-phenyl)propionic acid methyl ester (1.14 g, 3.43 mmol) in methylene chloride (8.6 mL) was treated with 3-chloroperoxybenzoic acid (80–85% grade, 2.00 g based on 80%, 9.26 mmol). The reaction mixture was stirred at 25° C. for 17 h, at which time, thin layer chromatography showed the presence of two new lower $R_f$ products. An additional 2.00 g of 3-chloroperoxybenzoic acid was added to the reaction mixture to drive the conversion of the sulfoxide to the sulfone, and the resulting reaction mixture was stirred at 25° C. for 3 d. The reaction mixture was concentrated in vacuo to remove methylene chloride. The resulting residue was diluted with ethyl acetate (300 mL). The organic phase was washed with a saturated aqueous sodium bicarbonate solution (3×100 mL), washed with a saturated aqueous sodium chloride solution (1×100 mL), dried over sodium sulfate, filtered, and concentrated in vacuo. Flash chromatography (Merck Silica gel 60, 70–230 mesh, 19/1 hexanes/ethyl acetate) afforded 3-cyclopentyl-2-(4-trifluoromethanesulfonyl-phenyl)propionic acid methyl ester (1.19 g, 95%) as a light yellow oil: EI-HRMS m/e calcd for $C_{16}H_{19}F_3O_4S$ ($M^+$) 364.0956, found 364.0965.

3-Cyclopentyl-2-(4-trifluoromethanesulfonyl-phenyl) propionic acid methyl ester (383.8 mg, 1.05 mmol) and methyl urea (234.1 mg, 3.16 mmol) were treated with a solution of magnesium methoxide in methanol (7.4 wt %, 6.0 mL, 4.21 mmol). The resulting reaction mixture was then heated under reflux for 2 d. The reaction mixture was allowed to cool to 25° C. and then filtered through celite. The celite was thoroughly washed with ethyl acetate until the solvent passing through the celite showed absence of desired product by thin layer chromatography. The filtrate was concentrated in vacuo. Flash chromatography (Merck Silica gel 60, 70–230 mesh, 3/1 hexanes/ethyl acetate) afforded 1-[3-cyclopentyl-2-(4-trifluoromethanesulfonyl-phenyl)-propionyl]-3-methyl urea (119.3 mg, 28%) as a white solid: mp 191–192° C.; FAB-HRMS m/e calcd for $C_{17}H_{21}F_3N_2O_4S$ $(M+H)^+$ 407.1252, found 407.1247.

Example 10

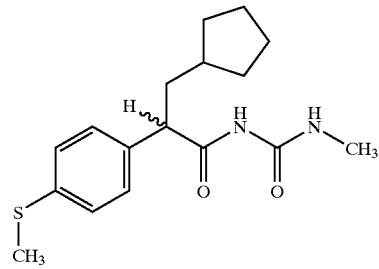

1-[3-Cyclopentyl-2-(4-methylsulfanyl-phenyl)-propionyl]-3-methyl urea

A solution of diisopropylamine (3.2 mL, 23.16 mmol) in dry tetrahydrofuran (10.3 mL) and 1,3-dimethyl-3,4,5,6-tetrahydro-2 (1 H)-pyrimidinone (3.4 mL) was cooled to −78° C. under nitrogen and then treated with a 10M solution of n-butyllithium in hexanes (2.3 mL, 23.16 mmol). The resulting reaction mixture was stirred at −78° C. for 30 min and then treated dropwise with a solution of 4-(methylthio) phenylacetic acid (2.01 g, 11.03 mmol) in dry tetrahydrofuran (10.3 mL) and 1,3-dimethyl-3,4,5,6-tetrahydro-2(1H)-pyrimidinone (3.4 mL). The reaction mixture was allowed to stir at −78° C. for 1 h, at which time, a solution of iodomethylcyclopentane (2.55 g, 12.13 mmol) in a small amount of dry tetrahydrofuran was added dropwise. The reaction mixture was stirred at −78° C. for 30 min and then allowed to warm to 25° C. where it was stirred for 24 h. The reaction mixture was quenched with water and then concentrated in vacuo to remove tetrahydrofuran. The remaining aqueous phase was acidified to pH=2 with a 10% aqueous hydrochloric acid solution and then extracted. with ethyl acetate (200 mL). The organic layer was washed with a saturated aqueous sodium chloride solution (1×100 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-methylsulfanyl-phenyl)propionic acid (1.01 g, 35%) as a cream solid: mp 91–93° C.; EI-HRMS m/e calcd for $C_{15}H_{20}O_2S$ ($M^+$) 264.1184, found 264.1177.

A solution of 3-cyclopentyl-2-(4-methylsulfanyl-phenyl) propionic acid (500 mg, 1.89 mmol) in methanol (8 mL) was treated slowly with 2 drops of concentrated sulfuric acid. The resulting reaction mixture was heated under reflux for 15 h. The reaction mixture was allowed to cool to 25° C. and then concentrated in vacuo. The orange residue was partitioned between water and ethyl acetate. The organic layer was dried over magnesium sulfate, filtered, and concentrated in vacuo to provide pure 3-cyclopentyl-2-(4-methylsulfanyl-phenyl)propionic acid methyl ester (481 mg, 91%) as a yellow-orange oil which was used without further purification: EI-HRMS m/e calcd for $C_{16}H_{22}O_2S$ ($M^+$) 278.1341, found 278.1347.

3-Cyclopentyl-2-(4-methylsulfanyl-phenyl)propionic acid methyl ester (400 mg, 1.44 mmol) and methyl urea (267 mg, 3.60 mmol) were treated with a solution of magnesium methoxide in methanol (7.4 wt %, 5.6 mL, 3.89 mmol). The reaction mixture was then concentrated in vacuo to approximately one-half the volume of methanol. The resulting reaction mixture was then heated under reflux for 15 h. The reaction mixture was allowed to cool to 25° C., filtered through celite, and the celite was thoroughly washed with ethyl acetate. The ethyl acetate filtrate was washed with water. The organic layer was dried over magnesium sulfate, filtered, and concentrated in vacuo. Flash chromatography (Merck Silica gel 60, 230–400 mesh, 2/1 hexanes/ethyl acetate) afforded 1-[3-cyclopentyl-2-(4-methylsulfanyl-phenyl)-propionyl]-3-methyl urea (141 mg, 31%) as a white solid: mp 185–186° C.; EI-HRMS m/e calcd for $C_{17}H_{24}N_2O_2S$ ($M^+$) 320.1559, found 320.1559.

Example 11

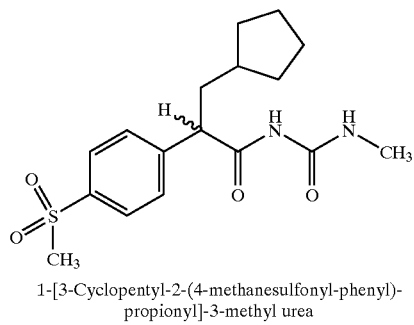

1-[3-Cyclopentyl-2-(4-methanesulfonyl-phenyl)-propionyl]-3-methyl urea

A solution of diisopropylamine (3.3 mL, 23.5 mmol) in dry tetrahydrofuran (50 mL) and 1,3-dimethyl-3,4,5,6-tetrahydro-2(1H)-pyrimidinone (10 mL) was cooled to –78° C. under nitrogen and then treated with a 10M solution of n-butyllithium in hexanes (2.35 mL, 23.5 mmol). The yellow reaction mixture was stirred at –78° C. for 30 min and then treated dropwise with a solution of 4-methylsulfonylphenylacetic acid (2.40 g, 11.2 mmol) in a small amount of dry tetrahydrofuran. After approximately one-half of the 4-methylsulfonylphenylacetic acid in dry tetrahydrofuran was added, a precipitate formed. Upon further addition of the remaining 4-methylsulfonylphenylacetic acid in dry tetrahydrofuran, the reaction mixture became thick in nature. After complete addition of the 4-methylsulfonylphenylacetic acid in dry tetrahydrofuran, the reaction mixture was very thick and became difficult to stir. An additional amount of dry tetrahydrofuran (20 mL) was added to the thick reaction mixture, and the reaction mixture was stirred at –78° C. for 45 min, at which time, a solution of iodomethylcyclopentane (2.35 g, 11.2 mmol) in a small amount of dry tetrahydrofuran was added dropwise. The reaction mixture was allowed to warm to 25° C. where it was stirred for 15 h. The reaction mixture was quenched with water (100 mL), and the resulting yellow reaction mixture was concentrated in vacuo to remove tetrahydrofuran. The aqueous residue was acidified to pH=2 using concentrated hydrochloric acid. The aqueous layer was extracted with ethyl acetate. The organic phase was dried over magnesium sulfate, filtered, and concentrated in vacuo. Flash chromatography (Merck Silica gel 60, 230–400 mesh, 1/3 hexanes/ethyl acetate) afforded 3-cyclopentyl-2-(4-methanesulfonyl-phenyl)propionic acid (1.80 g, 52%) as a white solid: mp 152–154° C.; EI-HRMS m/e calcd for $C_{15}H_{20}O_4S$ ($M^+$) 296.1082, found 296.1080.

A solution of 3-cyclopentyl-2-(4-methanesulfonyl-phenyl)propionic acid (500 mg, 1.89 mmol) in methanol (15 mL) was treated slowly with concentrated sulfuric acid (3 drops). The resulting reaction mixture was heated under reflux for 15 h. The reaction mixture was allowed to cool to 25° C. and then concentrated in vacuo. Flash chromatography (Merck Silica gel 60, 230–400 mesh, 1/3 hexanes/ethyl acetate) afforded 3-cyclopentyl-2-(4-methanesulfonyl-phenyl)propionic acid methyl ester (377 mg, 72%) as a white solid: mp 63–66° C.; EI-HRMS m/e calcd for $C_{16}H_{22}O_4S$ ($M^+$) 310.1239, found 310.1230.

3-Cyclopentyl-2-(4-methanesulfonyl-phenyl)propionic acid methyl ester (350 mg, 1.13 mmol) and methyl urea (184 mg, 2.48 mmol) were treated with a solution of magnesium methoxide in methanol (7.4 wt %, 6.0 mL, 4.18 mmol). The reaction mixture was then concentrated in vacuo to approximately one-half the volume of methanol. The resulting reaction mixture was then heated under reflux for 15 h. The reaction mixture was allowed to cool to 25° C., filtered through celite, and the celite was thoroughly washed with ethyl acetate. The ethyl acetate filtrate was washed with water. The organic layer was dried over magnesium sulfate, filtered, and concentrated in vacuo. Flash chromatography (Merck Silica gel 60, 230–400 mesh, 1/3 hexanes/ethyl acetate) afforded 1-[3-cyclopentyl-2-(4-methanesulfonyl-phenyl)-propionyl]-3-methyl urea (124 mg, 31%) as a white solid: mp 205–206° C.; EI-HRMS m/e calcd for $C_{17}H_{24}N_2O_4S$ ($M^+$) 352.1457, found 352.1445.

Example 12

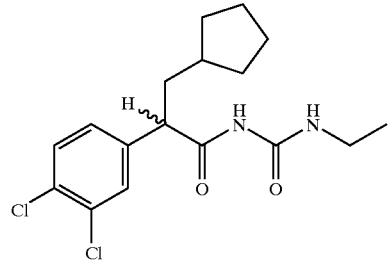

(A) 1-[3-Cyclopentyl-2-(3,4-dichloro-phenyl)-propionyl]-3-ethyl-urea

A solution of triphenylphosphine (28.80 g, 109.8 mmol) and imidazole (14.9 g, 219.6 mmol) in methylene chloride (160 mL) was cooled to 0° C. and then slowly treated with iodine (27.87 g, 109.8 mmol). The reaction mixture was then treated dropwise with a solution of cyclopentylmethanol (10.0 g, 99.8 mmol) in methylene chloride (10 mL). The resulting reaction mixture was allowed to warm to 25° C., where it was stirred for 4 h. The reaction mixture was then diluted with water (50 mL), and the reaction mixture was further extracted with methylene chloride (3×20 mL). The combined organic layers were dried over sodium sulfate, filtered and concentrated in vacuo at 25° C. The resulting solid was washed with pentane (4×50 mL) and filtered through a silica gel plug. The filtrate was concentrated in vacuo at 25° C. to afford iodomethylcyclopentane (18.48 g, 88%) as a clear colorless liquid: EI-HRMS m/e calcd for $C_6H_{11}I$ ($M^+$) 209.9906, found 209.9911.

A solution of diisopropylamine (13.36 mL, 101.89 mmol) in tetrahydrofuran (250 mL) was cooled to –78° C. under a nitrogen atmosphere and then treated with a 2.0M solution of n-butyllithium in hexanes (51 mL, 101.89 mmol). The reaction mixture was stirred at –78° C. for 15 min, at which time, a solution of 3,4-dichlorophenyl acetic acid (9.08 g, 44.3 mmol) in tetrahydrofuran (60 mL) and hexamethylphosphoramide (20 mL) was slowly added via a cannula. The bright yellow solution was allowed to stir at –78° C. for 1 h, at which time, a solution of iodomethylcyclopentane (11.17 g, 53.2 mmol) in hexamethylphosphoramide (10 mL) was added via a cannula. The reaction mixture was stirred at −78° C. for 1 h. The reaction mixture was then allowed to warm to 25° C., where it was stirred for 14 h. The reaction mixture was then acidified to pH=2 by the dropwise addition of a 1N aqueous hydrochloric acid solution and extracted with ethyl acetate (3×50 mL). The combined organic layers were dried with sodium sulfate, filtered, and concentrated in vacuo. Flash chromatography (Merck Silica gel 60, 230–400 mesh, chloroform then 99/1 chloroform/methanol) afforded 3-cyclopentyl-2-(3,4-dichlorophenyl)-propionic acid (10.28 g, 81%) as a white solid: mp 74.5–76.9° C.; EI-HRMS m/e calcd for $C_{14}H_{16}Cl_2O_2$ ($M^+$) 286.0527, found 286.0534.

A solution of 3-cyclopentyl-2-(3,4-dichlorophenyl)-propionic acid (366 mg, 1.27 mmol) in methylene chloride (10 mL) and 1 drop of N,N-dimethylformamide was cooled to 0° C. and then treated with a 2.0M solution of oxalyl chloride in methylene chloride (0.76 mL, 1.53 mmol). The reaction was stirred for 30 min at 0° C., at which time, 1,1,1,3,3,3-hexamethyldisilazane (0.81 mL, 3.81 mmol) was added to the reaction mixture. The reaction was allowed to slowly warm to 25° C. and then stirred at 25° C. for 16 h. The reaction mixture was then treated with methanol (5 mL). The resulting reaction mixture was washed with a 5% aqueous sulfuric acid solution (2×10 mL). The combined aqueous layers were extracted with methylene chloride (3×10 mL). The combined organic layers were then washed with a saturated aqueous sodium chloride solution (1×10 mL), dried over magnesium sulfate, filtered and concentrated in vacuo. Flash chromatography (Merck Silica gel 60, 230–400 mesh, 70/30 hexanes/ethyl acetate) afforded 3-cyclopentyl-2-(3,4-dichloro-phenyl)-propionamide (229 mg, 63%) as a white solid: mp 98.6–100.1° C.; EI-HRMS m/e calcd for $C_{14}H_{17}Cl_2NO$ ($M^+$) 285.0687, found 285.0688.

A solution of 3-cyclopentyl-2-(3,4-dichloro-phenyl)-propionamide (98 mg, 0.33 mmol) in toluene (10 mL) was treated with ethyl isocyanate (0.03 mL, 0.42 mmol). The resulting solution was heated under reflux for 24 h. At this time, the reaction was concentrated in vacuo. Flash chromatography (Merck Silica gel 60, 230400 mesh, 90/10 hexanes/ethyl afforded 1-[3-cyclopentyl-2-(3,4-dichloro-phenyl)-propionyl]-3-ethyl-urea (29 mg, 26%) as a white foam: EI-HRMS m/e calcd for $C_{17}H_{22}Cl_2N_2O_2$ ($M^+$) 356.1058, found 356.1066.

(B) In an Analogous Manner, There Were Obtained:

(a) From 3-cyclopentyl-2-(3,4-dichloro-phenyl)-propionamide and isopropyl isocyanate: 1-[3-Cyclopentyl-2-(3,4-dichloro-phenyl)-propionyl]-3-isopropyl-urea as a white solid: mp 134.6–138.3° C.; EI-HRMS m/e calcd for $C_{18}H_{24}Cl_2N_2O_2$ ($M^+$) 370.1215, found 370.1232.

(b) From 3-cyclopentyl-2-(3,4-dichloro-phenyl)-propionamide and propyl isocyanate: 1-[3-Cyclopentyl-2-(3,4-dichloro-phenyl)-propionyl]-3-propyl-urea as a white solid: mp 117.8–120° C.; EI-HRMS m/e calcd for $C_{18}H_{24}Cl_2N_2O_2$ ($M^+$) 370.1215, found 370.1209

(c) From 3-cyclopentyl-2-(3,4-dichloro-phenyl)-propionamide and ethyl 3-isocyanatopropionate: 3-{3-[3-Cyclopentyl-2-(3,4-dichloro-phenyl)-propionyl]-ureido)}-propionic acid ethyl ester as a light yellow oil: EI-HRMS m/e calcd for $C_{21}H_{26}Cl_2N_2O_4$($M^+$) 428.1270, found 428.1265.

(d) From 3-cyclopentyl-2-(3,4-dichloro-phenyl)-propionamide and ethyl isocyanatoacetate: {3-[3-Cyclopentyl-2-(3,4-dichloro-phenyl)-propionyl]-ureido}-acetic acid ethyl ester as a light yellow oil: EI-H RMS m/e calcd for $C_{19}H_{24}Cl_2N_2O_4$($M^+$) 414.1113, found 414.1108.

(e) From 3-cyclopentyl-2-(3,4-dichloro-phenyl)-propionamide and allyl isocyanate: 1-Allyl-3-[3-cyclopentyl-2-(3,4-dichloro-phenyl)-propionyl]-urea as a clear colorless oil: EI-HRMS m/e calcd for $C_{18}H_{22}Cl_2N_2O_2$ ($M^+$) 368.1058, found 368.1064.

Example 13

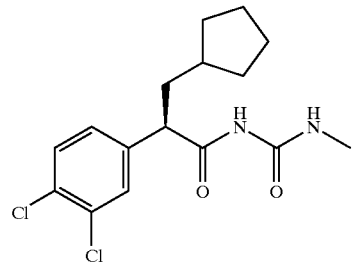

1-[3-Cyclopentyl-2(R)-(3,4-dichloro-phenyl)-propionyl]-3-methyl-urea

A solution of 3-cyclopentyl-2-(3,4-dichloro-phenyl)-propionic acid (prepared in Example 12, 5.00 g, 17.4 mmol) in tetrahydrofuran (150 ML) cooled to −78° C. was treated with triethylamine (2.77 mL, 19.9 mmol) followed by tri-methylacetyl chloride (2.24 mL, 18.2 mmol). The resulting white slurry was stirred at −78° C. for 15 min and then at 0° C. for 45 min. In a separate flask, a solution of (S)-4-isopropyl-2-oxazolidinone (2.14 g, 16.57 mmol) in tetrahydrofuran (80 mL) cooled to −78° C. was treated with a 2.0M solution of n-butyllithium in hexanes (8.7 mL, 17.4 mmol). This solution was stirred at −78° C. for 10 min. It was then warmed 25° C. and stirred for an additional 10 min. At this time, the first reaction mixture was re-cooled to −78° C. The second reaction mixture was added to the first reaction mixture over a period of 5 min via cannula. The combined reaction was then stirred at −78° C. for 15 min. It was then warmed to 25° C. and was stirred for an additional 1.5 h. At this time, the reaction was quenched by the addition of a saturated aqueous sodium bisulfite solution (50 mL) and extracted with ethyl acetate (3×40 mL). The organic layers were combined, washed with a saturated aqueous sodium bicarbonate solution (1×20 mL), a saturated aqueous sodium chloride solution (1×20 mL), dried over sodium sulfate, filtered, and concentrated in vacuo. Flash chromatography (Merck Silica gel 60, 230–400 mesh, 85/15 hexanes/ethyl acetate) afforded (1) 3-[3-cyclopentyl-2(S)-(3,4-dichloro-phenyl)-propionyl]-4(S)-isopropyl-oxazolidin-2-one (2.15 g, 33%) as a clear oil: $[\alpha]^{23}_{589}$=+87.5° (c=0.160, chloroform); EI-HRMS m/e calcd for $C_{20}H_{25}Cl_2NO_3$($M^+$) 397.1211, found 397.1215 and (2) 3-[3-cyclopentyl-2(R)-(dichloro-phenyl)-propionyl]-4(S)-isopropyl-oxazolidin-2-one (1.88 g, 28%) as a white solid: mp 71.9–74.6° C.; $[\alpha]^{23}_{589}$=−27.6° (c=0.188, chloroform); EI-HRMS m/e calcd for $C_{20}H_{25}Cl_2NO_3$($M^+$) 397.1211, found 397.1212.

A solution of 3-[3-cyclopentyl-2(R)-(3,4-dichloro-phenyl)-propionyl]-4(S)-isopropyl-oxazolidin-2-one (1.88 g, 4.72 mmol) in tetrahydrofuran (73 mL) and water (22 mL) cooled to 0° C. was treated with a 30% aqueous hydrogen peroxide solution (2.1 mL) and lithium hydroxide (394 mg, 9.4 mmol). The reaction was stirred at 0° C. for 1 h. At this time, the reaction was quenched with a saturated aqueous sodium sulfite solution (16 mL) followed by the addition of an aqueous solution of 0.5N sodium bicarbonate (50 mL). The tetrahydrofuran was then removed in vacuo. The residue was diluted with water (40 mL) and extracted with methylene chloride (3×20 mL). The aqueous layer was then acidified to pH=2 with a 5N aqueous hydrochloric acid solution and extracted with ethyl acetate (4×25 mL). The ethyl acetate layers were then dried over sodium sulfate, filtered, and concentrated in vacuo to afforded of 3-cyclopentyl-2 (R)-(3,4-dichloro-phenyl)-propionic acid (928 mg, 70%) as a white solid: mp 75.1–78.3, C; $[\alpha]^{23}_{589}$=−50.3° (c=0.100, chloroform); EI-HRMS m/e calcd for $C_{14}H_{16}Cl_2O_2$ (M) 286.0527, found 286.0535.

A solution of 3-cyclopentyl-2(R)-(3,4-dichlorophenyl)-propionic acid (105 mg, 0.37 mmol) in methylene chloride (10 mL) and 1 drop of N,N-dimethylformamide was cooled to 0° C. and then treated with a 2.0M solution of oxalyl chloride in methylene chloride (0.18 mL, 0.37 mmol). The reaction was stirred for 30 min at 0° C., at which time, 1,1,1,3,3,3-hexamethyldisilazane (0.25 mL, 1.17 mmol) was added to the reaction mixture. The reaction was then allowed to slowly warm to 25° C. and stirred at 25° C. for 16 h. The reaction mixture was then washed with a 5% aqueous sulfuric acid solution (2×10 mL). The combined aqueous layers were extracted with methylene chloride (3×10 mL). The combined organic layers were washed with a saturated aqueous sodium chloride solution (1×10 mL), dried over magnesium sulfate, filtered and concentrated in vacuo. Flash chromatography (Merck Silica gel 60, 230–400 mesh, 60/40 hexanes/ethyl acetate) afforded 3-cyclopentyl-2(R)-(3,4-dichloro-phenyl)-propionamide (60 mg, 58%) as a white solid: $[\alpha]^{23}_{589}$=−67.6° (c=0.106, chloroform); EI-HRMS m/e calcd for $C_{14}H_{17}Cl_2N_1O_1(M^+)$ 285.0687, found 285.0685.

A solution of 3-cyclopentyl-2(R)-(3,4-dichloro-phenyl)-propionamide (54 mg, 0,19 mmol) in toluene (5 mL) was treated with methyl isocyanate (0.03 mL, 0.47 mmol). The resulting solution was heated under reflux for 24 h. At this time, the reaction was concentrated in vacuo. Flash chromatography (Merck Silica gel 60, 230–400 mesh 70/30 hexanes/ethyl acetate) afforded 1-[3-cyclopentyl-2(R)-(3,4-dichloro-phenyl)-propionyl]-3-methyl-urea (40 mg, 63%) as a white solid: mp 124.8–127.5° C.; $[\alpha]^{23}_{589}$=−21.2° (c=0.099, chloroform); EI-HRMS m/e calcd for $C_{16}H_{20}Cl_2N_2O_2$ ($M^+$) 342.0902, found 342.0902.

Example 14

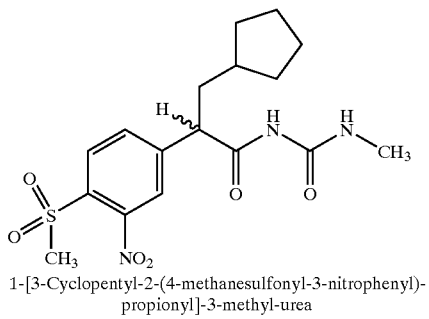

1-[3-Cyclopentyl-2-(4-methanesulfonyl-3-nitrophenyl)-propionyl]-3-methyl-urea

A solution of 4-chloro-3-nitrophenylacetamide (2.00 g, 9.32 mmol) in methanol (40 mL) was treated with Amberlyst® 15 ion exchange resin (15.00 g). The resulting reaction mixture was heated under reflux for 64 h. The reaction mixture was allowed to cool to 25° C. and then filtered to remove the Amberlyst® 15 ion exchange resin. The filtrate was concentrated in vacuo. Flash chromatography (Merck Silica gel 60, 230–400 mesh, 3/1 hexanes/ethyl acetate) afforded 4-chloro-3-nitrophenylacetic acid methyl ester (1.91 g, 89%) as a yellow oil: EI-HRMS m/e calcd for $C_9H_8ClNO_4(M^+)$ 229.0142, found 229.0146.

A solution of diisopropylamine (3.35 mL, 23.9 mmol) in dry tetrahydrofuran (45 mL) and 1,3-dimethyl-3,4,5,6-tetrahydro-2(1H)-pyrimidinone (15 mL) was cooled to −78° C. and then treated dropwise with a 2.5 M solution of n-butyllithium in hexanes (9.56 mL, 23.9 mmol) over a 10 min period. The pale yellow reaction mixture was stirred at −78° C. for 20 min and then slowly treated with a solution of 4-chloro-3-nitrophenylacetic acid methyl ester (5.00 g, 21.8 mmol) in a small amount of tetrahydrofuran over a 15 min period. The reaction mixture turned deep purple (almost black) in color. The reaction mixture was then stirred at −78° C. for 1 h, at which time, a solution of iodomethylcyclopentane (4.58 g, 21.8 mol) in a small amount of dry tetrahydrofuran was added dropwise. The reaction mixture was then stirred at −78° C. and then allowed to warm to 25° C., where it was stirred for 48 h. The reaction mixture was quenched with a saturated aqueous ammonium chloride solution (50 mL), and the resulting reaction mixture was concentrated in vacuo to remove tetrahydrofuran. The remaining residue was diluted with ethyl acetate (150 mL) and water (50 mL). The organic phase was washed with a saturated aqueous sodium chloride solution, dried over magnesium sulfate, filtered, and concentrated in vacuo. Flash chromatography (Merck Silica gel 60, 230–400 mesh, 4/1 hexanes/ethyl acetate) afforded 2-(4-chloro-3-nitrophenyl)-3-cyclopentyl-propionic acid methyl ester (2.17 g, 32%) as a yellow oil: EI-HRMS m/e calcd for $C_{15}H_{18}ClNO_4(M^+)$ 311.0924, found 311.0927.

A solution of 2-(4-chloro-3-nitrophenyl)-3-cyclopentyl-propionic acid methyl ester (1.00 g, 3.21 mmol) and sodium methanesulfinate (0.36 g, 3.53 mmol) in dimethyl sulfoxide (3mL) was heated at 130° C. for 5 h. The black reaction mixture was then poured over ice (20 g), resulting in the formation of a brown sticky substance. The resulting mixture was then diluted with ethyl acetate (50 mL) and water (50 mL), and the layers were separated. The aqueous layer was further extracted with ethyl acetate (2×50 mL). The combined organic layers were washed with a saturated aqueous sodium chloride solution, dried over magnesium sulfate, filtered, and concentrated in vacuo. Flash chromatography (Merck Silica gel 60, 230–400 mesh, 1/1 hexanes/ethyl acetate) afforded 3-cyclopentyl-2-(4-methanesulfonyl-3-nitrophenyl)-propionic acid methyl ester (0.95 g, 84%) as a yellow gel: FAB-HRMS m/e calcd for $C_{16}H_{21}NO_6S$ $(M+H)^+$356.1169, found 356.1175.

A solution of 3-cyclopentyl-2-(4-methanesulfonyl-3-nitrophenyl)-propionic acid methyl ester (865 mg, 2.43 mmol) in tetrahydrofuran (6 mL) was treated with a 0.8M aqueous lithium hydroxide solution (4.6 mL, 3.65 mmol). The reaction mixture was stirred at 25° C. for 3 h. The reaction mixture was concentrated in vacuo to remove tetrahydrofuran. The resulting aqueous residue was diluted with water (25 mL) and then treated with a 1N aqueous hydrochloric acid solution (10 mL). The resulting aqueous layer was then extracted with ethyl acetate (2×50 mL). The combined organic layers were dried over magnesium sulfate, filtered, and concentrated in vacuo. Flash chromatography (Merck Silica gel 60, 230–400 mesh, 1/4 hexanes/ethyl acetate) afforded 3-cyclopentyl-2-(4-methanesulfonyl-3-nitrophenyl)-propionic acid (723 mg, 87%) as a white foam. Analytical data indicated the presence of a small impurity; however, the 3-cyclopentyl-2-(4-methanesulfonyl-3-nitrophenyl)-propionic acid was used without further purification in subsequent reactions.

A mixture of 3-cyclopentyl-2-(4-methanesulfonyl-3-nitrophenyl)-propionic acid (300 mg, 0.88 mmol) and 1 drop of N,N-dimethylformamide in methylene chloride (2 mL)

was cooled to 0° C. and then slowly treated with oxalyl chloride (84 μL, 0.97 mmol). The reaction mixture was stirred at 0° C. for 10 min and then stirred at 25° C. for 1 h. The resulting reaction mixture was then treated dropwise with 1,1,1,3,3,3-hexamethyldisilazane (560 μL, 2.64 mmol) and subsequently stirred at 25° C. for 15 h. The resulting reaction mixture was diluted with methylene chloride (20 mL) and methanol (15 mL) and then washed with a 5% aqueous sulfuric acid solution (20 mL). The organic layer was dried over sodium sulfate, filtered, and concentrated in vacuo. Flash chromatography (Merck Silica gel 60, 230–400 mesh, 1/3 hexanes/ethyl acetate) afforded 3-cyclopentyl-2-(4-methanesulfonyl-3-nitrophenyl)-propionamide (140 mg, 47%) as a yellow foam: mp 72–76° C. (foam to gel); FAB-HRMS m/e calcd for $C_{15}H_{20}N_2O_5S$ (M+H)$^+$341.1172, found 341.1181.

A solution of 3-cyclopentyl-2-(4-methanesulfonyl-3-nitrophenyl)-propionamide (126 mg, 0.37 mmol) and methyl isocyanate (211 mg, 3.70 mmol) in toluene (2 mL) was heated under reflux (120° C.) for 15 h. The reaction mixture was allowed to cool to 25° C. and then concentrated in vacuo. The resulting yellow oil was treated with a small amount of a 1/1 mixture of hexanes/ethyl acetate, and a precipitate started to form. The material was further cooled in the freezer for 2 h to facilitate additional precipitation. The solid was collected by filtration and then dried in vacuo to afford 1-[3-cyclopentyl-2-(4-methanesulfonyl-3-nitrophenyl)-propionyl]-3-methyl-urea (50 mg, 35%) as a pale yellow solid: mp 241–242° C.; FAB-HRMS m/e calcd for $C_{17}H_{23}N_3O_6S$ (M+H)$^+$398.1386, found 398.1399.

Example 15

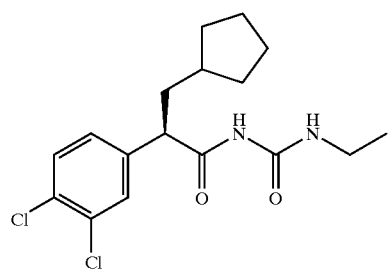

1-[3-Cyclopentyl-2(R)-(3,4-dichloro-phenyl)-propionyl]-3-ethyl-urea

A solution of 3-cyclopentyl-2(R)-(3,4-dichloro-phenyl)-propionamide (prepared in Example 13, 103 mg, 0.36 mmol) in toluene (10 mL) was treated with ethyl isocyanate (40 μL, 0.54 mmol). The resulting reaction mixture was heated under reflux for 24 h. The reaction mixture was then concentrated in vacuo. Flash chromatography (Merck Silica gel 60, 230–400 mesh, 4/1 hexanes/ethyl acetate) afforded 1-[3-cyclopentyl-2(R)-(3,4-dichloro-phenyl)-propionyl]-3-ethyl-urea (54 mg, 42%) as a white foam: $[\alpha]^{23}_{589}$=−41.9° (c=0.031, chloroform); FAB-HRMS m/e calcd for $C_{17}H_{22}Cl_2N_2O_2$ (M+H)$^+$357.1136, found 357.1137.

Example 16

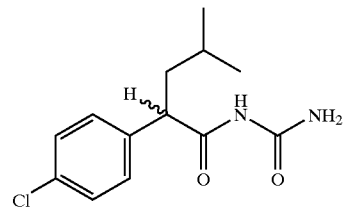

[2-(4-Chloro-phenyl)-4-methyl-pentanoyl]-urea

A solution of (4-chloro-phenyl)-acetic acid (6.29 g, 0.03 mol) in ethanol (38.4 mL) was treated with a catalytic amount of sulfuric acid. The reaction mixture was refluxed for 12 h. The reaction was then concentrated in vacuo. Flash chromatography (Merck Silica gel 60, 230–400 mesh, 50/50 hexanes/ethyl acetate) afforded (4-chloro-phenyl)-acetic acid ethyl ester (6.45 g, 88%) as a pale yellow solid: mp 39–41° C.; EI-HRMS m/e calcd for $C_{10}H_{11}ClO_2$ (M$^+$) 198.0448, found 198.0452.

A solution of freshly prepared lithium diisopropylamide (21.2 mL of a 0.31 M stock solution, 6.14 mmol) cooled to −78° C. was treated with (4-chloro-phenyl)-acetic acid ethyl ester (1.11 g, 5.58 mmol) in tetrahydrofuran/hexamethylphosphoramide (13.9 mL, 3:1). The resulting solution was stirred at −78° C. for 45 min. At this time, the reaction was treated with a solution of 1-bromo-2-methyl-propane (1.81 mL, 16.7 mmol) in hexamethylphosphoramide (1 mL). The mixture was stirred at −78° C. for 3 h. The reaction was then warmed to 25° C. and was stirred at 25° C. for 16 h. The reaction mixture was then quenched by the dropwise addition of a saturated aqueous ammonium chloride solution (20 mL). The reaction mixture was poured into water (100 mL) and extracted with ethyl acetate (3×50 mL). The organics layers dried over sodium sulfate, filtered, and concentrated in vacuo. Flash chromatography (Merck Silica gel 60, 230–400 mesh, 50/50 hexanes/ethyl acetate) afforded 2-(4-chloro-phenyl)-4-methyl-pentanoic acid ethyl ester (1.24 g, 87.1%) as a white solid: mp 34–35° C.; EI-HRMS m/e calcd for $C_{14}H_{19}ClO_2$ (M$^+$) 254.1074, found 254.1069.

A mixture of 2-(4-chloro-phenyl)-4-methyl-pentanoic acid ethyl ester (508 mg, 1.99 mmol) and urea (239 mg, 3.99 mmol) in a solution of magnesium methoxide in methanol (7.4 wt %, 4.28 mL, 2.99 mmol) was heated to reflux for 24 h. The reaction mixture was then concentrated in vacuo. Flash chromatography (Merck Silica gel 60, 230–400 mesh, 50/50 hexanes/ethyl acetate) afforded [2-(4-chloro-phenyl)-4-methyl-pentanoyl]-urea (28.1 mg, 5.2%) as a white solid: mp 164–165° C.; EI-HRMS m/e calcd for $C_{13}H_{17}ClN_2O_2$ (M$^+$) 268.0979, found 268.0972.

Example 17

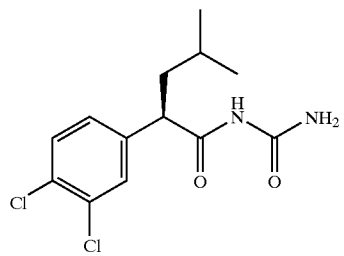

R-[2-(3,4-Dichloro-phenyl)-4-methyl-pentanoyl]-urea

A solution of (3,4-dichloro-phenyl)-acetic acid (10.0 g, 0.048 mol) in ethanol (50 mL) was treated with a catalytic amount of sulfuric acid. The reaction mixture was refluxed for 7 h. The reaction was concentrated in vacuo, diluted with diethyl ether, and poured into water. The ether layer was washed with a saturated aqueous sodium bicarbonate solution and water. The organics were then dried over sodium sulfate, filtered, and concentrated in vacuo. Vacuum distillation (bath temperature: 175° C.; head temperature: 125° C.) afforded (3,4-dichloro-phenyl)-acetic acid ethyl ester (9.38 g, 82.5%) as a clear oil: EI-HRMS m/e calcd for $C_{10}H_{10}Cl_2O_2$ (M$^+$) 232.0058, found 232.0066.

A solution of freshly prepared lithium diisopropylamide (4.88 mL of 0.29 M stock solution, 1.41 mmol) cooled to −78° C. was treated with (3,4-dichloro-phenyl)-acetic acid ethyl ester (300 mg, 1.28 mmol) in tetrahydrofuran/hexamethylphosphoramide (3.2 mL, 3:1). The resulting solution was stirred at −78° C. for 45 min. At this time, the reaction was treated with a solution of 1-bromo-2-methylpropane (1.53 mL, 1.41 mmol) in hexamethylphosphoramide (1 mL). The reaction mixture was stirred at −78° C. for 6 h. The reaction was then warmed to 25° C. and stirred at 25° C. for 16 h. The reaction mixture was then quenched by the dropwise addition of saturated aqueous ammonium chloride solution (1 mL). This mixture was poured into water (50 mL) and extracted with ethyl acetate (3×50 mL). The organics were dried over sodium sulfate, filtered, and concentrated in vacuo. Flash chromatography (Merck Silica gel 60, 230–400 mesh, 50/50 hexanes/ethyl acetate) afforded 2-(3,4-dichloro-phenyl)-4-methyl-pentanoic acid ethyl ester (356.4 mg, 95.8%) as a clear oil: EI-HRMS m/e calcd for $C_{14}H_{18}Cl_2O_2$ (M$^+$) 288.0683, found 288.0677.

A mixture of 2-(3,4-dichloro-phenyl)-4-methyl-pentanoic acid ethyl ester (197 mg, 0.68 mmol) and urea (82 mg, 1.36 mmol) in a solution of magnesium methoxide in methanol (7.4 wt %, 1.46 mL, 1.02 mmol) was heated to reflux for 3 h. The reaction mixture was then concentrated in vacuo. Flash chromatography (Merck Silica gel 60, 230–400 mesh, 75/25 hexanes/ethyl acetate) followed by high pressure liquid chromatography [Chirobiotic T, 5 μM, 25 cm×4.6 mm ID, 60/40 buffer (0.1% triethylamine in water titrated to pH 5 with glacial acetic acid)/ethanol] afforded R-[2-(3,4-dichloro-phenyl)-4-methyl-pentanoyl]-urea (120.0 mg, 58.1%) as a white solid: mp 138–140° C.; EI-HRMS m/e calcd for $C_{13}H_{16}Cl_2N_2O_2$ (M$^+$) 302.0589, found 302.0595.

Example 18

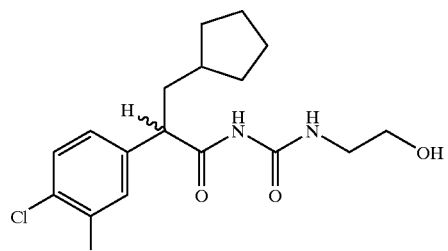

1-[3-Cyclopentyl-2-(3,4-dichloro-phenyl)-propionyl]-3-(2-hydroxy-ethyl)-urea

A solution of 1-allyl-3-[3-cyclopentyl-2-(3,4-dichloro-phenyl)-propionyl]-urea (prepared in Example 12B-e, 75 mg, 0.20 mmol) in dry methylene chloride (10 mL) and methanol (2 drops, needed to solubilize the compound) was cooled to −78° C. and deoxygenated by bubbling argon through the reaction mixture. Ozone was then generated and bubbled through the reaction until a blue color appeared and then the reaction was stirred for five min.

At this time, argon was bubbled through the solution again until the blue color disappeared. Triphenylphosphine (54 mg, 0.20 mmol) was then added and the reaction warmed to 25° C. and stirred for 16 h. At this time, the reaction was concentrated in vacuo and then dissolved in dry methanol (10 mL). The reaction was cooled to 0° C. and then slowly treated with sodium borohydride (31 mg, 0.81 mmol). The reaction was then warmed to 25° C. and stirred for 1 h. It was then quenched with water (10 mL) and extracted with ethyl acetate (3×15 mL). The organics were combined and washed with water (1×15 mL), a saturated aqueous sodium chloride solution (1×15 mL), dried over sodium sulfate, filtered, and concentrated in vacuo. Flash chromatography (Merck Silica gel 60, 230–400 mesh, 1/1 hexanes/ethyl acetate) afforded 1-[3-cyclopentyl-2-(3,4-dichloro-phenyl)-propionyl]-3-(2-hydroxy-ethyl)-urea (48 mg, 64%) as a hygroscopic white solid: EI-HRMS m/e calcd for $C_{17}H_{22}Cl_2N_2O_3$ (M$^+$) 370.1215, found 370.1209.

Example 19

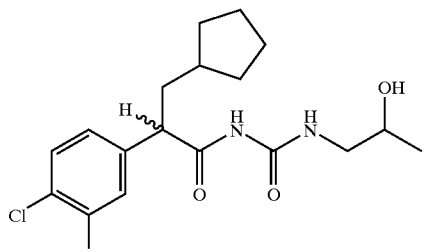

1-[3-Cyclopentyl-2-(3,4-dichloro-phenyl)-propionyl]-3-(2-hydroxy-propyl)-urea

A solution of 1-allyl-3-[3-cyclopentyl-2-(3,4-dichloro-phenyl)-propionyl]-urea (prepared in Example 12B-e, 132 mg, 0.36 mmol) in tetrahydrofuran (10 mL) cooled to 0° C. was treated with a 1M solution of borane-tetrahydrofuran (0.7 mL, 0.72 mmol). The reaction mixture was allowed to warm from 0° C. to 25° C. over 1 h. At this time, the solution was re-cooled to 0° C. and treated with ethanol (2 mL) followed by the slow addition of a mixture of a saturated aqueous sodium bicarbonate solution (6 mL) and 30% hydrogen peroxide (2 mL). The resulting mixture was allowed to slowly warm to 25° C. over 1 h. At this time, the reaction was re-cooled to 0° C. and was slowly quenched with a saturated aqueous sodium sulfite solution (20 mL). This mixture was extracted with ethyl acetate (3×20 mL). The organics were washed with a saturated aqueous sodium chloride solution (1×15 mL), dried over sodium sulfate, and concentrated in vacuo. Flash chromatography (Merck Silica gel 60, 230–400 mesh, 80/20 hexaneslethyl acetate) effected the separation of two spots, the first of the two product spots to elute off the column afforded 1-[3-cyclopentyl-2-(3,4-dichloro-phenyl)-propionyl]-3-(2-hydroxy-propyl)-urea (36 mg, 26%) as a white solid: mp 116.7–119.9° C.; EI-HRMS m/e calcd for $C_{18}H_{24}Cl_2N_2O_3$ ($M^+$) 386.1164, found 386.1173.

Example 20

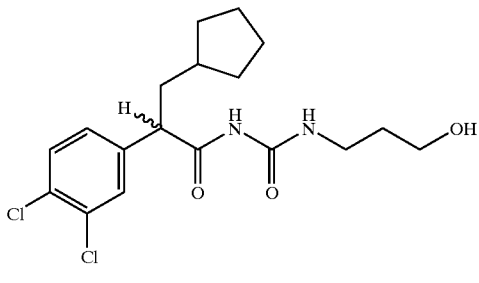

1-[3-Cyclopentyl-2-(3,4-dichloro-phenyl)-propionyl]-3-(3-hydroxy-propyl)-urea

A solution of 1-allyl-3-[3-cyclopentyl-2-(3,4-dichloro-phenyl)-propionyl]-urea (prepared in Example 12B-e, 132 mg, 0.36 mmol) in tetrahydrofuran (10 mL) cooled to 0° C. was treated with a 1M solution of borane-tetrahydrofuran (0.7 mL, 0.72 mmol). The reaction mixture was allowed to slowly warm from 0° C. to 25° C. over 1 h. At this time, the solution was re-cooled to 0° C. and ethanol (2 mL) followed by a mixture of a saturated aqueous sodium bicarbonate solution (6 mL) and 30% hydrogen peroxide (2 mL) was added slowly. This mixture was allowed to slowly warm to 25° C. while stirring for 1 h. At this time, the reaction was re-cooled to 0° C. and slowly quenched with a saturated aqueous sodium sulfite solution (20 mL). This solution was extracted with ethyl acetate (3×20 mL). The organics were washed with a saturated aqueous sodium chloride solution (1×15 mL), dried over sodium sulfate, and concentrated in vacuo. Flash chromatography (Merck Silica gel 60, 230–400 mesh, 80/20 hexanes/ethyl acetate) effected the separation of two spots, the second of the two product spots to elute off the column afforded 1-[3-cyclopentyl-2-(3,4-dichloro-phenyl)-propionyl]-3-(3-hydroxy-propyl)-urea (73 mg, 53%) as a white hygroscopic solid: EI-HRMS m/e calcd for $C_{18}H_{24}Cl_2N_2O_3$ ($M^+$) 386.1164, found 386.1172.

Example 21

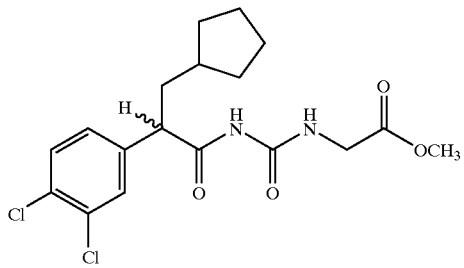

{3-[3-Cyclopentyl-2-(3,4-dichloro-phenyl)-propionyl]-ureido}-acetic acid methyl ester A solution of {3-[3-cyclopentyl-2-(3,4-dichloro-phenyl)-propionyl]-ureido}-acetic acid ethyl ester (prepared in Example 12B-d, 77 mg, 0.19 mmol) in ethanol (5 mL) at 25° C. was treated with a solution of potassium hydroxide (36 mg, 0.65 mmol) in water (1 mL). The reaction mixture was stirred at 25° C. for 2 h. At this time, the reaction was diluted with water (5 mL) and the ethanol was removed in vacuo. The aqueous layer was then acidified to pH=2 with a 1N aqueous hydrochloric acid solution and extracted with methylene chloride (3×15 mL). The organics were then dried over sodium sulfate, filtered, and concentrated in vacuo. Flash chromatography (Merck Silica gel 60, 230–400 mesh, 88/12 chloroform/methanol plus 1% acetic acid) afforded {3-[3-cyclopentyl-2-(3,4-dichloro-phenyl)-propionyl]-ureido}-acetic acid (43 mg, 60%) as a white solid: mp 204.2–206.8° C.; EI-HRMS m/e calcd for $C_{17}H_{20}Cl_2N_2O_4$ ($M^+$) 386.0800, found 386.0795.

A solution of {3-[3-cyclopentyl-2-(3,4-dichloro-phenyl)-propionyl]-ureido}-acetic acid (30 mg, 0.08 mmol) in methanol (5 mL) was treated with concentrated sulfuric acid (4 drops). The reaction was heated to 80° C. for 8 h. At this time, the reaction was cooled to 25° C. and diluted with water (10 mL). This solution was extracted with ethyl acetate (3×20 mL). The organics were washed with a saturated aqueous sodium bicarbonate solution (1×20 mL), a saturated aqueous sodium chloride solution (1×20 mL) and water (1×10 mL), dried over sodium sulfate, filtered, and concentrated in vacuo. Flash chromatography (Merck Silica gel 60, 230–400 mesh, 80/20 hexanes/ethyl acetate) afforded {3-[3-cyclopentyl-2-(3,4-dichloro-phenyl)-propionyl]-ureido}-acetic acid methyl ester (21 mg, 68%) as a white solid:mp 134.5–136.6° C.; EI-HRMS m/e calcd for $C_{18}H_{22}Cl_2N_2O_4$ ($M^+$) 400.0957, found 400.0970.

Example 22

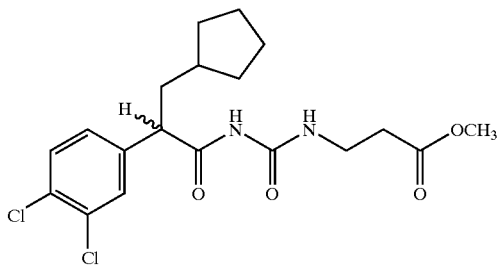

3-{3-[3-Cyclopentyl-2-(3,4-dichloro-phenyl)-propionyl]-ureido}-propionic acid methyl ester A solution of 3-{3-[3-cyclopentyl-2-(3,4-dichloro-phenyl)-propionyl]-ureido}-propionic acid ethyl ester (prepared in Example 12B-c, 94 mg, 0.22 mmol) in ethanol (5 mL) at 25° C. was treated with a solution of potassium hydroxide (43 mg, 0.77 mmol) in water (1 mL). This solution was stirred at 25° C. for 2 h. At this time, the reaction was diluted with water (5 mL) and the ethanol was removed in vacuo. The aqueous layer was acidified to pH=2 with a 1N aqueous hydrochloric acid solution and extracted with methylene chloride (3×15 mL). The organic layers were then dried over sodium sulfate, filtered, and concentrated in vacuo. Flash chromatography (Merck Silica gel 60, 230–400 mesh, 50/50 hexanes/ethyl acetate plus 1% acetic acid) afforded 3-{3-[3-cyclopentyl-2-(3,4-dichloro-phenyl)-propionyl]-ureido}-propionic acid (30 mg, 35%) as a white foam: FAB-HRMS m/e calcd for $C_{18}H_{22}Cl_2N_2O_4$ (M+H)$^+$ 401.1035, found 401.1022.

A solution of 3-{3-[3-cyclopentyl-2-(3,4-dichloro-phenyl)-propionyl]-ureido}-propionic acid (20 mg, 0.05 mmol) in methanol (5 mL) was treated with concentrated sulfuric acid (4 drops). This solution was heated to 80° C. for 8 h. At this time, the reaction was cooled to 25° C. and diluted with water (10 mL). This solution extracted with ethyl acetate (3×20 mL). The organics were washed with a saturated aqueous sodium bicarbonate solution (1×20 mL), a saturated aqueous sodium chloride solution (1×20 mL) and water (1×10 mL), dried over sodium sulfate, filtered, and concentrated in vacuo. Flash chromatography (Merck Silica gel 60, 230–400 mesh, 80/20 hexanes/ethyl acetate) afforded 3-{3-[3-cyclopentyl-2-(3,4-dichloro-phenyl)-propionyl]-ureido}-propionic acid methyl ester (18 mg, 86%) as a white solid: 93.6–95.8° C.: EI-HRMS m/e calcd for $C_{19}H_{24}Cl_2N_2O_4$ (M$^+$) 414.1113, found 414.1114.

Example 23

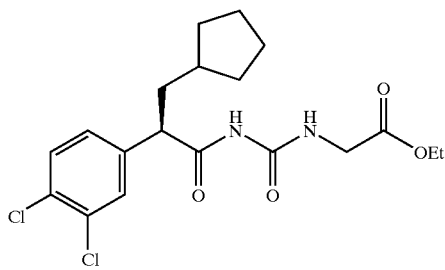

{3-[3-Cyclopentyl-2(R)-(3,4-dichloro-phenyl)-propionyl]-ureido}-acetic acid ethyl ester A solution of 3-cyclopentyl-2(R)-(3,4-dichloro-phenyl)-propionamide (prepared in Example 13, 600 mg, 2.10 mmol) in toluene (15 mL) was treated with ethyl isocyantoacetate (0.35 mL, 3.14 mmol). This solution was heated under reflux for 16 h. At this time, the reaction was cooled to 25° C. and concentrated in vacuo. Flash chromatography (Merck Silica gel 60, 230400 mesh, 90/10 hexanes/ethyl acetate) afforded {3-[3-cyclopentyl-2(R)-(3,4-dichloro-phenyl)-propionyl]-ureido}-acetic acid ethyl ester (525 mg, 60%) as a colorless oil; $[\alpha]^{23}_{589}$=−27.4° (c=0.113, chloroform); EI-HRMS m/e calcd for $C_{19}H_{24}Cl_2N_2O_4$ (M$^+$) 414.1113, found 414.1123.

Example 24

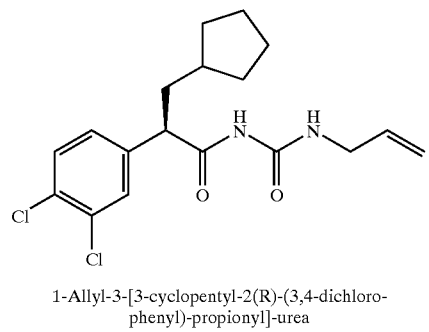

1-Allyl-3-[3-cyclopentyl-2(R)-(3,4-dichloro-phenyl)-propionyl]-urea

A solution of 3-cyclopentyl-2(R)-(3,4-dichloro-phenyl)-propionamide (prepared in Example 13, 1.02 g, 3.55 mmol) in toluene (30 mL) was treated with allyl isocyanate (0.47 mL, 5.33 mmol). This solution was heated to reflux for 16 h. At this time, the reaction was cooled to 25° C. and concentrated in vacuo. Flash chromatography (Merck Silica gel 60, 230–400 mesh, 90/10 hexanes/ethyl acetate) afforded 1-allyl-3-[3-cyclopentyl-2(R)-(3,4-dichloro-phenyl)-propionyl]-urea (1.06 g, 81%) as a colorless oil: $[\alpha]^{23}_{589}$=−25.2° (c=0.151, chloroform); EI-HRMS m/e calcd for $C_{18}H_{22}Cl_2N_2O_2$ (M$^+$) 368.1058, found 368.1054.

Example 25

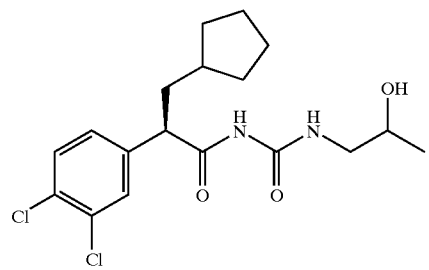

1-[3-Cyclopentyl-2(R)-(3,4-dichloro-phenyl)-propionyl]-3-(2-hydroxy-propyl)-urea A solution of 1-allyl-3-[3-cyclopentyl-2(R)-(3,4-dichloro-phenyl)-propionyl]-urea (prepared in Example 24, 765 mg, 2.07 mmol) in tetrahydrofuran (50 mL) cooled to 0° C. was treated with a 1.0M borane solution in tetrahydrofuran (4.14 mL, 4.14 mmol). The reaction was allowed to warm from 0° C. to 25° C. over 1 h. At this time, the reaction was re-cooled to 0° C. and treated with ethanol (15 mL) followed by a mixture of a saturated aqueous sodium bicarbonate solution (45 mL) and hydrogen peroxide (15 mL). The resulting mixture was allowed to warm from 0° C. to 25° C. over 1 h. The reaction was then slowly quenched with a saturated aqueous sodium sulfite solution and then extracted with ethyl acetate (3×30 mL). The organics were washed with a saturated aqueous sodium chloride solution (1×20 mL), dried over sodium sulfate, filtered, and concentrated in vacuo. Flash chromatography (Merck Silica gel 60, 230–400 mesh, 80/20 hexanes/ethyl acetate) afforded 1-[3-cyclopentyl-2(R)-(3,4-dichloro-phenyl)-propionyl]-3-(2-hydroxy-propyl)-urea (103 mg, 11%) as a white foam: $[\alpha]^{23}_{589}$=−33.0° (c=0.094, chloroform); EI-HRMS m/e calcd for $C_{18}H_{24}Cl_2N_2O_3$ (M$^+$) 386.1164, found 386.1151.

Example 26

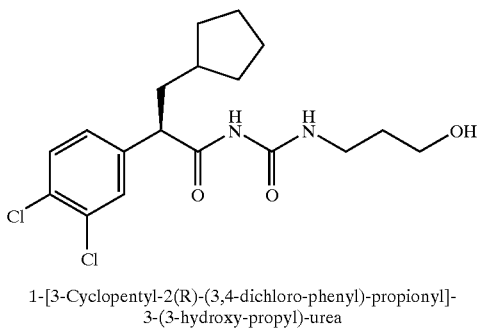

1-[3-Cyclopentyl-2(R)-(3,4-dichloro-phenyl)-propionyl]-
3-(3-hydroxy-propyl)-urea A solution of 1-allyl-3-[3-cyclopentyl-2(R)-(3,4-dichloro-phenyl)-propionyl]-urea (prepared in Example 24, 765 mg, 2.07 mmol) in tetrahydrofuran (50 mL) cooled to 0° C. was treated with a 1.0M borane solution in tetrahydrofuran (4.14 mL, 4.14 mmol). The reaction was allowed to warm from 0° C. to 25° C. over 1 h. At this time, the reaction was re-cooled to 0° C. and treated with ethanol (15 mL) followed by a mixture of a saturated aqueous sodium bicarbonate solution (45 mL) and hydrogen peroxide (15 mL). The resulting mixture was allowed to warm from 0° C. to 25° C. over 1 h. The reaction was then slowly quenched with a saturated aqueous sodium sulfite solution and then extracted with ethyl acetate (3×30 mL). The organics were washed with a saturated aqueous solution of sodium chloride (1×20 mL), dried over sodium sulfate, filtered, and concentrated in vacuo. Flash chromatography (Merck Silica gel 60, 230–400 mesh, 80/20 hexanes/ethyl acetate) afforded 1-[3-cyclopentyl-2-(3,4-dichloro-phenyl)-propionyl]-3-(3-hydroxy-propyl)-urea (173 mg, 22%) as a white foam: $[\alpha]^{23}_{589}=37.3°$ (c=0.075, chloroform); EI-HRMS m/e calcd for $C_{18}H_{24}Cl_2N_2O_3$ (M$^+$) 386.1164, found 386.1154.

Example 27

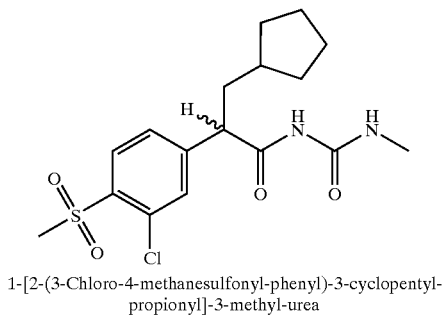

1-[2-(3-Chloro-4-methanesulfonyl-phenyl)-3-cyclopentyl-
propionyl]-3-methyl-urea A solution of aluminum trichloride (34.8 g, 261.4 mmol) in chloroform (120 mL) cooled to 0° C. was treated with a solution of ethyl chlorooxoacetate (18.7 mL, 167.5 mmol) in chloroform (120 mL). The mixture was stirred at 0° C. for 30 min. At this time, a solution of 2-chlorothioanisole (25.0 g, 156.5 mmol) in chloroform (120 mL) was added dropwise to the reaction mixture. It was then allowed to warm to 25° C. and stirred for an additional 3.5 h at 25° C. At this time, the reaction was quenched by the slow addition of water (500 mL) and extracted with chloroform (3×50 mL). The organics were dried over sodium sulfate, filtered, and concentrated in vacuo. Flash chromatography (Merck Silica gel 60, 230–400 mesh, 80/20 hexanes/ethyl acetate) afforded (3-chloro-4-methylsulfanyl-phenyl)-oxo-acetic acid ethyl ester (31.37 g, 77%) as a yellow oil: EI-HRMS m/e calcd for $C_{18}H_{24}Cl_2N_2O_3$ (M$^+$) 386.1164, found 386.1154.

A solution of cylcopentylmethyl triphenylphosphonium iodide (prepared in Example 33, 725 mg, 1.53 mmol) in tetrahydrofuran (10 mL) cooled to 0° C. was treated with a 1.0M solution of sodium bis(trimethylsilyl)amide in tetrahydrofuran (2.14 mL, 2.14 mmol). The reaction was stirred at 0° C. for 45 min. At this time, the reaction was treated with a solution of (3-chloro-4-methylsulfanyl-phenyl)-oxo-acetic acid ethyl ester (355 mg, 1.37 mmol) in tetrahydrofuran (5 mL). The reaction was then warmed to 25° C. and stirred at 25° C. for 20 h. The reaction was then diluted with water (50 mL) and extracted with diethyl ether (3×25 mL). The organics were dried over sodium sulfate, filtered, and concentrated in vacuo. Biotage chromatography (FLASH 12M, Silica, 80/20 hexanes/ethyl acetate) afforded 2-(3-chloro-4-methylsulfanyl-phenyl)-3-cyclopentyl-acrylic acid ethyl ester (267 mg, 60%, 2:1 mixture of E:Z isomers) as a yellow oil and taken on without characterization.

A solution of E:Z isomers of 2-(3-chloro-4-methylsulfanyl-phenyl)-3-cyclopentyl-acrylic acid ethyl ester (100 mg, 0.31 mmol) in methylene chloride (5 mL) cooled to 0° C. was treated with 3-chloroperoxybenzoic acid (80%, 157 mg, 0.73 mmol) and stirred for 3.5 h. The reaction mixture was then diluted with methylene chloride (25 mL). This solution was washed with a saturated aqueous sodium carbonate solution (2×10 mL) and a saturated aqueous sodium chloride solution (2×10 mL). The organics were dried over sodium sulfate, filtered, and concentrated in vacuo. Biotage chromatography (FLASH 12 M, Silica, 80/20 hexanes/ethyl acetate) afforded 2-(3-chloro-4-methanesulfonyl-phenyl)-3-cyclopentyl-acrylic acid ethyl ester (95 mg, 86%, 2:1 mixture of E:Z isomers) as a colorless oil and taken on without characterization.

A solution of E:Z isomers of 2-(3-chloro-4-methanesulfonyl-phenyl)-3-cyclopentyl-acrylic acid ethyl ester (1.04 g, 2.91 mmol), nickel chloride hexahydrate (69 mg, 0.29 mmol) in methanol (25 mL) cooled to 0° C. was treated with sodium borohydride (221 mg, 5.83 mmol) at a rate to maintain the reaction temperature below 20° C. After complete addition of the sodium borohydride, the reaction was stirred at 25° C. for 1.5 h. At this time, the reaction was filtered through celite and washed with methanol. The filtrate was concentrated in vacuo. The residue was diluted with water (15 mL) and extracted with ethyl acetate (3×15 mL). The organics were dried over sodium sulfate, filtered and concentrated in vacuo. Flash chromatography (Merck Silica gel 60, 230–400 mesh, 75/25 hexanes/ethyl acetate) afforded a mixture of 2-(3-chloro-4-methanesulfonyl-phenyl)-3-cyclopentyl-propionic acid methyl ester and 2-(3-chloro-4-methanesulfonyl-phenyl)-3-cyclopentyl-propionic acid ethyl ester (transesterification occurred under the reaction conditions) (937 mg) as a clear colorless oil. (Transesterification occurred under the reaction conditions and the mixture of esters was carried on without characterization)

A solution of 2-(3-chloro-4-methanesulfonyl-phenyl)-3-cyclopentyl-propionic acid methyl ester and 2-(3-chloro-4-methanesulfonyl-phenyl)-3-cyclopentyl-propionic acid ethyl ester (268 mg) and methyl urea (110 mg, 1.5 mmol) in magnesium methoxide in methanol (7.4 wt %, 1.6 mL, 1.1 mmol) was heated to 100° C. for 8 h. At this time, the reaction was concentrated in vacuo. The residue was then dissolved in ethyl acetate (50 mL), filtered through a plug of silica gel, and washed with ethyl acetate (100 mL). The filtrate was concentrated in vacuo. Flash chromatography (Merck Silica gel 60, 230–400 mesh, 60/40 hexanes/ethyl acetate) afforded 1-[2-(3-chloro-4-methanesulfonyl-phenyl)-3-cyclopentyl-propionyl]-3-methyl-urea (55 mg, 19% yield) as a white foam: FAB-HRMS m/e calcd for $C_{17}H_{23}ClN_2O_4S$ (M+H)$^+$387.1145, found 387.1156.

Example 28

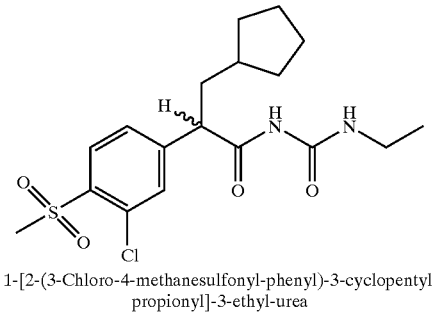

1-[2-(3-Chloro-4-methanesulfonyl-phenyl)-3-cyclopentyl-propionyl]-3-ethyl-urea

A solution of 2-(3-chloro-4-methanesulfonyl-phenyl)-3-cyclopentyl-propionic acid methyl ester and 2-(3-chloro-4-methanesulfonyl-phenyl)-3-cyclopentyl-propionic acid ethyl ester (prepared in Example 27, 937 mg) in ethanol (30 mL) at 25° C. was treated with a solution of potassium hydroxide (733 mg, 13.1 mmol) in water (7 mL). This solution was stirred at 25° C. for 3 h. At this time, the reaction mixture was concentrated in vacuo. The residue was acidified to pH=2 by treatment with a 1N aqueous hydrochloric acid solution. This solution was then extracted with methylene chloride (3×15 mL). The organics were dried over sodium sulfate, filtered, and concentrated in vacuo. Flash chromatography (Merck Silica gel 60, 230–400 mesh, 75/25 hexanes/ethyl acetate plus 1% acetic acid) afforded 2-(3-chloro-4-methanesulfonyl-phenyl)-3-cyclopentyl-propionic acid (787 mg, 82% over two steps) as a white solid: mp 123.9–126.2° C.; FAB-HRMS m/e calcd for $C_{15}H_{19}ClO_4S$ (M+H)$^+$331.0771, found 331.0776.

A solution of 2-(3-chloro-4-methanesulfonyl-phenyl)-3-cyclopentyl-propionic acid (147 mg, 0.44 mmol) in toluene (5 mL) with N,N-dimethylformamide (2 drops) at 25° C. was treated with oxalyl chloride (0.05 mL, 0.53 mmol). The reaction was stirred at 25° C. for 30 min. At this time, the reaction was cooled to −60° C. and treated with ammonium hydroxide (0.50 mL, 3.8 mmol). The resulting suspension was allowed to warm to 25° C. and stirred at 25° C. for 1 h. At this time, the reaction was quenched by the addition of a 2N aqueous hydrochloric acid solution (1 mL) and then extracted with diethyl ether (3×25 mL). The organics were dried over magnesium sulfate, filtered, and concentrated in vacuo. Flash chromatography (Merck Silica gel 60, 230–400 mesh, 65/35 hexanes/ethyl acetate) afforded 2-(3-chloro-4-methanesulfonyl-phenyl)-3-cyclopentyl-propionamide (130 mg, 89%) as a white foam: EI-HRMS m/e calcd for $C_5H_{20}ClNO_3S$ (M$^+$) 329.0852, found 329.0852.

Example 29

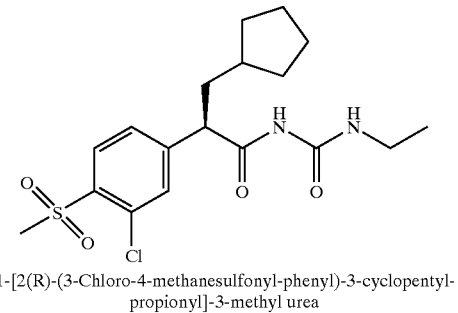

1-[2(R)-(3-Chloro-4-methanesulfonyl-phenyl)-3-cyclopentyl-propionyl]-3-methyl urea A solution of 2-(3-chloro-4-methanesulfonyl-phenyl)-3-cyclopentyl-propionic acid (prepared in Example 28, 6.1 g, 18.3 mmol), (R)-(+)-4-benzyl-2-oxazolidinone (2.83 g, 15.9 mmol), triethylamine (6.68 mL, 47.7 mmol), in toluene (50 mL) heated to 80° C. was treated with pivaloyl chloride (3.55 mL, 28.8 mmol) in toluene (10 mL). The resulting slurry was heated at 80° C. for 36 h. At this time, the reaction was cooled to 20° C. and concentrated in vacuo. The residue was diluted with ethyl acetate (150 mL) washed with a 1N aqueous hydrochloric acid solution (100 mL), a 10% aqueous sodium carbonate solution (100 mL), and a saturated aqueous sodium chloride solution (100 mL). The organics were dried over magnesium sulfate, filtered, and concentrated in vacuo. Flash chromatography (Merck Silica gel 60, 230–400 mesh, 90/5/5 methylene chloride/hexanes/ethyl acetate) afforded 4(R)-benzyl-3-[2(S)-(3-chloro-4-methanesulfonyl-phenyl)-3-cyclopentyl-propionyl]-oxazolidin-2-one (2.08 g, 23%) as a white foam: $[\alpha]^{23}_{589}$=+10.4° (c=0.144, chloroform); FAB-HRMS m/e calcd for $C_{25}H_2SClNO_5S$ (M+H)$^+$490.1455, found 490.1457 and 4(R)-benzyl-3-[2(R)-(3-chloro methanesulfonyl-phenyl)-3-cyclopentyl-propionyl]-oxazolidin-2-one (2.20 g, 25%) as a white foam: $[\alpha]^{23}_{589}$=−93.9° (c=0.165, chloroform); FAB-HRMS m/e calcd for $C_{25}H_{28}ClNO_5S$ (M+H)$^+$490.1455, found 490.1443.

A solution of lithium hydroxide (215 mg, 9.0 mmol) in water (2.8 mL) was treated with a 30% aqueous solution of hydrogen peroxide (2.0 mL, 18 mmol). This lithium hydroperoxide solution was cooled to 0° C. and was then slowly added to a solution of 4(R)-benzyl-3-[2(R)-(3-chloro-4-methanesulfonyl-phenyl)-3-cyclopentyl-propionyl]-oxazolidin-2-one (2.20 g, 4.5 mmol) in tetrahydrofuran (18 mL) and water (5.8 mL) cooled to 0° C. The reaction was stirred at 0° C. for 1.5 h. At this time, the reaction was quenched with a 1.5N aqueous sodium sulfite solution (25 mL) and was further diluted with water (150 mL). This solution was extracted with diethyl ether (3×50 mL). The aqueous layer was then acidified to pH=2 with a 1N aqueous hydrochloric acid solution and extracted with ethyl acetate (3×50 mL). The organics were dried over sodium sulfate, filtered, and concentrated in vacuo. Flash chromatography (Merck Silica gel 60, 230–400 mesh, 75/25 hexanes/ethyl acetate plus 1% acetic acid) afforded 2(R)-(3-chloro-4-methanesulfonyl-phenyl)-3-cyclopentyl-propionic acid (1.26 g, 85%) as a white solid: mp 106.1–108.8° C.; $[\alpha]^{23}_{589}$=−43.0° (c=0.172, chloroform); EI-HRMS m/e calcd for $C_{15}H_{19}ClO_4S$ (M$^+$) 330.0692, found 330.0690.

A solution of 2(R)-(3-chloro-4-methanesulfonyl-phenyl)-3-cyclopentyl-propionic acid (200 mg, 0.61 mmol) in toluene (4.8 mL) and N,N-dimethylformamide (12 μL) at 25° C. was treated with a 2.0 M solution of oxalyl chloride in methylene chloride (0.36 mL, 0.73 mmol). This solution was stirred at 25° C. for 30 min. At this time, the reaction was cooled to −60° C. and treated dropwise with a 30% aqueous ammonium hydroxide solution (0.59 mL, 5.24 mmol). The resulting suspension was allowed to gradually warm to 25° C. and stirred at 25° C. for 1 h. The reaction mixture was then extracted with ethyl acetate (3×25 mL). The organics were dried over magnesium sulfate, filtered and concentrated in vacuo. Flash chromatography (Biotage Flash 40S column, ethyl acetate) afforded 2(R)-(3-chloro-4-methanesulfonyl-phenyl)-3-cyclopentyl-propionamide (175 mg, 88%) as a colorless oil: $[\alpha]^{23}{}_{589}=-45.8°$ (c=0.096, chloroform); EI-HRMS m/e calcd for $C_{15}H_{20}ClNO_3S$ (M$^+$) 329.0852, found 329.0851.

A solution of 2(R)-(3-chloro-4-methanesulfonyl-phenyl)-3-cyclopentyl-propionamide (160 mg, 0.49 mmol) in toluene (5 mL) was treated with methyl isocyanate (0.12 mL, 1.94 mmol). The reaction mixture was then heated at 100° C. for 16 h. At this time, the reaction was concentrated in vacuo. Biotage chromatography (FLASH 40S, Silica, 60/40 hexanes/ethyl acetate) afforded 1-[2(R)-(3-chloro-4-methanesulfonyl-phenyl)-3-cyclopentyl-propionyl]-3-methyl-urea (79 mg, 42%) as a white foam: $[\alpha]^{23}{}_{589}=-8.9°$ (c=0.09, chloroform); FAB-HRMS m/e calcd for $C_{17}H_{23}ClN_2O_4S$ (M+H)+387.1145, found 387.1142.

Example 30

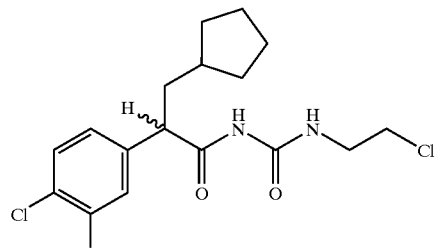

1-(2-Chloro-ethyl)-3-[3-cyclopentyl-2-(3,4-dichlorophenyl)-propionyl]-urea

A solution of 3-cyclopentyl-2-(3,4-dichloro-phenyl)-propionamide (prepared in Example 12, 182 mg, 0.64 mmol) in toluene (10 mL) was treated with 2-chloroethyl isocyanate (0.08 mL, 0.95 mmol). The reaction was heated at reflux for 16 h. At this time, the reaction was cooled to 25° C. and concentrated in vacuo. Flash chromatography (Merck Silica gel 60, 230–400 mesh, 90/10 hexanes/ethyl acetate) afforded 1-(2-chloro-ethyl)-3-[3-cyclopentyl-2-(3,4-dichlorophenyl)-propionyl]-urea (189 mg, 76%) as a colorless oil: EI-HRMS m/e calcd for $C_{17}H_{21}Cl_3N_2O_2$ (M$^+$) 390.0669, found 390.0659.

Example 31

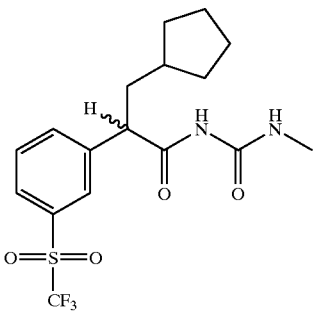

1-[3-Cyclopentyl-2-(3-trifluoromethanesulfonyl-phenyl)-propionyl]-3-methyl-urea

A solution of 3-(trifluoromethylthio)phenylacetic acid (5.00 g, 21.17 mmol) in methanol (50 mL) was treated slowly with concentrated sulfuric acid (10 drops). The resulting reaction mixture was heated to reflux for 18 h. The reaction mixture was allowed to cool to 25° C. and then concentrated in vacuo to remove methanol. The residue was diluted with ethyl acetate (100 mL). The organic phase was washed with a saturated aqueous sodium bicarbonate solution (1×100 mL), dried over magnesium sulfate, and filtered. The filtrate was concentrated in vacuo to afford crude (3-trifluoromethylsulfanyl-phenyl)-acetic acid methyl ester (5.28 g, 99%) as a pale yellow oil which was used without further purification: EI-HRMS m/e calcd for $C_{10}H_9F_3O_2S$ (M$^+$) 250.0275, found 250.0274.

A solution of diisopropylamine (1.5 mL, 10.5 mmol) in dry tetrahydrofuran (27 mL) and 1,3-dimethyl-3,4,5,6-tetrahydro-2(1H)-pyrimidinone (8 mL) cooled to −78° C. was treated with a 2.5M solution of n-butyllithium in hexanes (4.2 mL, 10.5 mmol). The resulting reaction mixture was stirred at −78° C. for 30 min and then treated dropwise with a solution of (3-trifluoromethylsulfanyl-phenyl)-acetic acid methyl ester (2.50 g, 10.0 mmol) in a small amount of tetrahydrofuran. The reaction mixture was allowed to stir at −78° C. for 1 h. At this time, the reaction was treated with a solution of iodomethylcyclopentane (2.10 g, 10.0 mmol) in a small amount of dry tetrahydrofuran. The reaction mixture was allowed to warm to 25° C. where it was stirred for 15 h. The reaction mixture was quenched with water (50 mL) and then partitioned between water (75 mL) and ethyl acetate (75 mL). The organic layer was dried over magnesium sulfate, filtered, and concentrated in vacuo. Flash chromatography (Merck Silica gel 60, 230–400 mesh, 8/1 hexanes/ethyl acetate) afforded 3-cyclopentyl-2-(3-trifluoromethylsulfanyl-phenyl)-propionic acid methyl ester (2.95 g, 89%) as a colorless oil: EI-HRMS m/e calcd for $C_{16}H_{19}F_3O_2S$ (M$^+$) 332.1058, found 332.1047.

A solution of 3-cyclopentyl-2-(3-trifluoromethylsulfanyl-phenyl)-propionic acid methyl ester (2.75 g, 8.27 mmol) in methylene chloride (30 mL) was treated with 3-chloroperoxybenzoic acid (80–85% grade, 4.28 g based on 80%, 20.67 mmol). The reaction mixture was stirred at 25° C. for 6 h. At this time, thin layer chromatography showed the presence of two new lower $R_f$ products. An additional 4.00 g of 3-chloroperoxybenzoic acid was added to the reaction mixture to drive the conversion of the sulfoxide to the sulfone, and the resulting reaction mixture was stirred at 40° C. for 3 d. The reaction mixture was cooled to 25° C. and then partitioned between water (100 mL) and methylene chloride (100 mL). The layers were shaken and separated.

The organic phase was washed twice with a saturated aqueous sodium bicarbonate solution, washed with water, dried over magnesium sulfate, filtered, and concentrated in vacuo. Flash chromatography (Merck Silica gel 60, 230–400 mesh, 1/1 hexanes/methylene chloride) afforded 3-cyclopentyl-2-(3-trifluoromethanesulfonyl-phenyl)-propionic acid methyl ester (2.07 g, 69%) as a colorless oil: EI-HRMS m/e calcd for $C_{16}H_{19}F_3O_4S$ ($M^+$) 364.0956, found 364.0947.

3-Cyclopentyl-2-(3-trifluoromethanesulfonyl-phenyl)-propionic acid methyl ester (500 mg, 1.37 mmol) and methyl urea (305 mg, 4.12 mmol) were treated with a solution of magnesium methoxide in methanol (7.4 wt %, 5.9 mL, 4.12 mmol). The reaction mixture was then concentrated in vacuo to approximately one-half the volume of methanol. The resulting reaction mixture was then heated under reflux for 15 h. The reaction mixture was allowed to cool to 25° C., diluted with ethyl acetate (10 mL), and then filtered through celite. The celite was thoroughly washed with ethyl acetate. The filtrate was concentrated in vacuo. Flash chromatography (Merck Silica gel 60, 230–400 mesh, 3/1 hexanes/ethyl acetate) afforded 1-[3-cyclopentyl-2-(3-trifluoromethanesulfonyl-phenyl)-propionyl]-3-methyl-urea (253 mg, 45%) as a white foam: mp 59–62° C. (foam to gel); EI-HRMS m/e calcd for $C_{17}H_{21}F_3N_2O_4S$ ($M^+$) 406.1174, found 406.1178.

Example 32

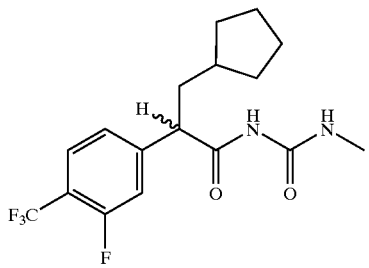

1-[3-Cyclopentyl-2-(3-fluoro-4-trifluoromethyl-phenyl)-propionyl]-3-methyl-urea

A solution of 3-fluoro-4-(trifluoromethyl)phenylacetic acid (2.50 g, 11.25 mmol) in methanol (25 mL) was treated with concentrated sulfuric acid (4 drops). The resulting reaction mixture was heated under reflux for 15 h. The reaction mixture was allowed to cool to 25° C. and then concentrated in vacuo to remove methanol. Flash chromatography (Merck Silica gel 60, 230–400 mesh, 1/1 hexanes/ethyl acetate) afforded (3-fluoro-4-trifluoromethyl-phenyl)-acetic acid methyl ester (2.58 g, 97%) as a colorless oil: EI-HRMS m/e calcd for $C_{10}H_8F_4O_2$ ($M^+$) 236.0460, found 236.0457.

A solution of diisopropylamine (1.5 mL, 10.67 mmol) in dry tetrahydrofuran (24 mL) and 1,3-dimethyl-3,4,5,6-tetrahydro-2(1H)-pyrimidinone (8 mL) cooled to −78° C. was treated with a 2.5M solution of n-butyllithium in hexanes (4.3 mL, 10.67 mmol). The resulting reaction mixture was stirred at −78° C. for 45 min and then treated dropwise with a solution of (3-fluoro-4-trifluoromethyl-phenyl)-acetic acid methyl ester (2.40 g, 10.16 mmol) in a small amount of tetrahydrofuran. The reaction mixture was allowed to stir at −78° C. for 1 h. At this time, the reaction was treated with a solution of iodomethylcyclopentane (2.24 g, 10.67 mmol) in a small amount of dry tetrahydrofuran. The reaction mixture was allowed to warm to 25° C. where it was stirred for 15 h. The reaction mixture was quenched with a saturated aqueous ammonium chloride solution (10 mL) and then partitioned between water (75 mL) and ethyl acetate (75 mL). The layers were shaken and separated. The aqueous layer was further extracted with ethyl acetate (75 mL). The combined organic layers were washed with a saturated aqueous sodium chloride solution, dried over magnesium sulfate, filtered, and concentrated in vacuo. Flash chromatography (Merck Silica gel 60, 230–400 mesh, 5/1 hexanes/ethyl acetate) afforded 3-cyclopentyl-2-(3-fluoro-4-trifluoromethyl-phenyl)-propionic acid methyl ester (2.69 g, 83%) as a colorless oil: EI-HRMS m/e calcd for $C_{16}H_{18}F_4O_2$ ($M^+$) 318.1243, found 318.1250.

3-Cyclopentyl-2-(3-fluoro-4-trifluoromethyl-phenyl)-propionic acid methyl ester (750 mg, 2.36 mmol) and methyl urea (437 mg, 5.90 mmol) were treated with a solution of magnesium methoxide in methanol (7.4 wt %, 14.5 mL, 7.08 mmol). The reaction mixture was then concentrated in vacuo to approximately one-half the volume of methanol. The resulting reaction mixture was then heated under reflux for 15 h. The reaction mixture was allowed to cool to 25° C. and then partitioned between water (75 mL) and ethyl acetate (75 mL). An emulsion formed, and a saturated aqueous sodium chloride solution was added to break down the emulsion. The aqueous layer was further extracted with ethyl acetate (2×75 mL). The combined organic layers were dried over magnesium sulfate, filtered, and concentrated in vacuo to afford a white semi-solid. The semi-solid was treated with a solution of 2/1 hexanes/ethyl acetate, and a white solid formed. The solid was filtered, washed well with hexanes, and dried to afford 1-[3-cyclopentyl-2-(3-fluoro-4-trifluoromethyl-phenyl)-propionyl]-3-methyl-urea (322 mg, 38%) as a white solid: mp 187–189° C.; FAB-HRMS m/e calcd for $C_{17}H_{20}F_4N_2O_2$ $(M+H)^+$ 361.1539, found 361.1549.

Example 33

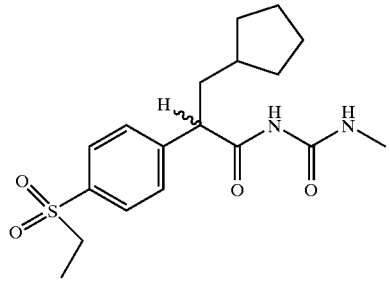

1-[3-Cyclopentyl-2-(4-ethanesulfonyl-phenyl)-propionyl]-3-methyl-urea

A mixture of aluminum chloride (72.35 g, 0.54 mol) in chloroform (181 mL) cooled to 0° C. was stirred until homogeneous. The reaction mixture was then treated slowly with ethyl oxalyl chloride (61 mL, 0.54 mol). The resulting reaction mixture was stirred at 0° C. for 30 min. It was then slowly treated with ethyl phenyl sulfide (25.0 g, 0.18 mol). The solution turned to a wine color and slowly became gum-like. The resulting reaction mixture was then stirred at 0° C. for 2 h. The reaction mixture was slowly poured into a large amount of ice/water. The resulting aqueous layer was extracted with chloroform (3×200 mL). The combined organic layers were dried over sodium sulfate, filtered, and concentrated in vacuo. Flash chromatography (Merck Silica gel 60, 70–230 mesh, 9/1 hexanes/ethyl acetate) afforded (4-ethylsulfanyl-phenyl)-oxo-acetic acid ethyl ester (23.64 g, 55%) as a yellow oil. The material was used without further purification and characterization in subsequent reactions.

A solution of iodomethylcyclopentane (4.60 g, 21.89 mmol) and triphenylphosphine (5.74 g, 21.89 mmol) in acetonitrile (22 mL) was heated under reflux for 2 weeks. The reaction mixture was allowed to cool to 25° C. and then concentrated in vacuo to provide an orange solid. The orange solid was triturated with diethyl ether and then filtered. The solid was washed well with diethyl ether until the washings showed the absence of iodomethylcyclopentane and triphenylphosphine by thin layer chromatography. The solid was allowed to air dry to afford cyclopentylmethyl triphenylphosphonium iodide (8.92 g, 86%) as a light orange solid: mp 195–198° C.; FAB-HRMS m/e calcd for $C_{24}H_{26}P$ $(M+H)^+$345.1772, found 345.1784.

A suspension of cyclopentylmethyl triphenylphosphonium iodide (24.48 g, 51.82 mmol) in tetrahydrofuran (100 mL) cooled to 0° C. was treated dropwise with a 1.0M solution of sodium bis(trimethylsilyl)amide in tetrahydrofuran (52 mL, 51.82 mmol). The bright orange reaction mixture was stirred at 0° C. for 1 h. The reaction mixture was then treated with (4-ethylsulfanyl-phenyl)-oxo-acetic acid ethyl ester (9.50 g, 39.87 mmol). The resulting reaction mixture was allowed to warm to 25° C. where it was stirred for 20 h. The reaction mixture was concentrated in vacuo to remove tetrahydrofuran and then diluted with water (300 mL). The aqueous layer was extracted with ethyl acetate (3×200 mL). The combined organic layers were washed with a saturated aqueous sodium chloride solution (1×200 mL), dried over sodium sulfate, filtered, and concentrated in vacuo. Flash chromatography (Merck Silica gel 60, 70–230 mesh, 19/1 hexanes/ethyl acetate) afforded the 3-cyclopentyl-2-(4-ethylsulfanyl-phenyl)-acrylic acid ethyl ester (6.08 g, 50%) as a yellow oil containing a 1.82:1 mixture of E:Z isomers: FAB-LRMS m/e calcd for $C_{18}H_{24}O_2S$ $(M+H)^+$integer mass 304, found 305.

A solution of 3-cyclopentyl-2-(4-ethylsulfanyl-phenyl)-acrylic acid ethyl ester [5.76 g, 18.92 mmol, E:Z=1.82:1] in methylene chloride (47 mL) was slowly treated with 3-chloroperoxybenzoic acid (57–86% grade, 11.45 g based on 57%, 37.83 mmol). The reaction mixture was stirred at 25° C. for 1 h. The reaction mixture was concentrated in vacuo to remove methylene chloride. The resulting residue was diluted with diethyl ether (300 mL). The organic phase was washed with a saturated aqueous sodium bicarbonate solution (3×200 mL), washed with a saturated aqueous sodium chloride solution (1×200 mL), dried over sodium sulfate, filtered, and concentrated in vacuo. Flash chromatography (Merck Silica gel 60, 230–400 mesh, 3/1 hexanes/ethyl acetate) afforded 3-cyclopentyl-2-(4-ethanesulfonyl-phenyl)-acrylic acid ethyl ester (4.89 g, 77%) as a colorless oil. The product was a 3:1 mixture of (E):(Z) isomers that was used without further purification and characterization.

A solution of 3-cyclopentyl-2-(4-ethanesulfonyl-phenyl)-acrylic acid ethyl ester [4.89 g, 14.53 mmol, (E):(Z)=3:1] in ethanol (36 mL) was slowly treated with 10% palladium on activated carbon (244.5 mg). The reaction mixture was stirred under a positive pressure of hydrogen gas (balloon) at 25° C. and atmospheric pressure for 44 h. The catalyst was then filtered off through a pad of celite, and the celite pad was washed well with ethyl acetate. The filtrate was concentrated in vacuo. Flash chromatography (Merck Silica gel 60, 70–230 mesh, 3/1 hexanes/ethyl acetate) afforded 3-cyclopentyl-2-(4-ethanesulfonyl-phenyl)-propionic acid ethyl ester (3.50 g, 71%) as a colorless viscous oil: FAB-LRMS m/e calcd for $C_{18}H_{26}O_4S$ $(M+H)^+$integer mass 338, found 339.

3-Cyclopentyl-2-(4-ethanesulfonyl-phenyl)-propionic acid ethyl ester (500 mg, 1.48 mmol) and methyl urea (274 mg, 3.70 mmol) were treated with a solution of magnesium methoxide in methanol (7.4 wt %, 6.5 mL, 4.43 mmol). The reaction mixture was then concentrated in vacuo to approximately one-half the volume of methanol. The resulting reaction mixture was then heated under reflux for 2 d. The reaction mixture was allowed to cool to 25° C. and then diluted with ethyl acetate (25 mL). The mixture was filtered through a pad of celite, and the celite pad was washed with ethyl acetate (50 mL). The resulting filtrate was washed with water (40 mL) then the water layer was further extracted with ethyl acetate (40 mL). The combined organic layers were dried over magnesium sulfate, filtered, and concentrated in vacuo to afford a colorless oil. The oil was treated with a solution of 2/1 hexanes/ethyl acetate (10 mL), and a white solid began to precipitate. The suspension was placed in the freezer to enhance crystallization. The solid was filtered to afford 1-[3-cyclopentyl-2-(4-ethanesulfonyl-phenyl)-propionyl]-3-methyl-urea (178 mg, 33%) as a white solid: mp 200–201° C.; FAB-HRMS m/e calcd for $C_{18}H_{26}N_2O_4S$ $(M+H)^+$367.1691, found 367.1697.

Example 34

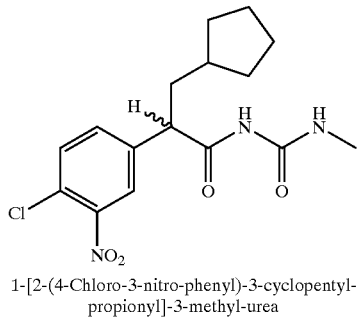

1-[2-(4-Chloro-3-nitro-phenyl)-3-cyclopentyl-propionyl]-3-methyl-urea

A solution of 4-chloro-3-nitrophenylacetamide (2.00 g, 9.32 mmol) in methanol (40 mL) was treated with Amberlyst® 15 ion exchange resin (15.00 g). The resulting reaction mixture was heated under reflux for 64 h. The reaction mixture was allowed to cool to 25° C. and then filtered to remove the Amberlyst® 15 ion exchange resin. The filtrate was concentrated in vacuo. Flash chromatography (Merck Silica gel 60, 230–400 mesh, 3/1 hexanes/ethyl acetate) afforded 4-chloro-3-nitro-phenylacetic acid methyl ester (1.91 g, 89%) as a yellow oil: EI-HRMS m/e calcd for $C_9H_8ClNO_4$ $(M^+)$ 229.0142, found 229.0146.

A solution of diisopropylamine (3.35 mL, 23.9 mmol) in dry tetrahydrofuran (45 mL) and 1,3-dimethyl-3,4,5,6-tetrahydro-2(1H)-pyrimidinone (15 mL) cooled to −78° C. was treated dropwise with a 2.5M solution of n-butyllithium in hexanes (9.56 mL, 23.9 mmol) over a 10 min period. The pale yellow reaction mixture was stirred at −78° C. for 20 min. At this time, the reaction was treated with a solution of 4-chloro-3-nitrophenylacetic acid methyl ester (5.00 g, 21.8 mmol) in a small amount of tetrahydrofuran over a 15 min period. The reaction mixture turned deep purple (almost black) in color. The reaction mixture was then stirred at −78° C. for 1 h. At this time, the reaction was treated with a solution of iodomethylcyclopentane (4.58 g, 21.8 mol) in a small amount of dry tetrahydrofuran. The reaction mixture was then stirred at −78° C. and then allowed to warm to 25° C., where it was stirred for 48 h. The reaction mixture was then quenched with a saturated aqueous ammonium chloride solution (50 mL), and the resulting reaction mixture was concentrated in vacuo to remove tetrahydrofuran. The residue was diluted with ethyl acetate (150 mL) and water (50 mL). The organic phase was washed with a saturated aqueous sodium chloride solution, dried over magnesium sulfate, filtered, and concentrated in vacua. Flash chromatography (Merck Silica gel 60, 230–400 mesh, 4/1 hexanes/ethyl acetate) afforded 2-(4-chloro-3-nitro-phenyl)-3-cyclopentyl-propionic acid methyl ester (2.17 g, 32%) as a yellow oil: EI-HRMS m/e calcd for $C_5H_{18}ClNO_4$ (M+) 311.0924, found 311.0927.

A solution of 2-(4-chloro-3-nitro-phenyl)-3-cyclopentyl-propionic acid methyl ester (260 mg, 0.834 mmol) in tetrahydrofuran (3 mL) at 25° C. was treated with a 0.8M aqueous lithium hydroxide solution (1.25 mL, 1.00 mmol). The reaction mixture was stirred at 25° C. for 15 h. The resulting reaction mixture was partitioned between water (50 mL) and ethyl acetate (50 mL) and then treated with a 1N aqueous hydrochloric acid solution (10 mL). The layers were shaken and separated. The aqueous layer was further extracted with ethyl acetate (50 mL). The combined organic layers were dried over magnesium sulfate, filtered, and concentrated in vacuo to afford 2-(4-chloro-3-nitro-phenyl)-3-cyclopentyl-propionic acid (243 mg, 98%) as a yellow solid which was used without further purification: mp 112–115° C.; FAB-HRMS m/e calcd for $C_{14}H_{16}ClNO_4$ (M+H)+ 298.0847, found 298.0851.

A mixture of 2-(4-chloro-3-nitro-phenyl)-3-cyclopentyl-propionic acid (450 mg, 1.51 mmol) in methylene chloride (4 mL) was treated with N,N-dimethylformamide (1 drop) and then cooled to 0° C. The reaction mixture was then slowly treated with oxalyl chloride (145 µL, 1.66 mmol). The reaction mixture was stirred at 0° C. for 10 min and then stirred at 25° C. for 1 h. The resulting reaction mixture was then treated dropwise with 1,1,1,3,3,3-hexamethyldisilazane (960 µL, 4.53 mmol) and subsequently stirred at 25° C. for 15 h. The resulting reaction mixture was diluted with methylene chloride (10 L) and methanol (10 mL). The organic layer was washed with a 5% aqueous sulfuric acid solution and a saturated aqueous sodium chloride solution. The organic layer was dried over sodium sulfate, filtered, and concentrated in vacuo to afford 2-(4-chloro-3-nitro-phenyl)-3-cyclopentyl-propionamide (295 mg, 67%) as a yellow oil which solidified upon sitting to a yellow solid. The yellow solid was used without further purification: mp 112–114° C.; EI-HRMS m/e calcd for $C_{14}H_{17}ClN_2O_3$ (M+) 296.0927, found 296.0931.

A solution of 2-(4-chloro-3-nitro-phenyl)-3-cyclopentyl-propionamide (200 mg, 0.67 mmol) and methyl isocyanate (382 mg, 6.70 mmol) in toluene (3 mL) was heated under reflux (120° C.) for 15 h. The reaction mixture was allowed to cool to 25° C. and then concentrated in vacuo. Flash chromatography (Merck Silica gel 60, 230–400 mesh, 2/1 hexanes/ethyl acetate) afforded 1-[2-(4-chloro-3-nitro-phenyl)-3-cyclopentyl-propionyl]-3-methyl-urea (139 g, 60%) as a white foam: mp 61–64° C. (foam to gel); FAB-HRMS m/e calcd for $C_{16}H_{20}ClN_3O_4$ (M+H)+ 354.1220, found 354.1232.

Example 35

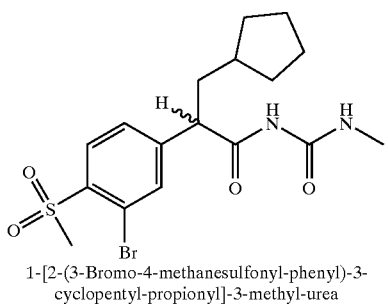

1-[2-(3-Bromo-4-methanesulfonyl-phenyl)-3-cyclopentyl-propionyl]-3-methyl-urea

A solution of 4-(methylthio)phenylacetic acid (21.21 g, 116.38 mmol) in methanol (291 mL) was treated slowly with concentrated sulfuric acid (3 mL). The resulting reaction mixture was heated under reflux for 3 d. The reaction mixture was allowed to cool to 25° C. and then concentrated in vacuo to remove methanol. The resulting residue was diluted with diethyl ether (600 mL). The organic layer was washed with a saturated aqueous sodium bicarbonate solution (3×300 mL) and a saturated aqueous sodium chloride solution (1×300 mL). The organic layer was dried over sodium sulfate, filtered, and concentrated in vacuo to afford (4-methylsulfanyl-phenyl)-acetic acid methyl ester (20.95 g, 92%) as a yellow liquid which was used without further purification: EI-HRMS m/e calcd for $C_{10}H_{12}O_2S$ (M+) 196.0558, found 196.0559.

A solution of (4-methylsulfanyl-phenyl)-acetic acid methyl ester (5.11 g, 26.03 mmol) in carbon tetrachloride (130 mL) was treated slowly with bromine (1.74 mL, 33.84 mmol). The reaction mixture was stirred at 25° C. for 4 h, at which time, thin layer chromatography still indicated the presence of a substantial amount of starting material. The reaction mixture was further treated with more bromine (1.74 mL, 33.84 mmol). The reaction mixture was stirred an additional 4 h at 25° C. and then quenched with a 10% aqueous sodium bisulfite solution (150 mL). The reaction mixture was concentrated in vacuo to remove carbon tetrachloride. The resulting aqueous layer was extracted with ethyl acetate (3×150 mL). The combined organic layers were dried over sodium sulfate, filtered and concentrated in vacuo. Flash chromatography (Merck Silica gel 60, 70–230 mesh, 9/1 hexanes/ethyl acetate) afforded (3-bromo-4-methylsulfanyl-phenyl)-acetic acid methyl ester (6.10 g, 85%) as a light yellow oil: EI-HRMS m/e calcd for $C_{10}H_{11}BrO_2S$ (M+) 273.9663, found 273.9661.

A solution of diisopropylamine (3.4 mL, 24.38 mmol) in dry tetrahydrofuran (21 mL) and 1,3-dimethyl-3,4,5,6-tetrahydro-2(1H)-pyrimidinone (7 mL) cooled to −78° C. was treated with a 2.5M solution of n-butyllithium in hexanes (9.8 mL, 24.38 mmol). The resulting reaction mixture was stirred at −78° C. for 30 min and then treated dropwise with a solution of (3-bromo-4-methylsulfanyl-phenyl)-acetic acid methyl ester (6.10 g, 22.17 mmol) in dry tetrahydrofuran (21 mL) and 1,3-dimethyl-3,4,5,6-tetrahydro-2(1H)-pyrimidinone (7 mL). The resulting reaction mixture was allowed to stir at −78° C. for 1 h. At this time, the reaction was treated with a solution of iodomethylcyclopentane (5.59 g, 26.60 mmol) in a small amount of dry tetrahydrofuran. The resulting reaction mixture was allowed to warm to 25° C. where it was stirred for 15 h. The reaction mixture was quenched with water (300 mL) and then concentrated in vacuo to remove tetrahydrofuran. The remaining aqueous phase was extracted with ethyl acetate (3×150 mL). The combined organic layers were washed with a saturated aqueous sodium chloride solution (1×200 mL), dried over sodium sulfate, filtered, and concentrated in vacuo. Flash chromatography (Merck Silica gel 60, 70–230 mesh, 19/1 hexanes/ethyl acetate) afforded 2-(3-bromo-4-methylsulfanyl-phenyl)-3-cyclopentyl-propionic acid methyl ester (4.52 g, 57%) as a light yellow oil: EI-HRMS m/e calcd for $C_{16}H_{21}BrO_2S$ (M$^+$) 356.0446, found 356.0435.

A solution of 2-(3-bromo-4-methylsulfanyl-phenyl)-3-cyclopentyl-propionic acid methyl ester (1.07 g, 2.99 mmol) in methylene chloride (15 mL) was treated with 3-chloroperoxybenzoic acid (57–86% grade, 1.81 g based on 57%, 5.99 mmol). The reaction mixture was stirred at 25° C. for 3 h. The reaction mixture was concentrated in vacuo to remove methylene chloride. The resulting residue was diluted with diethyl ether (300 mL). The organic phase was washed with a saturated aqueous sodium bicarbonate solution (3×200 mL) and a saturated aqueous sodium chloride solution (1×100 mL), dried over sodium sulfate, filtered, and concentrated in vacuo. Flash chromatography (Merck Silica gel 60, 70–230 mesh, 3/1 hexanes/ethyl acetate) afforded 2-(3-bromo-4-methanesulfonyl-phenyl)-3-cyclopentyl-propionic acid methyl ester (1.09 g, 94%) as a colorless oil: EI-HRMS m/e calcd for $C_{16}H_{19}BrO_4S$ (M$^+$) 388.0344, found 388.0343.

A solution of 2-(3-bromo-4-methanesulfonyl-phenyl)-3-cyclopentyl-propionic acid methyl ester (1.62 g, 4.16 mol) in methanol (10 mL) was treated with a 1N aqueous sodium hydroxide solution (8.7 mL, 8.74 mol). The reaction mixture was stirred at 25° C. for 27 h. The reaction mixture was concentrated in vacuo to remove methanol. The resulting aqueous residue was acidified to pH=2 with a 10% aqueous hydrochloric acid solution and then extracted with ethyl acetate (1×400 mL). The organic layer was washed with water (1×300 mL) and washed with a saturated aqueous sodium chloride solution (1×300 mL). The organic layer was then dried over sodium sulfate, filtered, and concentrated in vacuo to afford 2-(3-bromo-4-methanesulfonyl-phenyl)-3-cyclopentyl-propionic acid (1.39 g, 89%) as a white solid which was used without further purification: mp 149–150° C.; FAB-HRMS m/e calcd for $C_{15}H_{19}BrO_4S$ (M+H)$^+$ 375.0266, found 375.0274.

A mixture of 2-(3-bromo-4-methanesulfonyl-phenyl)-3-cyclopentyl-propionic acid (400 mg, 1.07 mmol) in methylene chloride (4 mL) cooled to 0° C. was treated with N,N-dimethylformamide (2 drops) followed by oxalyl chloride (100 µL, 1.18 mmol). The reaction mixture was stirred at 0° C. for 10 min and then stirred at 25° C. for 1 h. The resulting reaction mixture was then treated dropwise with 1,1,1,3,3,3-hexamethyldisilazane (680 µL, 3.21 mmol) and subsequently stirred at 25° C. for 15 h. The reaction mixture was then diluted with methylene chloride (20 mL) and methanol (20 mL). The organic layer was washed with a 5% aqueous sulfuric acid solution (1×40 mL) and a saturated aqueous sodium chloride solution. The organic layer was dried over magnesium sulfate, filtered, and concentrated in vacuo to afford 2-(3-bromo-4-methanesulfonyl-phenyl)-3-cyclopentyl-propionamide (271 mg, 68%) as a white foam. The white foam was used without further purification: mp 60–63° C.; EI-HRMS m/e calcd for $C_{15}H_{20}BrNO_3S$ (M$^+$) 373.0347, found 373.0348.

A solution of 2-(3-bromo-4-methanesulfonyl-phenyl)-3-cyclopentyl-propionamide (200 mg, 0.53 mmol) and methyl isocyanate (61 mg, 1.07 mmol) in toluene (1 mL) was heated under reflux for 24 h. The reaction mixture turned very cloudy with the forming of a white precipitate. The reaction mixture was allowed to cool to 25° C. and then treated with hexanes. The reaction mixture was placed in the freezer for 1 h then filtered. The white solid was washed with cold hexanes to afford 1-[2-(3-bromo-4-methanesulfonyl-phenyl)-3-cyclopentyl-propionyl]-3-methyl-urea (100 mg, 44%) as a white solid: mp 259–260° C.; FAB-HRMS m/e calcd for $C_{17}H_{23}BrN_2O_4S$ (M+H)$^+$431.0641, found 431.0646.

Example 36

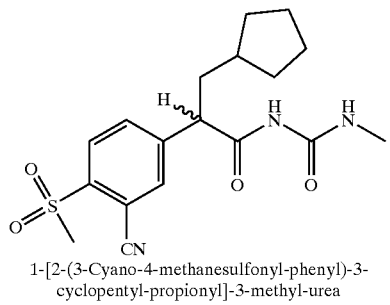

1-[2-(3-Cyano-4-methanesulfonyl-phenyl)-3-cyclopentyl-propionyl]-3-methyl-urea

A solution of 4-(methylthio)phenylacetic acid (21.21 g, 116.38 mmol) in methanol (291 mL) was treated slowly with concentrated sulfuric acid (3 mL). The resulting reaction mixture was heated under reflux for 3 d. The reaction mixture was allowed to cool to 25° C. and then concentrated in vacuo to remove methanol. The resulting residue was diluted with diethyl ether (600 mL). The organic layer was washed with a saturated aqueous sodium bicarbonate solution (3×300 mL) and a saturated aqueous sodium chloride solution (1×300 mL). The organic layer was dried over sodium sulfate, filtered, and concentrated in vacuo to afford (4-methylsulfanyl-phenyl)-acetic acid methyl ester (20.95 g, 92%) as a yellow liquid which was used without further purification: EI-HRMS m/e calcd for $C_{10}H_{12}O_2S$ (M$^+$) 196.0558, found 196.0559.

A solution of (4-methylsulfanyl-phenyl)-acetic acid methyl ester (5.11 g, 26.03 mmol) in carbon tetrachloride (130 mL) was treated slowly with bromine (1.74 mL, 33.84 mmol). The reaction mixture was stirred at 25° C. for 4 h, at which time, thin layer chromatography still indicated the presence of a substantial amount of starting material. The reaction mixture was further treated with more bromine (1.74 mL, 33.84 mmol). The reaction mixture was stirred an additional 4 h at 25° C. and then quenched with a 10% aqueous sodium bisulfite solution (150 mL). The reaction mixture was concentrated in vacuo to remove carbon tetrachloride. The resulting aqueous layer was extracted with ethyl acetate (3×150 mL). The combined organic layers were dried over sodium sulfate, filtered and concentrated in vacuo. Flash chromatography (Merck Silica gel 60, 70–230 mesh, 9/1 hexanes/ethyl acetate) afforded (3-bromo-4-methylsulfanyl-phenyl)-acetic acid methyl ester (6.10 g, 85%) as a light yellow oil: EI-HRMS m/e calcd for $C_{10}H_{11}BrO_2S$ (M$^+$) 273.9663, found 273.9661.

A solution of diisopropylamine (3.4 mL, 24.38 mmol) in dry tetrahydrofuran (21 mL) and 1,3-dimethyl-3,4,5,6-tetrahydro-2(1H)-pyrimidinone (7 mL) cooled to −78° C. was treated with a 2.5M solution of n-butyllithium in hexanes (9.8 mL, 24.38 mmol). The resulting reaction mixture was stirred at −78° C. for 30 min and then treated dropwise with a solution of (3-bromo-4-methylsulfanyl-phenyl)-acetic acid methyl ester (6.10 g, 22.17 mmol) in dry tetrahydrofuran (21 mL) and 1,3-dimethyl-3,4,5,6- tetrahydro-2(1H)-pyrimidinone (7 mL). The resulting reaction mixture was allowed to stir at −78° C. for 1 h. At this time, the reaction was treated with a solution of iodomethylcyclopentane (5.59 g, 26.60 mmol) in a small amount of dry tetrahydrofuran. The reaction mixture was allowed to warm to 25° C. where it was stirred for 15 h. The reaction mixture was quenched with water (300 mL) and then concentrated in vacuo to remove tetrahydrofuran. The remaining aqueous phase was extracted with ethyl acetate (3×150 mL). The combined organic layers were washed with a saturated aqueous sodium chloride solution (1×200 mL), dried over sodium sulfate, filtered, and concentrated in vacuo. Flash chromatography (Merck Silica gel 60, 70–230 mesh, 19/1 hexanes/ethyl acetate) afforded 2-(3-bromo-4-methylsulfanyl-phenyl)-3-cyclopentyl-propionic acid methyl ester (4.52 g, 57%) as a light yellow oil: EI-HRMS m/e calcd for $C_{16}H_{21}BrO_2S$ (M$^+$) 356.0446, found 356.0435.

A solution of 2-(3-bromo-4-methylsulfanyl-phenyl)-3-cyclopentyl-propionic acid methyl ester (1.07 g, 2.99 mmol) in methylene chloride (15 mL) was treated with 3-chloroperoxybenzoic acid (57–86% grade, 1.81 g based on 57%, 5.99 mmol). The reaction mixture was stirred at 25° C. for 3 h. The reaction mixture was concentrated in vacuo to remove methylene chloride. The resulting residue was diluted with diethyl ether (300 mL). The organic phase was washed with a saturated aqueous sodium bicarbonate solution (3×200 mL) and a saturated aqueous sodium chloride solution (1×100 mL), dried over sodium sulfate, filtered, and concentrated in vacuo. Flash chromatography (Merck Silica gel 60, 70–230 mesh, 3/1 hexanes/ethyl acetate) afforded 2-(3-bromo-4-methanesulfonyl-phenyl)-3-cyclopentyl-propionic acid methyl ester (1.09 g, 94%) as a colorless oil: EI-HRMS m/e calcd for $C_{16}H_{19}BrO_4S$ (M$^+$) 388.0344, found 388.0343.

A mixture of 2-(3-bromo-4-methanesulfonyl-phenyl)-3-cyclopentyl-propionic acid methyl ester (990.0 mg, 2.54 mmol) and copper(I) cyanide (273.3 mg, 3.05 mmol) in dry N,N-dimethylformamide (2.5 mL) was heated under reflux for 4 h. The reaction was allowed to cool to 25° C., and the crude reaction mixture was directly purified without further chemical work-up. Flash chromatography (Merck Silica gel 60, 70–230 mesh, 100% hexanes then 3/1 hexanes/ethyl acetate) afforded 2-(3-cyano-4-methanesulfonyl-phenyl)-3-cyclopentyl-propionic acid methyl ester (646.5 mg, 76%) as a pale yellow oil: EI-HRMS m/e calcd for $C_{17}H_{21}NO_4S$ (M$^+$) 335.1191, found 335.1185.

A solution of 2-(3-cyano-4-methanesulfonyl-phenyl)-3-cyclopentyl-propionic acid methyl ester (4.84 g, 14.4 mol) in tetrahydrofuran (25 mL) was treated with a 0.8 M aqueous lithium hydroxide solution (27 mL, 21.6 mmol). The reaction mixture was stirred at 25° C. for 2.5 h. The reaction mixture was partitioned between water and ethyl acetate and then acidified to pH=2 with a 10% aqueous hydrochloric acid solution. The layers were shaken and separated. The resulting organic layer was washed with a saturated aqueous sodium chloride solution, dried over magnesium sulfate, filtered, and concentrated in vacuo to afford crude 2-(3-cyano-4-methanesulfonyl-phenyl)-3-cyclopentyl-propionic acid (3.80 g, 82%) as a pale yellow oil that solidified to a pale yellow solid. An analytical sample was obtained by recrystallization from ethyl acetate to afford 2-(3-cyano-4-methanesulfonyl-phenyl)-3-cyclopentyl-propionic acid as a white solid: mp 180–181° C.; EI-HRMS m/e calcd for $C_{16}H_{19}NO_4S$ (M$^+$) 321.1034, found 321.1039.

A mixture of 2-(3-cyano-4-methanesulfonyl-phenyl)-3-cyclopentyl-propionic acid (200 mg, 0.62 mmol) in methylene chloride (2 mL) cooled to 0° C. was treated with N,N-dimethylformamide (2 drops). The reaction mixture was then slowly treated with oxalyl chloride (60 μL, 0.69 mmol). The reaction mixture was stirred at 0° C. for 10 min and then stirred at 25° C. for 1.5 h. The resulting reaction mixture was then treated dropwise with 1,1,1,3,3,3-hexamethyldisilazane (395 μL, 1.87 mmol) and subsequently stirred at 25° C. for 15 h. The reaction mixture was then partitioned between methylene chloride (20 mL), methanol (15 mL), and a 5% aqueous sulfuric acid solution (25 mL). The organic layer was washed with a saturated aqueous sodium chloride solution, dried over magnesium sulfate, filtered, and concentrated in vacuo. Flash chromatography (Merck Silica gel 60, 230–400 mesh, 1/3 hexanes/ethyl acetate) afforded 2-(3-cyano-4-methanesulfonyl-phenyl)-3-cyclopentyl-propionamide (141 mg, 70%) as a white foam: mp 67–70° C. (foam to gel); EI-HRMS m/e calcd for $C_{16}H_{20}N_2O_3S$ (M$^+$) 320.1195, found 320.1195.

A solution of 2-(3-cyano-4-methanesulfonyl-phenyl)-3-cyclopentyl-propionamide (135 mg, 0.42 mmol) and methyl isocyanate (72 mg, 1.26 mmol) in toluene (1 mL) was heated under reflux for 15 h. The reaction mixture was allowed to cool to 25° C. and then concentrated in vacuo to afford a yellow semi-solid. The semi-solid was treated with a solution of 2/1 hexanes/ethyl acetate (3 mL) and a white precipitate formed. The suspension was placed in the freezer for 1 h and then filtered to afford 1-[2-(3-cyano-4-methanesulfonyl-phenyl)-3-cyclopentyl-propionyl]-3-methyl-urea (55 mg, 35%) as a white solid: mp 237–239° C.; FAB-HRMS m/e calcd for $C_{18}H_{23}N_3O_4S$ (M+H)$^+$ 378.1487, found 378.1483.

Example 37

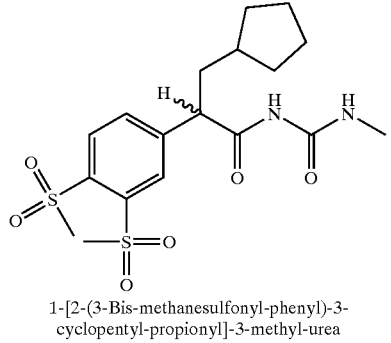

1-[2-(3-Bis-methanesulfonyl-phenyl)-3-cyclopentyl-propionyl]-3-methyl-urea

A solution of 3,4-difluorophenylacetic acid (5.00 g, 29.05 mmol) in methanol (73 mL) was slowly treated with concentrated sulfuric acid (4 mL). The resulting reaction mixture was heated under reflux for 65 h. The reaction mixture was allowed to cool to 25° C. and then concentrated in vacuo to remove methanol. The resulting residue was slowly diluted with a saturated aqueous sodium bicarbonate solution (300 mL) and then extracted with ethyl acetate (1×300 mL). The organic layer was dried over magnesium sulfate, filtered, and concentrated in vacuo to afford (3,4-difluoro-phenyl)-acetic acid methyl ester (5.38 g, 99%) as a yellow oil which was used without further purification.

A solution of sodium thiomethoxide (6.39 g, 86.69 mmol) in dimethyl sulfoxide (72 mL) was treated with (3,4-difluoro-phenyl)-acetic acid methyl ester (5.38 g, 28.89 mmol). The reaction mixture was stirred at 25° C. for 2 h and then at 70° C. for 15 min. At this time, thin layer chromatography indicated the absence of starting material and the presence of a very polar new product. The reaction indicated that the ester hydrolyzed to the acid upon heating. The resulting reaction mixture was allowed to cool to 25° C. The reaction mixture was then treated with a 10% aqueous hydrochloric acid solution (200 mL) and then extracted with chloroform (3×200 mL). The combined organic layers were dried over magnesium sulfate, filtered, and concentrated in vacuo to afford a yellow oil. This yellow oil was dissolved in methanol (100 mL) and then slowly treated with concentrated sulfuric acid (5 mL). The resulting reaction mixture was heated under reflux for 3 h. The reaction mixture was allowed to cool to 25° C. and then concentrated in vacuo to remove methanol. The resulting residue was slowly diluted with a saturated aqueous sodium bicarbonate solution (300 mL) and then extracted with ethyl acetate (1×300 mL). The organic layer was dried over magnesium sulfate, filtered, and concentrated in vacuo to afford an inseparable, isomeric mixture of (3-fluoro-4-methylsulfanyl-phenyl)-acetic acid methyl ester and (4-fluoro-3-methylsulfanyl-phenyl)-acetic acid methyl ester as a yellow oil (4.65 g, 75%) which was used without further purification and characterization.

A solution of the inseparable, isomeric mixture of (3-fluoro-4-methylsulfanyl-phenyl)-acetic acid methyl ester and (4-fluoro-3-methylsulfanyl-phenyl)-acetic acid methyl ester (4.44 g, 20.72 mmol) in methylene chloride (103 mL) was slowly treated with 3-chloroperoxybenzoic acid (57–86% grade, 13.80 g based on 57%, 45.59 mmol). The reaction mixture was stirred at 25° C. for 4 h. The reaction mixture was concentrated in vacuo to remove methylene chloride. The resulting residue was diluted with ethyl acetate (300 mL). The organic phase was washed with a saturated aqueous sodium bicarbonate solution (1×200 mL) and a saturated aqueous sodium chloride solution (1×200 mL), dried over magnesium sulfate, filtered, and concentrated in vacuo. Flash chromatography (Merck Silica gel 60, 70–230 mesh, 20/1 methylene chloride/ethyl acetate) afforded an inseparable, isomeric mixture of (3-fluoro-4-methanesulfonyl-phenyl)-acetic acid methyl ester and (4-fluoro-3-methanesulfonyl-phenyl)-acetic acid methyl ester as a colorless liquid (3.31 g, 65%) which was used without further purification and characterization.

A solution of the inseparable, isomeric mixture of (3-fluoro-4-methanesulfonyl-phenyl)-acetic acid methyl ester and (4-fluoro-3-methanesulfonyl-phenyl)-acetic acid methyl ester (2.28 g, 9.26 mmol) in dimethyl sulfoxide (23 mL) was treated with sodium thiomethoxide (1.37 g, 18.52 mmol). The reaction mixture was stirred at 25° C. for 4 h and then quenched with a 10% aqueous hydrochloric acid solution. The aqueous layer was extracted with chloroform (1×400 mL), dried over magnesium sulfate, filtered, and concentrated in vacuo. Flash chromatography (Merck Silica gel 60, 70–230 mesh, 3/2 hexanes/ethyl acetate) afforded an inseparable, isomeric mixture of (3-methanesulfonyl-4-methylsulfanyl-phenyl)-acetic acid methyl ester and (4-methanesulfonyl-3-methylsulfanyl-phenyl)-acetic acid methyl ester as a yellow liquid (2.19 g, 86%) which was used without further purification and characterization.

A solution of the inseparable, isomeric mixture of (3-methanesulfonyl-4-methylsulfanyl-phenyl)-acetic acid methyl ester and (4-methanesulfonyl-3-methylsulfanyl-phenyl)-acetic acid methyl ester (2.19 g, 7.98 mmol) in methylene chloride (20 mL) was slowly treated with 3-chloroperoxybenzoic acid (57–86% grade, 6.41 g based on 57%, 31.93 mmol). The reaction mixture was stirred at 25° C. for 5 h and then slowly quenched with a 1.5N aqueous sodium sulfite solution. The resulting reaction mixture was extracted with methylene chloride (300 mL). The organic phase was dried over magnesium sulfate, filtered, and concentrated in vacuo. Flash chromatography (Merck Silica gel 60, 70–230 mesh, 10/1 methylene chloride/ethyl acetate) afforded (3,4-bis-methanesulfonyl-phenyl)-acetic acid methyl ester (1.89 g, 77%) as a white solid: mp 157–158° C.; EI-HRMS m/e calcd for $C_{11}H_{14}O_6S_2$ (M+) 306.0232, found 306.0234.

A solution of diisopropylamine (951 μL, 6.79 mmol) in dry tetrahydrofuran (6 mL) and 1,3-dimethyl-3,4,5,6-tetrahydro-2(1H)-pyrimidinone (2 mL) was cooled to −78° C. under nitrogen and then treated with a 2.5M solution of n-butyllithium in hexanes (2.5 mL, 6.79 mmol). The resulting reaction mixture was stirred at −78° C. for 30 min and then treated dropwise with a solution of (3,4-bis-methanesulfonyl-phenyl)-acetic acid methyl ester (1.89 g, 6.17 mmol) in dry tetrahydrofuran (12 mL) and 1,3-dimethyl-3,4,5,6-tetrahydro-2(1H)-pyrimidinone (4 mL). The resulting reaction mixture was allowed to stir at −78° C. for 1 h. At this time, the reaction was treated with a solution of iodomethylcyclopentane (1.56 g, 7.40 mmol) in a small amount of dry tetrahydrofuran. The reaction mixture was allowed to warm to 25° C. where it was stirred for 64 h. The reaction mixture was quenched with water (150 mL) and then concentrated in vacuo to remove tetrahydrofuran.

The remaining residue was further diluted with water (100 mL) and then extracted with ethyl acetate (1×250 mL). The organic layer was washed with a saturated aqueous sodium chloride solution (1×100 mL), dried over magnesium sulfate, filtered, and concentrated in vacuo. Flash chromatography (Merk Silica gel 60, 70–230 mesh, 3/1 hexanes/ethyl acetate) afforded 2-(3,4-bis-methanesulfonyl-phenyl)-3-cyclopentyl-propionic acid methyl ester (1.61 g, 67%) as a yellow oil: EI-HRMS m/e calcd for $C_{17}H_{24}O_6S_2$ (M+) 388.1014, found 388.1014.

2-(3,4-Bis-methanesulfonyl-phenyl)-3-cyclopentyl-propionic acid methyl ester (375 mg, 0.97 mmol) and methyl urea (214 mg, 2.90 mmol) were treated with a solution of magnesium methoxide in methanol (7.4 wt %, 4.2 mL, 2.90 mmol). The reaction mixture was then concentrated in vacuo to approximately one-half the volume of methanol. The resulting reaction mixture was then heated under reflux for 48 h. The reaction mixture was allowed to cool to 25° C., diluted with ethyl acetate (5 mL), and then filtered through celite. The celite was thoroughly washed with ethyl acetate. The filtrate was concentrated in vacuo. Flash chromatography (Merck Silica gel 60, 230–400 mesh, 1/2 hexanes/ethyl acetate) afforded 1-[2-(3,4-bis-methanesulfonyl-phenyl)-3-cyclopentyl-propionyl]-3-methyl-urea (65 mg, 16%) as a white solid: mp 220–222° C.; EI-HRMS m/e calcd for $C_{18}H_{26}N_2O_6S_2$ (M+) 430.1232, found 430.1231.

Example 38

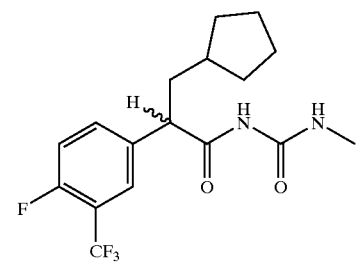

1-[3-Cyclopentyl-2-(4-fluoro-3-trifluoromethyl-phenyl)-propionyl]-3-methyl-urea

A solution of freshly prepared lithium diisopropylamide (35.3 mL of a 0.31 M stock solution, 10.9 mmol) cooled to −78° C. was treated with (4-fluoro-3-trifluoromethyl-phenyl)-acetic acid (1.11 g, 5.0 mmol) in tetrahydrofuran/1,3-dimethyl-3,4,5,6-tetrahydro-2(1H)-pyrimidinone (12.4 mL, 3:1). The resulting solution was stirred at −78° C. for 1 h. At this time, the reaction was treated with a solution of iodomethylcyclopentane (1.16 g, 5.52 mmol) in 1,3-dimethyl-3,4,5,6-tetrahydro-2(1H)-pyrimidinone (1.2 mL). The reaction mixture was stirred at −78° C. for 4 h. The reaction was then warmed to 25° C. and was stirred at 25° C. for 48 h. This solution was then quenched by the slow addition of the reaction mixture to an aqueous solution of 2N hydrochloric acid (50 mL). The product was extracted into ethyl acetate (3×100 mL) and diethyl ether (1×50 mL). The organic layers were dried over magnesium sulfate and sodium sulfate, filtered, and concentrated in vacuo. Flash chromatography (Merck Silica gel 60, 230–400 mesh, 50/50 hexanes/ethyl acetate with acetic acid) afforded 3-cyclopentyl-2-(4-fluoro-3-trifluoromethyl-phenyl)-propionic acid (1.28 g, 84.3%) as a white solid: mp 66–68° C.: EI-HRMS m/e calcd for $C_{15}H_{16}F_4O_2$ ($M^+$) 305.1165, found 305.1174.

A solution 3-cyclopentyl-2-(4-fluoro-3-trifluoromethyl-phenyl)-propionic acid (304 mg, 1.0 mmol) in methylene chloride (10 mL) and N,N-dimethylformamide (1 drop) was cooled to 0° C. and then treated with a 2.0M solution of oxalyl chloride in methylene chloride (1.5 mL, 3.0 mmol). The reaction was stirred for 30 min at 0° C. At this time, 1,1,1,3,3,3-hexamethyldisilazane (2.0 mL, 9.5 mmol) was added to the reaction mixture. The reaction was allowed to slowly warm to 25° C. and then stirred at 25° C. for 16 h. The reaction mixture was then treated with methanol (3 mL) and diluted with methylene chloride (35 mL). The resulting mixture was washed with a 5% aqueous sulfuric acid solution (2×10 mL), water (1×25 mL), and a saturated aqueous sodium chloride solution (3×25 mL). The organic layers were dried over sodium sulfate, filtered, and concentrated in vacuo to afford 3-cyclopentyl-2-(4-fluoro-3-trifluoromethyl-phenyl)-propionamide (333 mg, 92.5%) as a pale yellow oil: EI-HRMS m/e calcd for $C_{15}H_{17}F_4NO$ ($M^+$) 303.1246, found 303.1252.

A solution of 3-cyclopentyl-2-(4-fluoro-3-trifluoromethyl-phenyl)-propionamide (303 mg, 1.0 mmol) in toluene (5 mL) was treated with methyl isocyanate (0.59 mL, 10 5 mmol). The resulting solution was heated to reflux for 24 h. At this time, the reaction was concentrated in vacuo. Flash chromatography (Merck Silica gel 60, 230–400 mesh, 50/50 hexanes/ethyl afforded 1-[3-cyclopentyl-2-(4-fluoro-3-trifluoromethyl-phenyl)-propionyl]-3-methyl-urea (360 mg, 49.2%) as a pale yellow oil: FAB-HRMS m/e calcd for $C_{17}H_{20}F_4N_2O_2$ $(M+H)^+$ 361.1539, found 361.1534.

Example 39

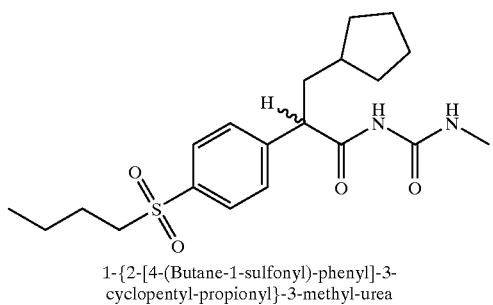

1-{2-[4-(Butane-1-sulfonyl)-phenyl]-3-cyclopentyl-propionyl}-3-methyl-urea

A solution of freshly prepared lithium diisopropylamide (430.55 mL of a 0.3M stock solution, 129.16 mmol) cooled to −78° C. was treated with (4-nitro-phenyl)-acetic acid ethyl ester (26.32 g, 125.83 mmol) in tetrahydrofuran/hexamethylphosphoramide (312.5 mL, 3:1). The resulting solution was stirred at −78° C. for 45 min. At this time, the reaction was treated with a solution of iodomethylcyclopentane (27.75 g, 132.1 mmol) in hexamethylphosphoramide (27.75 mL). The mixture was stirred at −78° C. for 4 h. The reaction was then warmed to 25° C. and was stirred at 25° C. for 16 h. The reaction mixture was then quenched by the dropwise addition of a saturated aqueous ammonium chloride solution (250 mL). This mixture was concentrated in vacuo, diluted with water (250 mL), and extracted with ethyl acetate (3×300 mL). The organics were washed with a saturated aqueous lithium chloride solution (2×250 mL), dried over magnesium sulfate, filtered, and concentrated in vacuo. Flash chromatography (Merck Silica gel 60, 230–400 mesh, 98/2 hexanes/ethyl acetate) afforded 3-cyclopentyl-2-(4-nitro-phenyl)-propionic acid ethyl ester (28.30 g, 77.2%) as an yellow oil: EI-HRMS m/e calcd for $C_{16}H_{21}NO_4$ ($M^+$) 291.1470, found 291.1470.

A solution of 3-cyclopentyl-2-(4-nitro-phenyl)-propionic acid ethyl ester (7.37 g, 25.3 mmol) in ethyl acetate (316 mL) was treated with 10% palladium on activated carbon (500 mg). The reaction mixture was stirred under hydrogen gas at 60 psi at 25° C. for 18 h. The catalyst was then filtered off through a pad of celite (ethyl acetate). The filtrate was concentrated in vacuo to give 2-(4-amino-phenyl)-3-cyclopentyl-propionic acid ethyl ester (3.52 g, 53.3%) as a yellow oil: EI-HRMS m/e calcd for $C_{16}H_{23}NO_2$ ($M^+$) 261.1727, found 261.1727.

A mixture of concentrated hydrochloric acid (0.38 mL) and ice (380 mg) cooled to 0° C. was treated with 2-(4-amino-phenyl)-3-cyclopentyl-propionic acid ethyl ester (497 mg, 1.90 mmol). After 5 min, a solution of sodium nitrite (139 mg, 2.0 mmol) in water (0.31 mL) was added to the reaction mixture. The resulting solution was stirred at 0° C. for 5 min. At this time, this solution was added to a solution of n-butyl mercaptan (0.23 mL, 2.20 mmol) in water (0.4 mL) warmed to 45° C. The reaction was stirred at 45° C. for 3 h. At this time, the reaction was diluted with water (50 mL) and extracted with methylene chloride (3×50 mL). The organics were dried over sodium sulfate, filtered, and concentrated in vacuo. The crude brown oil (588 mg) in methylene chloride (16.5 mL) was cooled to 0° C. and treated with 3-chloroperoxybenzoic acid (80–85% grade, 1.5 g, 8.78 mmol). The reaction mixture was stirred at 25° C. for 48 h. At this time, the reaction was diluted with methylene chloride (100 mL). This solution was washed with a saturated aqueous sodium bisulfite solution (1×100 mL), a saturated aqueous sodium chloride solution (1×100 mL), a saturated aqueous sodium bicarbonate solution (1×100 mL), and a saturated aqueous sodium chloride solution (1×100 mL). The organics were dried over sodium sulfate, filtered, and concentrated in vacuo. Flash chromatography (Merck Silica gel 60, 230–400 mesh, 80/20 hexanes/ethyl acetate) afforded 2-[4-(butane-1-sulfonyl)-phenyl]-3-cyclopentyl-propionic acid ethyl ester (144.3 mg, 20.7%) as a yellow oil: EI-HRMS m/e calcd for $C_{20}H_{30}O_4S$ ($M^+$) 366.1865 found 366.1858.

A solution of 2-[4-(butane-1-sulfonyl)-phenyl]-3-cyclopentyl-propionic acid ethyl ester (125.3 mg, 0.34 mmol) in magnesium methoxide in methanol (7.4 wt %, 0.98 mL, 0.68 mmol) was treated with methyl urea (38 mg, 0.51 mmol). This mixture was refluxed at 110° C. for 12 h. The reaction mixture was then concentrated in vacuo. Flash chromatography (Merck Silica gel 60, 230–400 mesh, 50/50 hexanes/ethyl acetate) afforded 1-{2-[4-(butane-1-sulfonyl)- phenyl]-3-cyclopentyl-propionyl}-3-methyl-urea (61.8 mg, 45.8%) as a white solid: mp 189–191° C.; EI-HRMS m/e calcd for $C_{20}H_{30}N_2O_4S$ (M+) 395.2005, found 395.2008.

Example 40

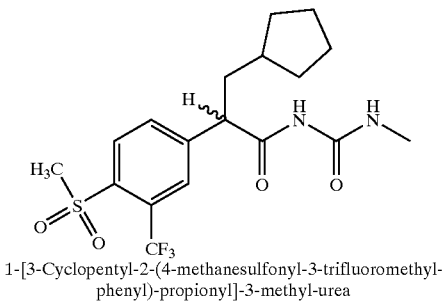

1-[3-Cyclopentyl-2-(4-methanesulfonyl-3-trifluoromethyl-phenyl)-propionyl]-3-methyl-urea A solution of freshly prepared lithium diisopropylamide (35.3 mL of a 0.31 M stock solution, 10.9 mmol) cooled to −78° C. was treated with (4-fluoro-3-trifluoromethyl-phenyl)-acetic acid (1.11 g, 5.0 mmol) in tetrahydrofuran/1,3-dimethyl-3,4,5,6-tetrahydro-2(1H)-pyrimidinone (12.4 mL, 3:1). The resulting solution was stirred at −78° C. for 1 h. At this time, the reaction was treated with a solution of iodomethylcyclopentane (1.16 g, 5.52 mmol) in 1,3-dimethyl-3,4,5,6-tetrahydro-2(1H)-pyrimidinone (1.2 mL). The reaction mixture was stirred at −78° C. for 4 h. The reaction was then warmed to 25° C. and was stirred at 25° C. for 48 h. This solution was then quenched by the slow addition of the reaction mixture to an aqueous solution of 2N hydrochloric acid (50 mL). The product was extracted into ethyl acetate (3×100 mL) and diethyl ether (1×50 mL). The organics were dried over magnesium sulfate and sodium sulfate, filtered, and concentrated in vacuo. Flash chromatography (Merck Silica gel 60, 230–400 mesh, 50/50 hexanes/ethyl acetate with acetic acid) afforded 3-cyclopentyl-2-(4-fluoro-3-trifluoromethyl-phenyl)-propionic acid (1.28 g, 84.3%) as a white solid: mp 66–68° C.; EI-HRMS m/e calcd for $C_{15}H_{16}F_4O_2$ (M+) 305.1165, found 305.1174.

A solution of 3-cyclopentyl-2-(4-fluoro-3-trifluoromethyl-phenyl)-propionic acid (7.77 g, 25.3 mmol) in methanol (50 mL) was treated slowly with concentrated sulfuric acid (0.01 mL). The resulting reaction mixture was heated under reflux for 24 h. The reaction mixture was allowed to cool to 25° C. and then concentrated in vacua. The residue was dissolved in ethyl acetate (75 mL) and washed with a saturated aqueous sodium bicarbonate solution (1×50 mL), water (1×50 mL), and a saturated aqueous sodium chloride solution (4×50 mL). The organics were dried over magnesium sulfate and sodium sulfate, filtered, and concentrated in vacuo to afford 3-cyclopentyl-2-(4-fluoro-3-trifluoromethyl-phenyl)-propionic acid methyl ester (8.48 g, 87.5%) as yellow oil: EI-HRMS m/e calcd for $C_{16}H_{18}F_4O_2$ (M+) 318.1243, found 318.1240.

A solution of 3-cyclopentyl-2-(4-fluoro-3-trifluoromethyl-phenyl)-propionic acid methyl ester (7.0 g, 21.9 mmol) in N,N-dimethylformamide (50 mL) was treated with sodium methanethiolate (2.61 g, 33.0 mmol). The reaction mixture was then heated to 100–110° C. for 24 h. At this time, the reaction was poured onto a mixture of ice and an aqueous solution of 2N hydrochloric acid (100 mL). This mixture was extracted into ethyl acetate (3×75 mL) and diethyl ether (1×50 mL). The organics were then washed with water (1×75 mL) and a saturated aqueous sodium chloride solution (3×100 mL). The organics were dried over magnesium sulfate and sodium sulfate, filtered, and concentrated in vacua. Flash chromatography (Merck Silica gel 60, 230–400 mesh, 85/15 hexanes/ethyl acetate) afforded 3-cyclopentyl-2-(4-methylsulfanyl-3-trifluoromethyl-phenyl)-propionic acid methyl ester (2.48 g, 35.5%) as a pale yellow oil: EI-HRMS m/e calcd for $C_{17}H_{21}F_3O_2S$ (M+) 346.1214, found 346.1212.

A solution of 3-cyclopentyl-2-(4-methylsulfanyl-3-trifluoromethyl-phenyl)-propionic acid methyl ester (2.36 g, 6.81 mmol) in methylene chloride (75 mL) at 25° C. was treated with 3-chloroperoxybenzoic acid (80–85% grade, 9.69 g, 40.1 mmol). The reaction mixture was stirred at 25° C. for 16 h. At this time, the reaction was diluted with methylene chloride (75 mL). This solution was washed with a saturated aqueous sodium bisulfite solution (2×50 mL), water (1×50 mL), a saturated aqueous sodium chloride solution (3×75 mL), a saturated aqueous sodium bicarbonate solution (1×75 mL), and a saturated aqueous sodium chloride solution (3×75 mL). The organics were dried over magnesium sulfate and sodium sulfate, filtered, and concentrated in vacuo to afford 3-cyclopentyl-2-(4-methanesulfonyl-3-trifluoromethyl-phenyl)-propionic acid methyl ester (2.88 g) as a clear oil: EI-HRMS m/e calcd for $C_{17}H_{21}F_3O_2S$ (M+) 378.1112, found 378.1116.

A solution of 3-cyclopentyl-2-(4-methylsulfanyl-3-trifluoromethyl-phenyl)-propionic acid methyl ester (378 mg, 1.0 mmol) in magnesium methoxide in methanol (7.4 wt %, 2.0 mL, 1.40 mmol) was treated with methyl urea (148 mg, 2.0 mmol). This mixture was refluxed at 110° C. for 12 h. The reaction mixture was then concentrated in vacuo. Flash chromatography (Merck Silica gel 60, 230–400 mesh, 40/60 hexanes/ethyl acetate) afforded 1-[3-cyclopentyl-2-(4-methanesulfonyl-3-trifluoromethyl-phenyl)-propionyl]-3-methyl-urea (61.8 mg, 45.8%) as a white solid: mp 268–270° C.; EI-HRMS m/e calcd for $C_{18}H_{23}F_3N_2O_4S$ (M+) 420.1331, found 420.1345.

Example 41

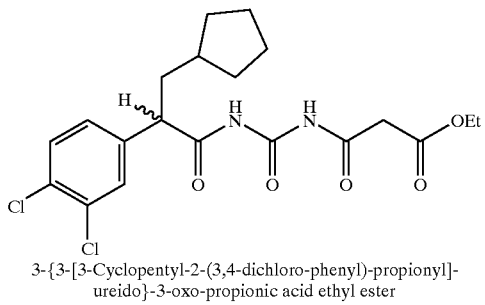

3-{3-[3-Cyclopentyl-2-(3,4-dichloro-phenyl)-propionyl]-ureido}-3-oxo-propionic acid ethyl ester A solution of [3-cyclopentyl-2-(3,4-dichloro-phenyl)-propionyl]-urea (prepared in Example 1B-d, 402 mg, 1.22 mmol) and pyridine (0.15 mL, 1.83 mmol), in toluene (15 mL) was treated with ethyl malonyl chloride (0.19 mL, 1.5 mmol). The resulting reaction mixture was heated at reflux for 2 h. At this time, additional pyridine (0.15 mL, 1.83 mmol) and ethyl malonyl chloride (0.19 mL, 1.5 mmol) were added. The reaction was then heated at reflux for 90 min. The reaction was then cooled to 25° C., diluted with ethyl acetate (50 mL), washed with water (2×25 mL), and dried over magnesium sulfate. The solution was concentrated in vacuo. Flash column chromatography (Merck Silica gel 60, 230–400 mesh, 4/1 hexane/ethyl acetate) afforded 3-{3-[3-cyclopentyl-2-(3,4-dichloro-phenyl)- propionyl]-ureido}-3-oxo-propionic acid ethyl ester (172 mg, 32%) as a colorless gum: EI-HRMS m/e calcd for $C_{20}H_{24}Cl_2N_2O_5$ (M$^+$) 443.1140, found 443.1128.

Example 42

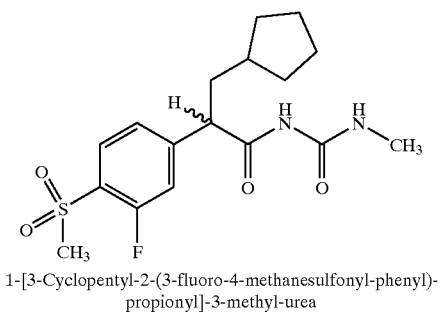

1-[3-Cyclopentyl-2-(3-fluoro-4-methanesulfonyl-phenyl)-propionyl]-3-methyl-urea

A solution of 4-chloro-3-nitrophenylacetamide (2.00 g, 9.32 mmol) in methanol (40 mL) was treated with Amberlyst® 15 ion exchange resin (15.00 g). The resulting reaction mixture was heated under reflux for 64 h. The reaction mixture was allowed to cool to 25° C. and then filtered to remove the Amberlyst® 15 ion exchange resin. The filtrate was concentrated in vacuo. Flash chromatography (Merck Silica gel 60, 230–400 mesh, 3/1 hexanes/ethyl acetate) afforded 4-chloro-3-nitrophenylacetic acid methyl ester (1.91 g, 89%) as a yellow oil: EI-HRMS m/e calcd for $C_9H_8ClNO_4$ (M$^+$) 229.0142, found 229.0146.

A solution of diisopropylamine (3.35 mL, 23.9 mmol) in dry tetrahydrofuran (45 mL) and 1,3-dimethyl-3,4,5,6-tetrahydro-2(1H)-pyrimidinone (15 mL) cooled to −78° C. was treated dropwise with a 2.5M solution of n-butyllithium in hexanes (9.56 mL, 23.9 mmol) over a 10 min period. The pale yellow reaction mixture was stirred at −78° C. for 20 min and then slowly treated with a solution of 4-chloro-3-nitrophenylacetic acid methyl ester (5.00 g, 21.8 mmol) in a small amount of tetrahydrofuran over a 15 min period. The reaction mixture turned deep purple (almost black) in color. The reaction mixture was then stirred at −78° C. for 1 h. At this time, the reaction was treated with a solution of iodomethylcyclopentane (4.58 g, 21.8 mol) in a small amount of dry tetrahydrofuran. The reaction mixture was then stirred at −78° C. and then allowed to warm to 25° C., where it was stirred for 48 h. The reaction mixture was quenched with a saturated aqueous ammonium chloride solution (50 mL), and the resulting reaction mixture was concentrated in vacuo to remove tetrahydrofuran. The remaining residue was diluted with ethyl acetate (150 mL) and water (50 mL). The organic phase was washed with a saturated aqueous sodium chloride solution, dried over magnesium sulfate, filtered, and concentrated in vacuo. Flash chromatography (Merck Silica gel 60, 230–400 mesh, 4/1 hexanes/ethyl acetate) afforded 2-(4-chloro-3-nitrophenyl)-3-cyclopentyl-propionic acid methyl ester (2.17 g, 32%) as a yellow oil: EI-HRMS m/e calcd for $C_{15}H_{18}ClNO_4$ (M$^+$) 311.0924, found 311.0927.

A solution of 2-(4-chloro-3-nitrophenyl)-3-cyclopentyl-propionic acid methyl ester (1.00 g, 3.21 mmol) and sodium methanesulfinate (0.36 g, 3.53 mmol) in dimethyl sulfoxide (3mL) was heated at 130° C. for 5 h. The black reaction mixture was then poured over ice (20 g), resulting in the formation of a brown sticky substance. The resulting mixture was then treated with ethyl acetate (50 mL) and water (50 mL), and the layers were separated. The aqueous layer was further extracted with ethyl acetate (2×50 mL). The combined organic layers were washed with a saturated aqueous sodium chloride solution, dried over magnesium sulfate, filtered, and concentrated in vacuo. Flash chromatography (Merck Silica gel 60, 230–400 mesh, 1/1 hexanes/ethyl acetate) afforded 3-cyclopentyl-2-(4-methanesulfonyl-3-nitrophenyl)-propionic acid methyl ester (0.95 g, 84%) as a yellow gel: FAB-HRMS m/e calcd for $C_{16}H_{21}NO_6S$ (M+H)$^+$356.1169, found 356.1175.

A solution of 3-cyclopentyl-2-(4-methanesulfonyl-3-nitrophenyl)-propionic acid methyl ester (1.50 g, 4.22 mmol) in methanol (30 mL) was treated with a solution of ammonium chloride (474 mg, 8.86 mmol) in water (3 mL). The reaction mixture was stirred at 25° C. for 5 min and then treated with zinc dust (2.70 g, 41.36 mmol). The reaction mixture was heated under reflux for 2 h. The reaction mixture was allowed to cool to 25° C. and then filtered through a pad of celite. The filtrate was concentrated in vacuo. The resulting orange oil was dissolved in ethyl acetate, dried over magnesium sulfate, filtrated, and concentrated in vacuo. Flash chromatography (Merck Silica gel 60, 230–400 mesh, 2/1 hexanes/ethyl acetate) afforded 2-(3-amino-4-methanesulfonyl-phenyl)-3-cyclopentyl-propionic acid methyl ester (1.49 g, 98%) as a white solid: mp 98–100° C.; EI-HRMS m/e calcd for $C_{16}H_{23}NO_4S$ (M$^+$) 325.1348, found 325.1358.

A slurry of nitrosonium tetrafluoroborate (215 mg, 1.84 mmol) in methylene chloride (6 mL) cooled to 0° C. was treated dropwise with a solution of 2-(3-amino-4-methanesulfonyl-phenyl)-3-cyclopentyl-propionic acid methyl ester (500 mg, 1.54 mmol) in a small amount of methylene chloride. The resulting reaction mixture was stirred at 0° C. for 1 h. The reaction mixture was then allowed to warm to 25° C. and then treated with 1,2-dichlorobenzene (6 mL). The resulting reaction mixture was heated at 100° C. for 1 h, during which time, the methylene chloride was distilled off. After 1 h at 100° C., the reaction mixture was allowed to cool to 25° C. The crude reaction mixture was directly purified by flash chromatography, (Merck Silica gel 60, 230–400 mesh, 9/1 hexanes/ethyl acetate to elute 1,2-dichlorobenzene then 2/1 hexanes/ethyl acetate), to afford impure 3-cyclopentyl-2-(3-fluoro-4-methanesulfonyl-phenyl)-propionic acid methyl ester as a yellow oil. Repurification by flash chromatography (Merck Silica gel 60, 230–400 mesh, 3/1 hexanes/ethyl acetate) afforded pure 3-cyclopentyl-2-(3-fluoro-4-methanesulfonyl-phenyl)-propionic acid methyl ester (214 mg, 42%) as a pale yellow oil which solidified upon sitting at 25° C. to a pale yellow solid: mp 66–68° C.; EI-HRMS m/e calcd for $C_{16}H_{21}FO_4S$ (M$^+$) 328.1144, found 328.1148.

3-Cyclopentyl-2-(3-fluoro-4-methanesulfonyl-phenyl)-propionic acid methyl ester (90 mg, 0.274 mmol) and methyl urea (61 mg, 0.822 mmol) were treated with a solution of magnesium methoxide in methanol (7.4 wt %, 1.0 mL, 0.685 mmol). The reaction mixture was then concentrated in vacuo to approximately one-half the volume of methanol. The resulting reaction mixture was then heated under reflux for 24 h. The resulting cloudy, white reaction mixture was allowed to cool to 25° C. and then filtered through celite. The celite was thoroughly washed with ethyl acetate. The filtrate was concentrated in vacuo. Flash chromatography (Merck Silica gel 60, 230–400 mesh, 1/1 hexanes/ethyl acetate) afforded 1-[3-cyclopentyl-2-(3-fluoro4-methanesulfonyl-phenyl)-propionyl]-3-methyl-urea (23.3 mg, 23%) as a white solid: mp 199–200° C.; EI-HRMS m/e calcd for $C_{17}H_{23}FN_2O_4S$ (M$^+$) 370.1362, found 370.1370.

Example 43

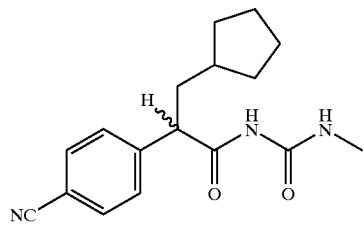

1-[2-(4-Cyano-phenyl)-3-cyclopentyl-propionyl]-3-methyl-urea

A solution of (4-bromo-phenyl)-acetic acid (6.77 g, 31.48 mmol) in methanol (32 mL) was treated with a catalytic amount of concentrated sulfuric acid (3 drops). The reaction mixture was then heated to reflux for 24 h. At this time, the reaction was concentrated in vacuo. The residue was treated with an aqueous solution of sodium bicarbonate (100 mL). This solution was extracted with ethyl acetate (3×100 mL). The organic layers were washed with a saturated aqueous solution of sodium chloride, dried over sodium sulfate, filtered and concentrated in vacuo to afford (4-bromo-phenyl)-acetic acid methyl ester (6.75 g, 94%) as a yellow oil. The product was used without further purification. A solution of freshly prepared lithium diisopropylamide (50.5 mL of 0.3 M, 15.15 mmol) cooled to −78° C. was treated with (4-bromo-phenyl)-acetic acid methyl ester (3.36 g, 14.67 mmol) in tetrahydrofuran/1,3-dimethyl-3,4,5,6-tetrahydro-2(1H)-pyrimidinone (37 mL, 3:1). The resulting solution was stirred at −78° C. for 45 min. At this time, the reaction was treated with a solution of iodomethylcyclopentane (3.24 g, 15.45 mmol) in 1,3-dimethyl-3,4,5,6-tetrahydro-2(1H)-pyrimidinone (3.24 mL). The reaction mixture was stirred at −78° C. for 4 h. The reaction was warmed to 25° C. and stirred at 25° C. for 20 h. The reaction mixture was then quenched by the slow addition of a saturated ammonium chloride solution (40 mL). The reaction mixture was then poured into water (100 mL) and the product was extracted into ethyl acetate (3×75 mL). The organics were washed with a saturated aqueous sodium chloride solution (3×100 mL) and a saturated aqueous solution of lithium chloride (3×100 mL), dried over sodium sulfate and magnesium sulfate, filtered, and concentrated in vacuo. Flash chromatography (Merck Silica gel 60, 230–400 mesh, 80/20 hexanes/ethyl acetate) afforded 2-(4-bromo-phenyl)-3-cyclopentyl-propionic acid methyl ester (3.86 g, 84.6%) as a clear oil: EI-HRMS m/e calcd for $C_{15}H_{19}BrO_2$ ($M^+$) 310.0568 found 310.0564.

A solution of 2-(4-bromo-phenyl)-3-cyclopentyl-propionic acid methyl ester (1.55 g, 5.0 mmol) in N,N-dimethylformamide (12.5 mL) was treated with copper cyanide (672 mg, 7.5 mmol). This mixture was heated at reflux for 21 h. The reaction mixture was cooled to 25° C. and poured into aqueous ammonium hydroxide (25 mL). The resulting solution was diluted with water (25 mL). This solution was extracted with ethyl acetate (3×50 mL). The organics were washed with a saturated aqueous sodium chloride solution (3×75 mL), dried over sodium sulfate and magnesium sulfate, filtered, and concentrated in vacuo. Flash chromatography (Merck Silica gel 60, 230–400 mesh, 90/10 hexanes/ethyl acetate) afforded 2-(4-cyano-phenyl)-3-cyclopentyl-propionic acid methyl ester (1.17 g, 91.3%) as a clear oil; EI-HRMS m/e calcd for $C_{16}H_{19}NO_2$ ($M^+$) 257.1415 found 257.1406.

A mixture of 2-(4-cyano-phenyl)-3-cyclopentyl-propionic acid methyl ester (257 mg, 1.0 mmol) and methyl urea (148 mg, 2.0 mmol) in a solution of magnesium methoxide in methanol (7.4 wt %, 2.0 mL, 1.40 mmol) was heated to reflux for 48 h. The reaction mixture was then concentrated in vacuo. Flash chromatography (Merck Silica gel 60, 230–400 mesh, 70/30 ethyl acetate/hexanes) afforded 1-[2-(4-cyano-phenyl)-3-cyclopentyl-propionyl]-3-methyl-urea (48.8 mg, 16.3%) as a white solid: mp 61–65° C.; FAB-HRMS m/e calcd for $C_{17}H_{21}N_3O_2$ $(M+H)^+$ 300.1712 found 300.1722.

BIOLOGICAL ACTIVITY EXAMPLES

Example A

In Vitro Glucokinase Activity

Glucokinase Assay: Glucokinase (GK) was assayed by coupling the production of glucose-6-phosphate to the generation of NADH with glucose-6-phosphate dehydrogenase (G6PDH, 0.75–1 kunits/mg; Boehringer Mannheim, Indianapolis, Ind.) from *Leuconostoc mesenteroides* as the coupling enzyme (Scheme 2). Recombinant Scheme 2

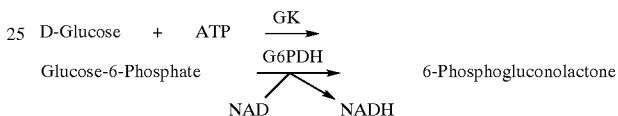

Human liver GK1 was expressed in *E. coli* as a glutathione S-transferase fusion protein (GST-GK) [Liang et al, 1995 ] and was purified by chromatography over a glutathione-Sepharose 4 B affinity column using the procedure provided by the manufacturer (Amersham Pharmacia Biotech, Piscataway, N.J.). Previous studies have demonstrated that the enzymatic properties of native GK and GST-GK are essentially identical (Liang et al, 1995; Neet et al., 1990).

The assay was conducted at 25° C. in a flat bottom 96-well tissue culture plate from Costar (Cambridge, Mass.) with a final incubation volume of 120 μL. The incubation mixture contained: 25 mM Hepes buffer (pH, 7.1), 25 mM KCl, 5 mM D-glucose, 1 mM ATP, 1.8 mM NAD, 2 mM $MgCl_2$, 1 μM sorbitol-6-phosphate, 1 mM dithiothreitol, test drug or 10% DMSO, 1.8 unit/ml G6PDH, and GK (see below). All organic reagents were >98% pure and were from Boehringer Mannheim with the exceptions of D-glucose and Hepes that were from Sigma Chemical Co, St Louis, Mo. Test compounds were dissolved in DMSO and were added to the incubation mixture minus GST-GK in a volume of 12 μl to yield a final DMSO concentration of 10%. This mix was preincubated in the temperature controlled chamber of a SPECTRAmax 250 microplate spectrophotometer (Molecular Devices Corporation, Sunnyvale, Calif.) for 10 minutes to allow temperature equilibrium and then the reaction was started by the addition of 20 μl GST-GK.

After addition of enzyme, the increase in optical density (OD) at 340 nm was monitored over a 10 minute incubation period as a measure of GK activity. Sufficient GST-GK was added to produce an increase in $OD_{340}$ of 0.08 to 0.1 units over the 10 minute incubation period in wells containing 10% DMSO, but no test compound.

Preliminary experiments established that the GK reaction was linear over this period of time even in the presence of activators that produced a 5-fold increase in GK activity. The GK activity in control wells was compared with the activity in wells containing test GK activators, and the concentration of activator that produced a 50% increase in the activity of (K, i.e., the $SC_{1.5}$, was calculated. All of the compounds of formula I described in the Synthesis Examples had an $SC_{1.5}$ less than or equal to 30 µM.

Liang, Y., Kesavan, P., Wang, L., Niswender, K., Tanizawa, Y., Permut, M. A., Magnuson, M., and Matschinsky, F. M. Variable effects of maturity-onset-diabetes-of-youth (MODY)-associated glucokinase mutations on the substrate interactions and stability of the enzyme. *Biochem. J*. 309: 167–173, 1995.

Neet, K., Keenan, R. P., and Tippett, P. S. Observation of a kinetic slow transition in monomeric glucokinase. *Biochemistry* 29;770–777, 1990.

Example B

In Vivo Activity
Glucokinase Activator in vivo Screen Protocol

C57BL/6J mice are orally dosed via gavage with Glucokinase (GK) activator at 50 mg/kg body weight following a two hour fasting period. Blood glucose determinations are made five times during the six hour post-dose study period.

Mice (n=6) are weighed and fasted for a two hour period prior to oral treatment. GK activators are formulated at 6.76 mg/ml in Gelucire vehicle (Ethaol:Gelucire44/14:PEG400q.s. 4:66:30 v/w/v. Mice are dosed orally with 7.5 µL formulation per gram of body weight to equal a 50 mg/kg dose. Immediately prior to dosing, a pre dose (time zero) blood glucose reading is acquired by snipping off a small portion of the animals tail (~1 mm) and collecting 15 µL blood into a heparinized capillary tube for analysis. Following GK activator administration, additional blood glucose readings are taken at 1, 2, 4, and 6 hours post dose from the same tail wound. Results are interpreted by comparing the mean blood glucose values of six vehicle treated mice with six GK activator treated mice over the six hour study duration. Compounds are considered active when they exhibit a statistically significant (p≦0.05) decrease in blood glucose compared to vehicle for two consecutive assay time points.

What is claimed is:

1. A compound comprising an amide of the formula

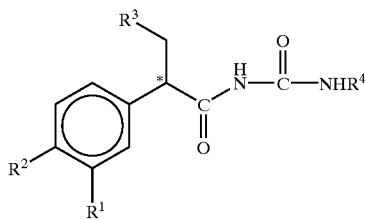

wherein $R^1$ and $R^2$ are independently hydrogen, halo, amino, nitro, cyano, sulfonamido, lower alkyl, perfluoro-lower alkyl, lower alkyl thio, perfluoro-lower alkyl thio, lower alkyl sulfonyl, or perfluoro-lower alkyl sulfonyl; $R^3$ is cycloallyl having from 3 to 7 carbon atoms; $R^4$ is hydrogen, lower allyl, lower alkenyl, hydroxy lower alkyl halo lower alkyl;

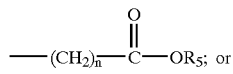

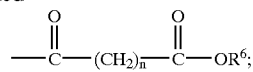

$R^5$ and $R^6$ are hydrogen or lower alkyl; and n is 0, 1, 2, 3 or 4; or a pharmaceutically acceptable salt thereof.

2. The compound of claim 1, wherein the amide is in the "R" configuration at the asymmetric carbon shown.

3. The compound of claim 1 wherein $R^4$ is hydrogen, lower alkyl, or lower alkenyl.

4. The compound of claim 3 wherein $R^3$ is cyclopentyl.

5. The compound of claim 4, wherein $R^1$ and $R^2$ are hydrogen.

6. The compound of claim 5, wherein said amide is 1-(3-cyclopentyl-2-phenyl propionyl)-3-methyl-urea.

7. The compound of claim 4, wherein one of $R^1$ and $R^2$ is hydrogen and the other is cyano or halo.

8. The compound of claim 7, wherein said amide is 1-[2-(3-chloro-phenyl)-3cyclopentyl-propionyl]-3-methyl-urea.

9. The compound of claim 7, wherein said amide is 1-[2-(4-chloro-phenyl)-3-cyclopentyl-propionyl]-3-methyl-urea.

10. The compound of claim 7, wherein said amide is 1-[2-(4-cyano-phenyl)-3-cyclopentyl-propionyl]-3-methyl-urea.

11. The compound of claim 7, wherein said amide is 1-[2-(4-bromo-phenyl)-3-cyclopentyl-propionyl]-3-methyl urea.

12. The compound of claim 4, wherein $R^1$ and $R^2$ are each independently halo.

13. The compound of claim 12, wherein said amide is [3-cyclopentyl-2-(3,4-dichloro-phenyl)-propionyl]-urea.

14. The compound of claim 12, wherein said amide is 1-[3-cyclopentyl-2-(3,4-dichloro-phenyl)-propionyl]-3-methyl-urea.

15. The compound of claim 12, wherein said amide is 1-[3-cyclopentyl-2(R)-(3,4-dichloro-phenyl)-propionyl]-3-ethyl-urea.

16. The compound of claim 12, wherein said amide is 1-allyl-3-[3-cyclopentyl-2-(3,4-dichloro-phenyl)-proprionyl]-urea.

17. The compound of claim 12, wherein said amide is 1-allyl-3-[3-cyclopentyl-2(R)-(3,4-dichloro-phenyl)-proprionyl]-urea.

18. The compound of claim 12, wherein said amide is 1-[3-cyclopentyl-2-(3,4-dichloro-phenyl)-propionyl]-3-ethyl-urea.

19. The compound of claim 12, wherein said amide is 1-[3-cyclopentyl-2(R)-(3,4-dichloro-phenyl)-propionyl]-3-methyl-urea.

20. The compound of claim 12, wherein said amide is 1-[3-cyclopentyl-2-(3,4-dichloro-phenyl)-propionyl]-3-isopropyl-urea.

21. The compound of claim 12, wherein said amide is 1-[3-cyclopentyl-2-(3,4-dichloro-phenyl)-propionyl]-3-propyl-urea.

22. The compound of claim 12, wherein said amide is 1-[3-cyclopentyl-2-(3,4-difluoro-phenyl)-propionyl]-3-methyl-urea.

23. The compound of claim 4, wherein one of $R_1$ and $R^2$ is hydrogen or halo and the other is nitro.

24. The compound of claim 23 wherein said amide is 1-[2-(4-chloro-3-nitro-phenyl)-3-cyclopentyl-proprionyl]-3-methyl-urea.

25. The compound of claim 23, wherein said amide is 1-[3-cyclopentyl-2-(4-nitro-phenyl)-propionyl]-3-methyl-urea.

26. The compound of claim 4, wherein one of $R^1$ and $R^2$ is hydrogen, lower alkyl thio or perfluoro-lower alkyl thio and the other is lower alkyl thio or perfluoro-lower alkyl thio.

27. The compound of claim 26, wherein said amide is 1-[3-cyclopentyl-2-(4-trifluoromethylsulfanyl-phenyl)-propionyl]-3-methyl urea.

28. The compound of claim 26, wherein said amide is 1-[3-cyclopentyl-2-(4-methylsulfanyl-phenyl)-propionyl]-3-methyl urea.

29. The compound of claim 4, wherein one of $R^1$ and $R^2$ is hydrogen or perfluoro-lower alkyl sulfonyl and the other is perfluoro-lower alkyl sulfonyl.

30. The compound of claim 29, wherein said amide is 1-[3-cyclopentyl-2-(4-trifluoromethanesulfonyl-phenyl)-propionyl]-3-methyl urea.

31. The compound of claim 29, wherein said amide is 1-[3-cyclopentyl-2-(3-trifluoromethanesulfonyl-phenyl)-propionyl]-3-methyl urea.

32. The compound of claim 4 wherein at least one of $R^1$ and $R^2$ is lower alkyl sulfonyl.

33. The compound of claim 32 wherein one of $R^1$ and $R^2$ is hydrogen or lower alkyl sulfonyl and the other is lower alkyl sulfonyl.

34. The compound of claim 33 wherein $R^2$ is lower alkyl sulfonyl.

35. The compound of claim 34, wherein said amide is 1-[3-cyclopentyl-2-(4-methanesulfonyl-phenyl)-propionyl]-3-methyl urea.

36. The compound of claim 34 wherein said amide is 1-{2-[4-(butane-1-sulfonyl)-phenyl]-3-cyclopentyl-proprionyl}-3-methyl-urea.

37. The compound of claim 34 wherein said amide is 1-[3-cyclopentyl-2-(4-ethanesulfonyl-phenyl)-propionyl]-3-methyl-urea.

38. The compound of claim 34 wherein said amide is 1-[2-(3,4-bis-methanesulfonyl-phenyl)-3-cyclopentyl-proprionyl]-3-methyl-urea.

39. The compound of claim 32 wherein one of $R^1$ and $R^2$ is cyano or halo and the other is lower alkyl sulfonyl.

40. The compound of claim 39 wherein $R^2$ is lower alkyl sulfonyl.

41. The compound of claim 40, wherein said amide is 1-[2-(3-bromo-4-methanesulfonyl-phenyl)-3-cyclopentyl-proprionyl]-3-methyl-urea.

42. The compound of claim 40, wherein said amide is 1-[3-cyclopentyl-2-(3-fluoro-4-methanesulfonyl-phenyl)-propionyl]-3-methyl-urea.

43. The compound of claim 40, wherein said amide is 1-[2-(3-chloro-4-methanesulfonyl-phenyl)-3-cyclopentyl-proprionyl]-3-methyl-urea.

44. The compound of claim 40, wherein said amide is 1-[2(R)-(3-chloro4-methanesulfonyl-phenyl)-3-cyclopentyl-proprionyl]-3-methyl-urea.

45. The compound of claim 40, wherein said amide is 1-[2-(3-chloro-4-methanesulfonyl-phenyl)-3-cyclopentyl-proprionyl]-3-ethyl-urea.

46. The compound of claim 40, wherein said amide is 1-[2-(3-cyano-4-methanesulfonyl-phenyl)-3-cyclopentyl-proprionyl]-3-methyl-urea.

47. The compound of claim 32, wherein one of $R^1$ and $R^2$ is perfluoro-lower alkyl and the other is lower alkyl sulfonyl.

48. The compound of claim 47 wherein $R^2$ is lower alkyl sulfonyl.

49. The compound of claim 48, wherein said amide is 1-[3-cyclopentyl-2-(4-methanesulfonyl-3-trifluoromethyl-phenyl)-proprionyl]-3-methyl-urea.

50. The compound of claim 4, wherein one of $R^1$ and $R^2$ is perfluoro-lower alkyl and the other is halo.

51. The compound of claim 50 wherein said amide is 1-[3-cyclopentyl-2-(4-fluoro-3-trifluoromethyl-phenyl)-propionyl]-3-methyl urea.

52. The compound of claim 50 wherein said amide is 1-[3-cyclopentyl-2-(3-fluoro-4-trifluoromethyl-phenyl)-propionyl]-3-methyl urea.

53. The compound of claim 32, wherein one of $R^1$ and $R^2$ is nitro and the other is lower alkyl sulfonyl.

54. The compound of claim 53, wherein said amide is 1-[3-cyclopentyl-2-(4-methanesulfonyl-3-nitrophenyl)-propionyl]-3-methyl-urea.

55. The compound of claim 3 wherein one of $R^1$ and $R^2$ is halo or hydrogen and the other is hydrogen.

56. The compound of claim 55 wherein said amide is [2-(4-chloro-phenyl)-4-methyl-pentanoyl]-urea.

57. The compound of claim 55 wherein $R^1$ and $R^2$ are each chlorine.

58. The compound of claim 57, wherein said amide is [3-cyclopropyl-2-(3,4-dichloro-phenyl)-propionyl]-urea.

59. The compound of claim 57, wherein said amide is [3-cyclobutyl-2-(3,4-dichloro-phenyl)-propionyl]-urea.

60. The compound of claim 57 wherein said amide is R-[2-(3,4-dichloro-phenyl)-4-methyl-pentanoyl]-urea.

61. The compound of claim 57, wherein said amide is 1-[2-(3,4-dichloro-phenyl)-4-methyl-pentanoyl]-3-methyl-urea.

62. The compound of claim 57, wherein said amide is 1-[2-(3,4-dichloro-phenyl)-hexanoyl]-3-methyl-urea.

63. The compound of claim 3, wherein $R^1$ is cyclohexyl.

64. The compound of claim 63, when one of $R^1$ and $R^2$ is halo or hydrogen and the other is halo.

65. The compound of claim 64, wherein said amide is 3-[cyclohexyl-2-(3,4-dichloro-phenyl)-propionyl]-urea.

66. The compound of claim 64, wherein said amide is [3-cyclohexyl-2-(3,4-dichloro phenyl)-propionyl]-3-methyl-urea.

67. The compound of claim 3, wherein $R^3$ is cycloheptyl.

68. The compound of claim 67, when one of $R^1$ and $R^2$ is halo or hydrogen and the other is halo.

69. The compound of claim 68, wherein said amide is [3-cycloheptyl-2-(3,4-dichloro-phenyl)-propionyl]-urea.

70. A compound of claim 1 wherein $R^4$ is

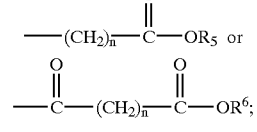

71. The compound of claim 70 wherein $R^3$ is cyclopentyl.

72. The compound of claim 71 wherein $R^1$ and $R^2$ are independently halo.

73. The compound of claim 72, wherein said amide is 3-{3-[3-cyclopentyl-2-(3,4-dichloro-phenyl)-propionyl]-ureido}-propionic acid ethyl ester.

74. The compound of claim 72, wherein said amide is {3-[3-cyclopentyl-2-(3,4-dichloro-phenyl)-propionyl]-ureido}-acetic acid ethyl ester.

75. The compound of claim 72, wherein said amide is {3-[3-cyclopentyl-2-(3,4-dichloro-phenyl)-propionyl]-ureido}-acetic acid methyl ester.

76. The compound of claim 72, wherein said amide is 3-{3-[3-cyclopentyl-2-(3,4-dichloro-phenyl)-propionyl]-ureido}-propionic acid methyl ester.

77. The compound of claim 72, wherein said amide is {3-[3-cyclopentyl-2(R)-(3,4-dichloro-phenyl)-propionyl]-ureido}-acetic acid ethyl ester.

78. The compound of claim 72 wherein said amide is 3-{3-[3-cyclopentyl-2-(3,4-dichloro-phenyl)-propionyl]-ureido}-3-oxo-propionic acid ethyl ester.

79. A compound of claim 1 wherein $R^4$ is hydroxy lower alkyl, or halo lower alkyl.

80. A compound of claim 79 wherein $R^3$ is cyclopentyl.

81. A compound of claim 80 wherein $R^1$ and $R^2$ are independently halo.

82. A compound of claim 81 wherein the amide is 1-[3-cyclopentyl-2-(3,4-dichloro-phenyl)-proprionyl]-3-(2-hydroxy-ethyl)-urea.

83. A compound of claim 81 wherein the amide is 1-[3-cyclopentyl-2-(3,4-dichloro-phenyl)-proprionyl]-3-(2-hydroxy-propyl)-urea.

84. A compound of claim 81 wherein the amide is 1-[3-cyclopentyl-2-(3,4-dichloro-phenyl)-proprionyl]-3-(3-hydroxy-propyl)-urea.

85. A compound of claim 81 wherein the amide is 1-[3-cyclopentyl-2(R)-(3,4-dichloro-phenyl)-proprionyl]-3-(2-hydroxy-propyl)-urea.

86. A compound of claim 81 wherein the amide is 1-(2-chloro-ethyl)-3-[3-cyclopentyl-2-(3,4-dichloro-phenyl)-proprionyl]-urea.

87. A compound of claim 81 wherein the amide is 1-[3-cyclopentyl-2(R)-(3,4-dichloro-phenyl)-proprionyl]-3-(3-hydroxy-propyl)-urea.

* * * * *

UNITED STATES PATENT AND TRADEMARK OFFICE
CERTIFICATE OF CORRECTION

PATENT NO.    : 6,528,543 B1
DATED         : March 4, 2003
INVENTOR(S)   : Fred Thomas Bizzarro et al.

It is certified that error appears in the above-identified patent and that said Letters Patent is hereby corrected as shown below:

Column 65,
Line 60, "cycloallyl" should read -- cycloalkyl --.
Line 61, "lower allyl" should read -- lower alkyl --.

Column 66,
Line 60, "$R_1$ and $R^2$" should read -- $R^1$ and $R^2$ --.

Column 67,
Line 53, "(3-chloro4-methanesulfonyl-phenyl)" should read -- (3-chloro-4-methanesulfonyl-phenyl) --.

Signed and Sealed this

Eighth Day of July, 2003

JAMES E. ROGAN
*Director of the United States Patent and Trademark Office*